US009171342B2

(12) United States Patent
Neal

(10) Patent No.: US 9,171,342 B2
(45) Date of Patent: Oct. 27, 2015

(54) CONNECTING PATIENTS WITH EMERGENCY/URGENT HEALTH CARE

(75) Inventor: Michael John Neal, Tampa, FL (US)

(73) Assignee: Healthgrades Operating Company, Inc., Denver, CO (US)

( * ) Notice: Subject to any disclaimer, the term of this patent is extended or adjusted under 35 U.S.C. 154(b) by 325 days.

(21) Appl. No.: 13/004,792

(22) Filed: Jan. 11, 2011

(65) Prior Publication Data

US 2011/0112858 A1      May 12, 2011

Related U.S. Application Data

(63) Continuation-in-part of application No. 12/613,822, filed on Nov. 6, 2009.

(51) Int. Cl.
| | | |
|---|---|---|
| *G06F 3/00* | (2006.01) | |
| *G06Q 50/22* | (2012.01) | |
| *G06F 19/00* | (2011.01) | |
| *G06Q 30/02* | (2012.01) | |

(52) U.S. Cl.
CPC .............. *G06Q 50/22* (2013.01); *G06F 19/327* (2013.01); *G06Q 30/02* (2013.01)

(58) Field of Classification Search
CPC ....... G06Q 50/22; G06Q 10/10; G06Q 50/24; G06Q 10/00; G06Q 40/08; G06Q 30/02; G06Q 30/0277; G06Q 30/0641; G06Q 10/087; G06Q 30/0625; G06Q 20/202; G06Q 20/203; G06Q 30/0202; G06Q 30/0226
USPC ............................. 715/757, 739, 742; 705/2, 3
See application file for complete search history.

(56) References Cited

U.S. PATENT DOCUMENTS 5,365,425 A      11/1994   Torma et al.
5,517,405 A      5/1996    McAndrew et al.
(Continued)

FOREIGN PATENT DOCUMENTS

WO    WO2008148129 A1 *  12/2008

OTHER PUBLICATIONS

GeoAccess.com [online], [retrieved on Feb. 2010]. Retrieved from the internet: <URL: http:www.ingenix.com> (2010) 1 page.
(Continued)

*Primary Examiner* — Amy Ng
*Assistant Examiner* — Di Xiao
(74) *Attorney, Agent, or Firm* — Merchant & Gould P.C.

(57)  ABSTRACT

A computer network-based service provides search capabilities and mechanisms for connecting potential patients with emergency, urgent, and convenient care facilities. Patients make informed decisions regarding their treatment options by reviewing search results regarding facility wait times, geographic proximities of facilities, quality ratings of facilities for particular specialties, etc. Upon selecting a facility, patients may electronically transmit a notification to the facility indicating their medical condition(s) and estimated arrival time. The facility may approve or deny the treatment request by sending an electronic response. The facility may also request further information to triage the patient before his/her actual arrival and/or may provide instructions to assist the patient while en route. Navigation satellite systems may identify the patient's location for processing search requests and determining the proximity of facilities. Further, contact mechanisms, e.g., phone numbers, for contacting facilities directly may be accessed from the search service and tracked.

20 Claims, 21 Drawing Sheets

(56) References Cited

U.S. PATENT DOCUMENTS

| | | | |
|---|---|---|---|
| 5,652,842 | A | 7/1997 | Siegrist, Jr. et al. |
| 5,706,441 | A | 1/1998 | Lockwood |
| 5,724,379 | A | 3/1998 | Perkins et al. |
| 5,915,240 | A | 6/1999 | Karpf |
| 6,014,629 | A | 1/2000 | DeBruin-Ashton |
| 6,029,138 | A | 2/2000 | Khorasani et al. |
| 6,081,786 | A | 6/2000 | Barry et al. |
| 6,088,677 | A | 7/2000 | Spurgeon |
| 6,108,635 | A | 8/2000 | Herren et al. |
| 6,188,988 | B1 | 2/2001 | Barry et al. |
| 6,269,339 | B1 | 7/2001 | Silver |
| 6,584,445 | B2 | 6/2003 | Papageorge |
| 6,643,641 | B1 | 11/2003 | Snyder |
| 6,658,431 | B1 | 12/2003 | Norman, Jr. |
| 6,671,714 | B1 | 12/2003 | Weyer et al. |
| 6,697,783 | B1 | 2/2004 | Brinkman et al. |
| 6,735,569 | B1 | 5/2004 | Wizig |
| 6,738,754 | B1 | 5/2004 | Norman, Jr. |
| 7,065,528 | B2 | 6/2006 | Herz et al. |
| 7,167,855 | B1 | 1/2007 | Koenig |
| 7,383,197 | B1 | 6/2008 | Neuman |
| 7,392,255 | B1 | 6/2008 | Sholtis et al. |
| 7,451,096 | B2 | 11/2008 | Rucker |
| 7,552,063 | B1 | 6/2009 | McEachern |
| 7,580,846 | B2 | 8/2009 | Chishti et al. |
| 7,720,705 | B2 | 5/2010 | Stein |
| 7,752,060 | B2 | 7/2010 | Hicks et al. |
| 8,082,172 | B2 | 12/2011 | Chao et al. |
| 8,719,052 | B2 | 5/2014 | Hicks et al. |
| 2001/0034631 | A1 | 10/2001 | Kiselik |
| 2001/0034639 | A1 | 10/2001 | Jacoby et al. |
| 2001/0039547 | A1 | 11/2001 | Black et al. |
| 2002/0010616 | A1 | 1/2002 | Itzhaki |
| 2002/0019831 | A1 | 2/2002 | Wade |
| 2002/0023109 | A1 | 2/2002 | Lederer et al. |
| 2002/0038233 | A1 | 3/2002 | Shubov et al. |
| 2002/0046041 | A1 | 4/2002 | Lang |
| 2002/0059201 | A1 | 5/2002 | Work |
| 2002/0069085 | A1 | 6/2002 | Engel et al. |
| 2002/0073204 | A1 | 6/2002 | Dutta et al. |
| 2002/0078016 | A1 | 6/2002 | Lium et al. |
| 2002/0099738 | A1 | 7/2002 | Grant |
| 2002/0103676 | A1 | 8/2002 | Yamaguchi et al. |
| 2002/0178030 | A1 | 11/2002 | Loeb |
| 2003/0028406 | A1 | 2/2003 | Herz et al. |
| 2003/0093294 | A1 | 5/2003 | Passantino |
| 2003/0163349 | A1 | 8/2003 | Ho |
| 2003/0167187 | A1 | 9/2003 | Bua |
| 2003/0195838 | A1 | 10/2003 | Henley |
| 2004/0010423 | A1 | 1/2004 | Sameh |
| 2004/0019579 | A1 | 1/2004 | Herz et al. |
| 2004/0019588 | A1 | 1/2004 | Doganata et al. |
| 2004/0024618 | A1 | 2/2004 | Martin et al. |
| 2004/0064440 | A1 | 4/2004 | Norman |
| 2004/0073565 | A1 | 4/2004 | Kaufman et al. |
| 2004/0078211 | A1 | 4/2004 | Schramm-Apple et al. |
| 2004/0111291 | A1 | 6/2004 | Dust et al. |
| 2004/0172282 | A1 | 9/2004 | Benja-Athon |
| 2004/0193447 | A1 | 9/2004 | Joseph |
| 2004/0204837 | A1 | 10/2004 | Singleton |
| 2004/0260577 | A1 | 12/2004 | Dahlin et al. |
| 2004/0260666 | A1 | 12/2004 | Pestotnik et al. |
| 2005/0071189 | A1 | 3/2005 | Blake et al. |
| 2005/0149507 | A1 | 7/2005 | Nye |
| 2005/0160014 | A1 | 7/2005 | Moss et al. |
| 2006/0004623 | A1 | 1/2006 | Jasti |
| 2006/0015369 | A1 | 1/2006 | Bachus et al. |
| 2006/0026037 | A1 | 2/2006 | Lubbert |
| 2006/0080146 | A1 | 4/2006 | Cook et al. |
| 2006/0095299 | A1 | 5/2006 | Hilliard |
| 2006/0136243 | A1* | 6/2006 | Cady ................................ 705/1 |
| 2006/0161456 | A1 | 7/2006 | Baker et al. |
| 2006/0224577 | A1 | 10/2006 | Hullender et al. |
| 2006/0282289 | A1 | 12/2006 | Jacobs et al. |
| 2006/0294138 | A1 | 12/2006 | Stolba |
| 2007/0094044 | A1 | 4/2007 | Stone et al. |
| 2007/0127693 | A1 | 6/2007 | D'Ambrosio et al. |
| 2007/0156455 | A1 | 7/2007 | Tarino et al. |
| 2007/0162307 | A1 | 7/2007 | Austin et al. |
| 2007/0162323 | A1 | 7/2007 | Gorham |
| 2007/0192144 | A1 | 8/2007 | Hauer et al. |
| 2007/0244870 | A1 | 10/2007 | Laurent et al. |
| 2009/0177489 | A1* | 7/2009 | Martinez et al. .................. 705/2 |
| 2009/0206992 | A1* | 8/2009 | Giobbi et al. ................. 340/5.74 |
| 2009/0216633 | A1* | 8/2009 | Whitsett et al. .................. 705/14 |
| 2009/0228490 | A1* | 9/2009 | Faenger .......................... 707/10 |
| 2009/0249229 | A1 | 10/2009 | Offer |
| 2009/0319296 | A1* | 12/2009 | Schoenberg ...................... 705/2 |
| 2010/0017222 | A1 | 1/2010 | Yeluri et al. |
| 2010/0069096 | A1 | 3/2010 | Poola et al. |
| 2010/0070303 | A1 | 3/2010 | Massoumi et al. |
| 2010/0077349 | A1 | 3/2010 | Neal |
| 2010/0094739 | A1 | 4/2010 | Ellis et al. |
| 2010/0268549 | A1 | 10/2010 | Hicks et al. |
| 2011/0022579 | A1 | 1/2011 | Hicks et al. |

OTHER PUBLICATIONS

RevolutionHealth.com [online], [retrieved on Feb. 15, 2010]. Retrieved from internet: <URL: www.RevolutionHealth.com> (No Date) 1 page.

RevolutionHealth.com [online], [retrieved on Mar. 2, 2010]. Retrieved from the internet: <URL: www.RevolutionHealth.com> (Copyright © 2010), 3 pages.

UCompareHalthCare.com [online], [retrieved on Feb. 15, 2010]. Retrieved from the internet: <URL:www.Ucompare.com> (2010) 1 page.

U.S. Appl. No. 11/512,529, filed Aug. 29, 2006, Amendment and Response to Non-Final Office Action, dated Feb. 16, 2010, 17 pgs.

U.S. Appl. No. 11/512,529, filed Aug. 29, 2006, Non Final Office Action dated Nov. 13, 2009, 18 pgs.

U.S. Appl. No. 11/512,529, filed Aug. 29, 2006, Notice of Allowance dated May 14, 2010, 8 pgs.

U.S. Appl. No. 11/512,529, filed Aug. 29, 2006, Requirement for Restriction dated Aug. 31, 2009, 7 pgs.

U.S. Appl. No. 11/512,529, filed Aug. 29, 2006, Response to Election/Restriction filed Sep. 30, 2009, 2 pgs.

U.S. Appl. No. 11/512,529, filed Aug. 29, 2006, Supplemental Amendment filed Apr. 26, 2010, 14 pgs.

Vitals.com [online], [retrieved on Mar. 2, 2010]. Retrieved from the internet: <URL: http://www.vitals.com/> (2006-2010) 2 pages.

WebMD.com [online], [retrieved on Feb. 15, 2010]. Retrieved from internet: <URL: www.WEbMD.com> (2005-2010) 2 pages.

U.S. Appl. No. 12/613,822, filed Nov. 6, 2009, Non-Final Office Action dated Sep. 27, 2011, 27 pages.

*Health Grades* vs. *MDX Medical, Inc.*, Complaint and Demand for Jury Trial, filed Mar. 2, 2011, 6 pages.

*Health Grades* vs. *MDX Medical, Inc.*, Form AO 120 Report on the Filing or Determination of an Action Regarding a Patent or Trademark, filed Mar. 2, 2011, 1 page.

*Health Grades* vs. *MDX Medical, Inc.*, Exhibit A, U.S. Patent No. 7,752,060, in Support of Plaintiff's Complaint, filed Mar. 4, 2011, 36 pages.

*Health Grades* vs. *MDX Medical, Inc.*, MDX Medical, Inc.'s Answer, Affirmative Defenses, Counterclaim and Demand for Jury Trial, filed Apr. 19, 2011, 8 pages.

*Health Grades* vs. *MDX Medical, Inc.*, MDX Medical, Inc.'s Motion Pursuant to Federal Rule of Civil Procedure 56 for Partial Summary Judgment of Non-Infringement, filed Apr. 19, 2011, 92 pages.

*Health Grades* vs. *MDX Medical, Inc.*, Health Grades, Inc.'s Answer to Counterclaim and Defenses, filed May 13, 2011, 4 pages.

*Health Grades* vs. *MDX Medical, Inc.*, Health Grades, Inc.'s Response in Opposition to MDX Medical, Inc.'s Motion for Partial Summary Judgment of Non-Infringement, filed May 20, 2011, 49 pages.

*Health Grades* vs. *MDX Medical, Inc.*, MDX Medical, Inc.'s Unopposed Motion for Jun. 15, 2011 Oral Argument on Motion for Partial Summary Judgment, filed May 24, 2011, 5 pages.

(56) References Cited

OTHER PUBLICATIONS

*Health Grades* vs. *MDX Medical, Inc.*, Unopposed Motion for Leave to File Amendment to Response in Opposition to Motion for Partial Summary Judgment of Non-Infringement, filed May 25, 2011, 5 pages.
*Health Grades* vs. *MDX Medical, Inc.*, Unopposed Motion for Leave to File Amendment to Response in Opposition to Motion for Partial Summary Judgment of Non-Infringement, filed May 26, 2011, 5 pages.
*Health Grades* vs. *MDX Medical, Inc.*, Amendment to Health Grades, Inc.'s Response in Opposition to MDX Medical, Inc.'s Motion for Partial Summary Judgment of Non-Infringement, filed May 27, 2011, 2 pages.
*Health Grades* vs. *MDX Medical, Inc.*, MDX Medical, Inc.'s Reply Memorandum in Support of Its Motion Pursuant to Federal Rule of Civil Procedure 56 for Partial Summary Judgment of Non-Infringement, filed Jun. 3, 2011, 56 pages.
*Health Grades* vs. *MDX Medical, Inc.*, Health Grades, Inc.'s Sur-Reply to MDX Medical, Inc.'s Reply Memorandum in Support of its Motion Pursuant to Federal Rule of Civil Procedure 56 for Partial Summary Judgment of Non-Infringement, filed Jun. 24, 2011, 15 pages.
*Health Grades* vs. *MDX Medical, Inc.*, MDX Medical, Inc.'s Motion to Strike in Part the Sur-Reply of Health Grades, Inc., filed Jun. 28, 2011, 7 pages.
*Health Grades* vs. *MDX Medical, Inc.*, Unopposed Motion to Extend Deadline for Submission of Portions of Infringement Contentions and Related Disclosures, filed Jul. 1, 2011, 4 pages.
*Health Grades* vs. *MDX Medical, Inc.*, Health Grades, Inc.'s Response in Opposition to MDX Medical, Inc.'s Motion to Strike in Part the Sur-Reply of Health Grades, Inc., filed Jul. 22. 2011, 6 pages.
*Health Grades* vs. *MDX Medical, Inc.*, MDX Medical, Inc.'s Reply in Support of Its Motion to Strike in Part the Sur-Reply of Health Grades, Inc., filed Aug. 2, 2011, 4 pages.
*Health Grades* vs. *MDX Medical, Inc.*, MDX Medical, Inc.'s Unopposed Motion for Extension of Time to Serve Portions of Invalidity Contentions and Accompanying Documents, filed Aug. 18, 2011, 4 pages.
*Health Grades* vs. *MDX Medical, Inc.*, Parties' Joint Motion to Extend Deadlines to Exchange Proposed Terms for Construction and to Exchange Their Preliminary Claim Constructions and Extrinsic Evidence, filed Sep. 2, 2011, 5 pages.
*Health Grades* vs. *MDX Medical, Inc.*, Parties' Joint Claim Construction and Prehearing Statement, filed Oct. 19, 2011, 40 pages.
*Health Grades* vs. *MDX Medical, Inc.*, Health Grades, Inc.'s Response in Opposition to MDX Medical, Inc.'s Motion Pursuant to Federal Rule of Civil Procedure 16(B)(4) to Modify Scheduling Order and Rule 15(A)(2) for Leave to Amend Answer, filed Nov. 14, 2011, 78 pages.
*Health Grades* vs. *MDX Medical, Inc.*, MDX Medical, Inc.'s Motion to Strike Plaintiff/Counterclaim Defendant Health Grades, Inc.'s Supplemental Infringement Contentions Pursuant to Fed. R. Civ. P. 16(f) and Fed. R. Civ. P. 37(b)(2)(A), filed Nov. 15, 2011, 304 pages.
*Health Grades* vs. *MDX Medical, Inc.*, MDX Medical, Inc.'s Motion to Compel Discovery and for an Award of Fees and Costs Pursuant to Rules 37(a)(3)(B) and 37(a)(5) of the Federal Rules of Civil Procedure, filed Nov. 23, 2011, 206 pages.
*Health Grades* vs. *MDX Medical, Inc.*, Health Grades, Inc.'s Response in Opposition to MDX Medical, Inc.'s Motion to Strike Plaintiff/Counterclaim Defendant Health Grades, Inc.'s Supplemental Infringement Contentions Pursuant to Fed. R. Civ. P. 16(f) and Fed. R. Civ. P. 37(b)(2)(A) and Motion to Allow Supplemental Infringement Contentions, filed Nov. 29, 2011, 9 pages.
*Health Grades* vs. *MDX Medical, Inc.*, Health Grades, Inc.'s Motion for Leave to File Its Supplemental Response to MDX Medical, Inc.'s Motion to Strike Health Grades, Inc.'s Supplemental Infringement Contentions, filed Dec. 2, 2011, 5 pages.

*Health Grades* vs. *MDX Medical, Inc.*, Health Grades, Inc.'s Supplemental Response to MDX Medical, Inc.'s Motion to Strike Health Grades, Inc.'s Supplemental Infringement Contentions, filed Dec. 2, 2011, 6 pages.
*Health Grades* vs. *MDX Medical, Inc.*, MDX Medical, Inc.'s Amended Answer, Affirmative Defenses, Counterclaim and Demand for Jury Trial, filed Dec. 5, 2011, 15 pages.
*Health Grades* vs. *MDX Medical, Inc.*, MDX Medical, Inc.'s Response in Opposition to Health Grades, Inc.'s Motion for Leave to File Its Supplemental Response to MDX's Motion to Strike Health Grades' Supplemental Infringement Contentions, filed Dec. 5, 2011, 47 pages.
*Health Grades* vs. *MDX Medical, Inc.*, Health Grades, Inc.'s Claim Construction Brief and Evidence, filed Dec. 5, 2011, 30 pages.
*Health Grades* vs. *MDX Medical, Inc.*, Health Grades, Inc.'s Supplement to Its Certificate of Conferral in Its Motion for Leave to File Its Supplemental Response to MDX Medical, Inc.'s Motion to Strike Health Grades, Inc.s Supplemental Infringement Contentions, filed Dec. 5, 2011, 3 pages.
*Health Grades* vs. *MDX Medical, Inc.*, Parties' Joint and Agreed-to Motion to Modify Scheduling Order and Extend Fact Discovery Cut-Off, Expert Reports Deadline and Expert Discovery Cut-Off, filed Dec. 9, 2011, 5 pages.
*Health Grades* vs. *MDX Medical, Inc.*, Recommendation of United States Magistrate Judge, filed Dec. 12, 2011, 11 pages.
*Health Grades* vs. *MDX Medical, Inc.*, Health Grades, Inc.'s Response to MDX Medical, Inc.'s Motion to Compel Discovery and for an Award of Fees and Costs Pursuant to Rules 37(A)(3)(B) and 37(A)(5) of the Federal Rules of Civil Procedure, filed Dec. 12, 2011, 69 pages.
[DKT 057] *Health Grades* vs. *MDX Medical, Inc.*, MDX Medical, Inc.'s Motion Pursuant to Federal Rule of Civil Procedure 16(B)(4) to Modify Scheduling Order and Rule 15(A)(2) for Leave to Amend Answer, filed Oct. 28, 2011, 55 pages.
[DKT 093] *Health Grades* vs. *MDX Medical, Inc.*, MDX Medical, Inc.'s Claim Construction Response and Evidence, filed Dec. 19, 2011 (27 pages).
[DKT 097] *Health Grades* vs. *MDX Medical, Inc.*, MDX Medical, Inc.'s Motion for Leave to Amend Invalidity Contentions, filed Dec. 21, 2011 (90 pages).
[DKT 102] *Health Grades* vs. *MDX Medical, Inc.*, Plaintiff's Objections to the Magistrate Judge's Recommendation, filed Dec. 27, 2011 (243 pages).
[DKT 106] *Health Grades* vs. *MDX Medical, Inc.*, Health Grades, Inc.'s Claim Construction Reply and Evidence, filed Dec. 28, 2011 (14 pages).
[DKT 108] *Health Grades* vs. *MDX Medical, Inc.*, MDX Medical, Inc.'s Response to Objections to Magistrate Judge's Recommendation, filed Jan. 9, 2012 (16 pages).
[DKT 111] *Health Grades* vs. *MDX Medical, Inc.*, Health Grades, Inc.'s Response to MDX Medical, Inc.'s Motion for Leave to Amend Invalidity Contentions [97], filed Jan. 11, 2012 (133 pages).
[DKT 112] *Health Grades* vs. *MDX Medical, Inc.*, MDX Medical, Inc.'s Motion to Supplement its Claim Construction Response and Evidence, filed Jan. 17, 2012 (10 pages).
[DKT 115] *Health Grades* vs. *MDX Medical, Inc.*, MDX Medical, Inc.'s Markman Hearing Exhibit List, filed Jan. 17, 2012 (5 pages).
[DKT 118] *Health Grades* vs. *MDX Medical, Inc.*, Health Grades, Inc.'s Hearing Exhibit List, filed Jan. 18, 2012 (6 pages).
[DKT 119] *Health Grades* vs. *MDX Medical, Inc.*, Plaintiff's Brief in Opposition to Defendant's Motion to Supplement its Claim Construction Response and Evidence, filed Jan. 18, 2012 (6 pages).
[DKT 122] *Health Grades* vs. *MDX Medical, Inc.*, MDX Medical, Inc.'s Notice of Supplemental Submission to its Motion for Leave to Amend Invalidity Contentions, filed Jan. 23, 2012 (58 pages).
[DKT 131] *Health Grades* vs. *MDX Medical, Inc.*, Plaintiff's Reply in Support of its Objections to the Magistrate Judge's Recommendation, filed Jan. 26, 2012 (14 pages).
[DKT 135] *Health Grades* vs. *MDX Medical, Inc.*, MDX Medical, Inc.'s Response in Opposition to Health Grades, Inc.'s Motion to Compel Discovery and for an Award of Fees and Costs; and Request for an Award of Fees and Costs to MDX Medical, Inc., filed Feb. 8, 2012, 98 pages.

(56) References Cited

OTHER PUBLICATIONS

[DKT 138] *Health Grades* vs. *MDX Medical, Inc.*, Order Regarding Claim Construction, filed Feb. 13, 2012 (24 pages).
[DKT 139] *Health Grades* vs. *MDX Medical, Inc.*, MDX Medical, Inc.'s Motion for Reconsideration of Motion for Partial Summary Judgment of No Infringement, filed Feb. 14, 2012 (25 pages).
[DKT 140] *Health Grades* vs. *MDX Medical, Inc.*, Health Grades, Inc.'s Reply in Support of its Motion to Compel Discovery and for an Award of Fees and Costs Pursuant to Local Patent Rule 3-3 and Rules 37(a)(3)(B) and 37(a)(5) of the Federal Rules of Civil Procedure, filed Feb. 21, 2012 (52 pages).
[DKT 141] *Health Grades* vs. *MDX Medical, Inc.*, MDX Medical, Inc.'s Unopposed Motion Pursuant to Federal Rule of Civil Procedure 16(B)(4) to Modify Scheduling Order and Rule 15(A)(2) to File Second Amended Answer, filed Feb. 24, 2012 (41 pages).
[DKT 148] *Health Grades* vs. *MDX Medical, Inc.*, Health Grades, Inc.'s Motion for Leave to Amend its Infringement Contentions to Address New Claim Construction from the Feb. 13, 2012 Markman Order, filed Mar. 2, 2012 (524 pages).
[DKT 156] *Health Grades* vs. *MDX Medical, Inc.*, Health Grades, Inc.'s Response in Opposition to MDX's Motion for Reconsideration of Motion for Partial Summary Judgment of No Infringement, filed Mar. 9, 2012 (273 pages).
[DKT 164] *Health Grades* vs. *MDX Medical, Inc.*, MDX Medical, Inc.'s Opposition to Health Grades Motion for Leave to Amend its Infringement Contentions, filed Mar. 23, 2012 (158 pages).
[DKT 168] *Health Grades* vs. *MDX Medical, Inc.*, MDX Medical, Inc.'s Reply Memorandum in Support of Its Motion for Reconsideration of Motion for Partial Summary Judgment of the Non-Infringement, filed Mar. 26, 2012, 16 pages.
[DKT 169] *Health Grades* vs. *MDX Medical, Inc.*, Exhibits in Support of MDX Medical, Inc.'s Reply Memorandum in Support of its Motion for Reconsideration of Motion for Partial Summary Judgment of Non-Infringement, filed Mar. 26, 2012 (70 pages).
[DKT 173] *Health Grades* vs. *MDX Medical, Inc.*, Health Grades, Inc.'s Reply in Support of its Motion for Leave to Amend its Infringement Contentions, filed Apr. 6, 2012 (55 pages).
[DKT 183] *Health Grades* vs. *MDX Medical, Inc.*, MDX Medical, Inc.'s Second Amended Answer, Affirmative Defenses, Counterclaim and Demand for Jury Trial, filed Apr. 18, 2012 (16 pages).
[DKT 189] *Health Grades* vs. *MDX Medical, Inc.*, Health Grade, Inc.'s Motion to Compel Discovery and for an Award of Fees and Costs Pursuant to Rules 36(a)(6), 37(a)(3)(B) and 37(a)(5) of the Federal Rules of Civil Procedure, filed Apr. 25, 2012 (62 pages).
[DKT 195] *Health Grades* vs. *MDX Medical, Inc.*, MDX Medical, Inc.'s Second Motion Pursuant to Federal Rule of Civil Procedure 56 for Partial Summary Judgment of Non-Infringement, filed May 8, 2012 (192 pages).
[DKT 199] *Health Grades* vs. *MDX Medical, Inc.*, MDX Medical, Inc.'s Opposition to Health Grades' Motion to Compel Discovery and for an Award of Fees, filed May 21, 2012 (6 pages).
[DKT 201] *Health Grades* vs. *MDX Medical, Inc.*, Health Grades, Inc.'s Response to MDX's Second Motion Pursuant to Federal Rule of Civil Procedure 56 Partial Summary Judgment of Non-Infringement, filed Jun. 1, 2012, 465 pages.
[DKT 207] *Health Grades* vs. *MDX Medical, Inc.*, MDX Medical, Inc.'s Reply Memorandum in Support of its Second Motion for Summary Judgment, field Jun. 8, 2012 (15 pages).
[DKT 212] *Health Grades* vs. *MDX Medical, Inc.*, Health Grades, Inc.'s Reply in Support of its Motion to Compel Discovery and for an Award of Fees and Costs Pursuant to Rules 36(a)(6), 37(a)(3)(B) and 37(a)(5) of the Federal Rules of Civil Procedure, filed Jun. 11, 2012 (159 pages).
[DKT 215] *Health Grades* vs. *MDX Medical, Inc.*, Health Grades, Inc.'s Motion to Strike a New Invalidity Argument in MDX Medical, Inc.'s Third Supplemental Invalidity Contentions, filed Jun. 15, 2012 (195 pages).
[DKT 235] *Health Grades* vs. *MDX Medical, Inc.*, Health Grades, Inc.'s Supplemental Response to MDX's Second Motion Pursuant to Federal Rules of Civil Procedure 56 for Partial Summary Judgment of Non-Infringement, filed Jul. 3, 2012 (3 pages).
[DKT 243] *Health Grades* vs. *MDX Medical, Inc.*, MDX Medical, Inc.'s Opposition to Health Grades Motion to Strike Invalidity Argument in MDX Medical, Inc.'s Third Supplemental Invalidity Contentions, filed Jul. 6, 2012 (5 pages).
[DKT 247] *Health Grades* vs. *MDX Medical, Inc.*, MDX Medical, Inc.'s Unopposed Motion for Leave to File a Supplemental Reply in Support of Its Second Motion Pursuant to Federal Rule of Civil Procedure 56 for Partial Summary Judgment of Non-Infringement, filed Jul. 6, 2012, 3 pages.
[DKT 248] *Health Grades* vs. *MDX Medical, Inc.*, MDX Medical, Inc.'s Supplemental Reply in Support of Its Second Motion Pursuant to Federal Rule of Civil Procedure 56 for Partial Summary Judgment of Non-Infringement, filed Jul. 6, 2012, 4 pages.
[DKT 252] *Health Grades* vs. *MDX Medical, Inc.*, Health Grades, Inc.'s Motion for Leave to Amend Its Complaint to Assert Causes of Action for Joint Infringement and Indirect Infringement, filed Jul. 13, 2012, 104 pages.
[DKT 258] *Health Grades* vs. *MDX Medical, Inc.*, Health Grades, Inc.'s Reply in Support of Its Motion to Strike a New Invalidity Argument in MDX Medical, Inc.'s Third Supplemental Invalidity Contentions, filed Jul. 23, 2012 (54 pages).
[DKT 275] *Health Grades* vs. *MDX Medical, Inc.*, Parties' Joint Stipulated Motion for a 45 Day Extension to File Their Respective Motions to Supplement Contentions and for MDX to File Its Response to Health Grades' Motion for Leave to File Its First Amended Complaint, filed Aug. 2, 2012, 4 pages.
[DKT 293] *Health Grades* vs. *MDX Medical, Inc.*, MDX Medical, Inc.'s Second Motion for Leave to Amend Invalidity Contentions, filed Sep. 17, 2012, 10 pages.
[DKT 294] *Health Grades* vs. *MDX Medical, Inc.*, MDX Medical, Inc.'s Second Motion for Leave to Amend Invalidity Contentions, filed Sep. 17, 2012, 180 pages.
[DKT 295] *Health Grades* vs. *MDX Medical, Inc.*, MDX Medical, Inc.'s Opposition to Health Grades, Inc.'s Motion for Leave to Amend Its Complaint to Assert Causes of Action for Joint Infringement and Indirect Infringement, filed Sep. 17, 2012, 88 pages.
[DKT 309] *Health Grades* vs. *MDX Medical, Inc.*, MDX Medical, Inc.'s Opposition to Health Grades' Motion for Leave to Supplement its Response to MDX's Second Motion Pursuant to Federal Rule of Civil Procedure 56 for Partial Summary Judgment of Non-Infringement (Dkt. 195), filed Sep. 27, 2012, 8 pages.
[DKT 324] *Health Grades* vs. *MDX Medical, Inc.*, Plaintiff Health Grades, Inc.'s Response to Defendant MDX Medical, Inc.'s Second Motion for Leave to Amend Invalidity Contentions, filed Oct. 11, 2012, 5 pages.
[DKT 325] *Health Grades* vs. *MDX Medical, Inc.*, MDX Medical, Inc.'s Opposition to Health Grades' Motion for Leave to Amend Its Infringement Contentions to Incorporate Dr. Philip Greenspun's Expert Report, filed Oct. 11, 2012, 28 pages.
[DKT 326] *Health Grades* vs. *MDX Medical, Inc.*, Exhibit A to MDX Medical, Inc.'s Opposition to Health Grades' Motion for Leave to Amend Its Infringement Contentions to Incorporate Dr. Philip Greensun's Expert Report, filed Oct. 11, 2012, 4 pages.
[DKT 329] *Health Grades* vs. *MDX Medical, Inc.*, Health Grades, Inc.'s Reply in Support of Its Motion for Leave to Amend Its Complaint to Assert Causes of Action for Joint Infringement and Indirect Infringement, filed Oct. 12, 2012, 16 pages.
[DKT 331] *Health Grades* vs. *MDX Medical, Inc.*, Health Grades, Inc.'s Reply in Support of Its Motion for Leave to Supplement Its Response to MDX's Second Motion Pursuant to Federal Rule of Civil Procedure 56 for Partial Summary Judgment of Non-Infringement, filed Oct. 15, 2012, 9 pages.
[DKT 338] *Health Grades* vs. *MDX Medical, Inc.*, Health Grades, Inc.'s Motion to Partially Exclude Expert Testimony of Dr. Richard G. Cooper Pursuant to Fed.R.Evid. 403 and 702, and *Daubert* v *Merril Dow Pharms, Inc.*, 509 U.S. 579 (1993), filed Oct. 22, 2012, 140 pages.
[DKT 349] *Health Grades* vs. *MDX Medical, Inc.*, MDX Medical, Inc.'s Motion to Preclude Any Testimony from Health Grades, Inc.'s Expert Dr. Greespun, filed Oct. 25, 2012, 100 pages.

(56) References Cited

OTHER PUBLICATIONS

[DKT 355] *Health Grades* vs. *MDX Medical, Inc.*, MDX Medical, Inc.'s Reply Memorandum in Support of its Motion for Leave to Amend its Invalidity Contentions [Doc. # 293], filed Oct. 29, 2012, 3 pages.
[DKT 357] *Health Grades* vs. *MDX Medical, Inc.*, Health Grades, Inc.'s Reply in Support of its Motion for Leave to Amend its Infringement Contentions (Dkt. 292), filed Oct. 29, 2012, 11 pages.
[DKT 361] *Health Grades* vs. *MDX Medical, Inc.*, Health Grades, Inc.'s Unopposed Motion for Leave to Supplement its Motion to Partially Exclude Expert Testimony of Dr. Richard G. Cooper (Dkt. 338), filed Oct. 30, 2012, 3 pages.
[DKT 362] *Health Grades* vs. *MDX Medical, Inc.*, Health Grades, Inc.'s Supplement to its Motion to Partially Exclude Expert Testimony of Dr. Richard G. Cooper Pursuant to Fed. R. Evid. 403 and 702, and *Daubert* v. *Merril Dow Pharms., Inc.*, 509 U.S. 579 (1993), filed Oct. 30, 2012, 3 pages.
[DKT 367] *Health Grades* vs. *MDX Medical, Inc.*, MDX Medical, Inc.'s Motion Pursuant to Federal Rule of Civil Procedure 56 for Summary Judgment of Non-Infringement, filed Nov. 2, 2012, 67 pages.
[DKT 368] *Health Grades* vs. *MDX Medical, Inc.*, MDX Medical, Inc.'s Motion Pursuant to Federal Rule of Civil Procedure 56 for Summary Judgment of Non-Infringement, filed Nov. 2, 2012, 9 pages.
[DKT 369] *Health Grades* vs. *MDX Medical, Inc.*, Health Grades, Inc.'s Motion for Partial Summary Judgment, filed Nov. 2, 2012, 241 pages.
[DKT 370] *Health Grades* vs. *MDX Medical, Inc.*, MDX Medical, Inc.'s Motion Pursuant to Federal Rule of Civil Procedure 56 for Summary Judgment of No Willfulness, filed Nov. 2, 2012, 89 pages.
[DKT 371] *Health Grades* vs. *MDX Medical, Inc.*, MDX Medical, Inc.'s Motion Pursuant to Federal rule of Civil Procedure 56 for Summary Judgment of No Willfulness, filed Nov. 2, 2012, 14 pages.
[DKT 392] *Health Grades* vs. *MDX Medical, Inc.*, Health Grades, Inc.'s Opposition to MDX Medical's Motion to Preclude Any Testimony from Health Grades, Inc.'s Expert Dr. Greenspun, filed Nov. 19, 2012, 248 pages.
[DKT 404] *Health Grades* vs. *MDX Medical, Inc.*, Health Grades, Inc.'s Opposition to MDX Medical, Inc.'s Motion for Summary Judgment of No Willfulness, filed Nov. 26, 2012, 79 pages.
[DKT 405] *Health Grades* vs. *MDX Medical, Inc.*, Health Grades, Inc.'s Opposition to MDX Medical, Inc.'s Motion for Summary Judgment of Non-Infringement, filed Nov. 26, 2012, 39 pages.
[DKT 406] *Health Grades* vs. *MDX Medical, Inc.*, MDX Medical, Inc.'s Opposition to Health Grades, Inc.'s Motion for Partial Summary Judgment, filed Nov. 26, 2012, 200 pages.
[DKT 407] *Health Grades* vs. *MDX Medical, Inc.*, MDX Medical, Inc.'s Opposition to Health Grades, Inc.'s Motion for Partial Summary Judgment, filed Nov. 26, 2012, 300 pages.
[DKT 436] *Health Grades* vs. *MDX Medical, Inc.*, MDX Medical, Inc.'s Reply in Support of its Motion to Preclude any Testimony from Health Grades, Inc.'s Expert Dr. Greenspun, filed Dec. 6, 2012, 9 pages.
[DKT 442] *Health Grades* vs. *MDX Medical, Inc.*, Health Grades, Inc.'s Reply in Support of Its Motion for Partial Summary Judgment, filed Dec. 13, 2012, 93 pages.
[DKT 443] *Health Grades* vs. *MDX Medical, Inc.*, MDX Medical, Inc.'s Reply in Support of its Motion Pursuant to Federal Rule of Civil Procedure 56 for Summary Judgment of No Willfulness, filed Dec. 13, 2012, 45 pages.
[DKT 444] *Health Grades* vs. *MDX Medical, Inc.*, MDX Medical, Inc.'s Reply in Support of Its Motion Pursuant to Federal Rule of Civil Procedure 56 for Summary Judgment of Non-Infringement, filed Dec. 13, 2012, 35 pages.
[DKT 477] *Health Grades* vs. *MDX Medical, Inc.*, Order, filed Jan. 10, 2013, 10 pages.
[DKT 485] *Health Grades* vs. *MDX Medical, Inc.*, MDX Medical, Inc.'s Unopposed Motion to Extend the Dispositive Motion Deadline in Light of the Court's Order Granting Health Grades, Inc.'s Motion for Leave to Amend Its Complaint, filed Jan. 18, 2013, 145 pages.
[DKT 500] *Health Grades* vs. *MDX Medical, Inc.*, MDX Medical, Inc.'s Answer to First Amended Complaint, Affirmative Defenses, Counterclaim and Demand for Jury Trial, filed Jan. 28, 2013, 18 pages.
[DKT 515] *Health Grades* vs. *MDX Medical, Inc.*, Second Amended Complaint and Demand for Jury Trial, filed Feb. 12, 2013, 7 pages.
[DKT 525] *Health Grades* vs. *MDX Medical, Inc.*, Health Grades, Inc.'s Opposition to MDX Medical, Inc.'s Motion for Summary Judgment of No Infringement with Regard to Amended Complaint and Allegations Relating to Aetna Life Insurance Company, filed Feb. 20, 2013, 87 pages.
[DKT 532] *Health Grades* vs. *MDX Medical, Inc.*, MDX Medical, Inc.'s Answer to Second Amended Complaint, Affirmative Defenses, Counterclaim and Demand for Jury Trial, filed Mar. 1, 2013, 18 pages.
[DKT 562] *Health Grades* vs. *MDX Medical, Inc.*, Health Grades, Inc.'s Supplement to Its Opposition to MDX Medical, Inc.'s Motion Pursuant to Federal Rule of Civil Procedure 56 for Summary Judgment of No Willfulness, filed Apr. 16, 2013, 176 pages.
[DKT 564] *Health Grades* vs. *MDX Medical, Inc.*, MDX Medical, Inc.'s Motion for Rule 11 Sanctions, filed Apr. 24, 2013, 57 pages.
[DKT 565] *Health Grades* vs. *MDX Medical, Inc.*, Exhibits in Support of Motion for Rule 11 Sanctions by Defendant MDX Medical, Inc., filed Apr. 24, 2013, 159 pages.
[DKT 575] *Health Grades* vs. *MDX Medical, Inc.*, MDX Medical, Inc.'s Motion to Compel, filed May 1, 2013, 39 pages.
[DKT 592] *Health Grades* vs. *MDX Medical, Inc.*, Health Grades, Inc.'s Opposition to MDX Medical, Inc.'s Motion to Compel, filed May 22, 2013, 89 pages.
[DKT 598] *Health Grades* vs. *MDX Medical, Inc.*, Health Grades, Inc.'s Motion to Bifurcate Trial on the Issue of Inequitable Conduct, filed Jun. 4, 2013, 14 pages.
[DKT 601] *Health Grades* vs. *MDX Medical, Inc.*, MDX Medical, Inc.'s Reply Memorandum in Support of its Motion for Rule 11 Sanctions, filed Jun. 6, 2013, 19 pages.
[DKT 605] *Health Grades* vs. *MDX Medical, Inc.*, MDX Medical, Inc.'s Opposition to Health Grades, Inc.'s Motion to Bifurcate Trial on the Issue of Inequitable Conduct, filed Jun. 28, 2013, 154 pages.
[DKT 608] *Health Grades* vs. *MDX Medical, Inc.*, Health Grades, Inc.'s Reply in Support of Its Motion to Bifurcate Trial on the Issue of Inequitable Conduct, filed Jul. 15, 2013, 1 page.
[DKT 609] *Health Grades* vs. *MDX Medical, Inc.*, Health Grades, Inc.'s Reply in Support of Its Motion to Bifurcate Trial on the Issue of Inequitable Conduct, filed Jul. 15, 2013, 12 pages.
[HG Trial Exhibit No. 304] *Health Grades* vs. *MDX Medical, Inc.*, Health Grades, Inc.'s Disclosure of Asserted Claims and Infringement Contentions, dated Jul. 1, 2011, 5 pags.
[HG Trial Exhibit No. 305] *Health Grades* vs. *MDX Medical, Inc.*, Plaintiff Health Grades' Rule 3.1(c) Disclosure—Exhibit A—'060 Patent v. MDx's Current Website, dated Jul. 1, 2011, 59 pages.
[HG Trial Exhibit No. 306] *Health Grades* vs. *MDX Medical, Inc.*, Plaintiff Health Grades' Rule 3.1(c) Disclosure—Exhibit C, dated Jul. 1, 2011, 54 pages.
[HG Trial Exhibit No. 307] *Health Grades* vs. *MDX Medical, Inc.*, Plaintiff Health Grades' Rule 3.1(c) Disclosure—Exhibit B—'060 Patent v. MDx's Previous Website, dated Jul. 1, 2011, 56 pages.
[HG Trial Exhibit No. 308] *Health Grades* vs. *MDX Medical, Inc.*, Plaintiff Health Grades' Rule 3.1(c) Disclosure—Exhibit D, dated Jul. 1, 2011, 51 pages.
[HG Trial Exhibit No. 309] *Health Grades* vs. *MDX Medical, Inc.*, Plaintiff Health Grades' Feb. 2012 Supplemental to its Rule 3.1(c) Disclosure—'060 Patent v. MDx's Current Website, dated Feb. 2012, 123 pages.
[HG Trial Exhibit No. 310] *Health Grades* vs. *MDX Medical, Inc.*, Plaintiff's Health Grades' Feb. 2012 Supplement to its Rule 3.1(c) Disclosure—'060 Patent v. MDx's Previous Website, Feb. 2012, 64 pages.
[HG Trial Exhibit No. 311] *Health Grades* vs. *MDX Medical, Inc.*, Health Grades, Inc.'s Supplemental Disclosure of Asserted claims and Infringement Contentions, dated Jul. 19, 2011, 41 pages.

(56) References Cited

OTHER PUBLICATIONS

[HG Trial Exhibit No. 313] *Health Grades* vs. *MDX Medical, Inc.*, Declaration of Kirstin Stoll-DeBell in Support of Health Grades, Inc.'s Response to MDx's Second Motion for Partial Summary Judgment of Noninfringement, dated Jun. 1, 2012, 50 pages.
[HG Trial Exhibit No. 314] *Health Grades* vs. *MDX Medical, Inc.*, Declaration of Kirstin Stoll-DeBell in Support of Health Grades, Inc.'s Response in Opposition to MDx's Motion for Reconsideration of Motion for Partial Summary Judgment of No Infringement, dated Mar. 9, 2012, 49 pages.
[HG Trial Exhibit No. 315] *Health Grades* vs. *MDX Medical, Inc.*, Plaintiff Health Grades, Inc.'s Responses to Defendant MDX Medical, Inc.'s First Set of Interrogatories (Nos. 1-6), dated Jul. 20, 2011, 38 pages.
[HG Trial Exhibit No. 316] *Health Grades* vs. *MDX Medical, Inc.*, Plaintiff Health Grades, Inc.'s Supplemental Responses to Defendant MDX Medical, Inc.'s Interrogatory Nos. 8 and 9, dated Dec. 10, 2011, 25 pages.
[HG Trial Exhibit No. 317] *Health Grades* vs. *MDX Medical, Inc.*, Plaintiff Health Grades, Inc.'s Second Supplemental Response to Defendant MDX Medical, Inc.'s Interrogatory No. 8, Jan. 26, 2012, 45 pages.
[HG Trial Exhibit No. 318] *Health Grades* vs. *MDX Medical, Inc.*, Plaintiff Health Grades, Inc.'s Supplemental Responses to Defendant MDX Medical, Inc.'s Interrogatory Nos. 1 and 3, dated Dec. 30, 2011, 11 pages.
[HG Trial Exhibit No. 319] *Health Grades* vs. *MDX Medical, Inc.*, Plaintiff Health Grades, Inc.'s supplemental Response to Defendant MDX Medical, Inc.'s Interrogatory No. 6, dated Jan. 23, 2012, 12 pages.
[HG Trial Exhibit No. 321] *Health Grades* vs. *MDX Medical, Inc.*, Plaintiff Health Grades, Inc.'s Response to MDX Medical, Inc.'s Third Set of Interrogatories (No. 10), dated Dec. 10, 2011, 8 pages.
[HG Trial Exhibit No. 322] *Health Grades* vs. *MDX Medical, Inc.*, Plaintiff Health Grades, Inc.'s Responses to Defendant MDX Medical, Inc.'s Second Set of Requests for Production of Documents and Things (Nos. 19-25), dated Oct. 20, 2011, 11 pages.
[HG Trial Exhibit No. 323] *Health Grades* vs. *MDX Medical, Inc.*, Plaintiff Health Grades, Inc.'s Supplemental Response to Defendant MDX Medical, Inc.'s Request for Production No. 1, dated Aug. 23, 2012, 17 pages.
[HG Trial Exhibit No. 327] *Health Grades* vs. *MDX Medical, Inc.*, Defendant MDX Medical, Inc.'s Supplemental Objections and Responses to Plaintiff's First Set of Interrogatories, dated Feb. 15, 2012, 7 pages.
[HG Trial Exhibit No. 329] *Health Grades* vs. *MDX Medical, Inc.*, Defendant MDX Medical, Inc.'s Objection and Responses to Plaintiff's First Set of Requests for Admission and Second Set of Interrogatories, dated Feb. 15, 2012, 25 pages.
[HG Trial Exhibit No. 330] *Health Grades* vs. *MDX Medical, Inc.*, Defendant MDX Medical, Inc.'s Supplemental Objections and Responses to Plaintiff's first Set of Requests for Admission, dated Jun. 4, 2012, 5 pages.
[HG Trial Exhibit No. 331] *Health Grades* vs. *MDX Medical, Inc.*, Defendant MDX Medical, Inc.'s Second Supplemental Objections and Responses to Plaintiff's First Set of Requests for Admission, dated Sep. 21, 2012, 16 pages.
[HG Trial Exhibit No. 332] *Health Grades* vs. *MDX Medical, Inc.*, MDX Medical Inc.'s Objection and Responses to Plaintiff's First Request for the Production of Documents, Electronically Stored Information, and Tangible Things, dated Aug. 29, 2011, 23 pages.
[MDX Trial Exhibit No. A-17] *Health Grades* vs. *MDX Medical, Inc.*, MDX Medical, Inc.'s Third Supplemental Invalidity Contentions and Documents Accompanying Invalidity Contentions, date May 10, 2012, 58 pages.
[MDX Trial Exhibit No. A-18] *Health Grades* vs. *MDX Medical, Inc.*, MDX Medical, Inc.'s Fourth Supplemental Invalidity Contentions and Documents Accompanying Invalidity Contentions, dated Sep. 17, 2012, 60 pages.

*Health Grades* vs. *MDX Medical, Inc.*, Declaration of Richard G. Cooper, D.Sc., dated Jul. 13, 2012, 57 pages.
*Health Grades* vs. *MDX Medical, Inc.*, Defendant MDX Medical, Inc.'s First Set of Requests for Admission (Nos. 1-3), dated Sep. 7, 2011, 5 pages.
*Health Grades* vs. *MDX Medical, Inc.*, Defendant MDX Medical, Inc.'s Objections and Responses to Plaintiff's First Set of Interrogatories, dated Aug. 29, 2011, 22 pages.
*Health Grades* vs. *MDX Medical, Inc.*, Expert Report of Philip Greenspun, dated Jul. 13, 2012, 394 pages.
*Health Grades* vs. *MDX Medical, Inc.*, MDX Medical, Inc.'s First Set of Interrogatories (Nos. 1-6), dated Jun. 8, 2011, 10 pages.
*Health Grades* vs. *MDX Medical, Inc.*, MDX Medical, Inc.'s Second Set of Interrogatories (Nos. 7-9), dated Sep. 7, 2011, 4 pages.
*Health Grades* vs. *MDX Medical, Inc.*, MDX Medical, Inc.'s Third Set of Interrogatories (No. 10), dated Nov. 2, 2011, 4 pages.
*Health Grades* vs. *MDX Medical, Inc.*, Plaintiff Health Grades, Inc.'s First Set of Interrogatories to Defendant MDX Medical, Inc. d/b/a Vitals.com, dated Jul. 25, 2011, 15 pages.
*Health Grades* vs. *MDX Medical, Inc.*, Plaintiff Health Grades, Inc.'s Answers to Defendant MDX Medical, Inc.'s First Set of Requests for Admission (Nos. 1-3), dated Oct. 20, 2011, 4 pages.
*Health Grades* vs. *MDX Medical, Inc.*, Plaintiff Health Grades, Inc.'s Responses to Defendant MDX Medical, Inc.'s First Set of Interrogatories (Nos. 1-6), dated Jul. 20, 2011, 20 pages.
*Health Grades* vs. *MDX Medical, Inc.*, Plaintiff Health Grades, Inc.'s Responses to Defendant MDX Medical, Inc.'s Second Set of Interrogatories (Nos. 7-9), dated Oct. 20, 2011, 8 pages.
*Health Grades* vs. *MDX Medical, Inc.*, Plaintiff Health Grades, Inc.'s Supplemental Answers to Defendant MDX Medical, Inc.'s Requests for Admission Nos. 1 and 2, dated Nov. 9, 2011, 4 pages.
*Health Grades* vs. *MDX Medical, Inc.*, Rebuttal Report of Philip Greenspun, dated Sep. 17, 2012, 105 pages.
*Health Grades* vs. *MDX Medical, Inc.*, Rebuttal Report of Richard G. Cooper, D.Sc., dated Sep. 17, 2012, 13 pages.
US Amendment filed Feb. 11, 2013, in U.S. Appl. No. 12/830,255, 19 pages.
US Amendment filed Feb. 27, 2012, in U.S. Appl. No. 12/613,822 (22 pages).
US Amendment filed Sep. 4, 2012, in U.S. Appl. No. 12/897,599 (10 pages).
US Amendment filed Sep. 6, 2012, in U.S. Appl. No. 12/830,255 (17 pages).
US Amendment filed Dec. 13, 2012, in U.S. Appl. No. 12/613,822 (23 pages).
US Final Office Action mailed Jul. 13, 2012, in U.S. Appl. No. 12/613,822 (31 pages).
US Final Office Action mailed Oct. 11, 2012, in U.S. Appl. No. 12/830,255 (19 pages).
US Final Office Action mailed Oct. 24, 2012, in U.S. Appl. No. 12/897,599 (21 pages).
US Non-Final Office Action mailed Apr. 6, 2012, in U.S. Appl. No. 12/830,255 (17 pages).
US Non-Final Office Action mailed May 1, 2012, in U.S. Appl. No. 12/897,599 (8 pages).
US Non-Final Rejection mailed Apr. 5, 2013, in U.S. Appl. No. 13/551,471, 26 pages.
[DKT 269-1] *Health Grades* vs. *MDX Medical, Inc.*, MDX Medical, Inc.'s Unopposed Motion to Restrict Access to Document—Document Nos. 252, 253, 253-2, 253-3, 253-4 and 253-5—Exhibit A, filed Jul. 27, 2012, 19 pages.
[DKT 322-7] *Health Grades* vs. *MDX Medical, Inc.*, MDX Medical, Inc.'s Motion for Leave to Restrict Access to Document—Document Nos. 292, 292-1, 292-8, 292-10, 292-12, 292-14, and 305-1—Exhibit 7 / Exhibit F, filed Oct. 10, 2012, 77 pages.
[DKT 353-1] *Health Grades* vs. *MDX Medical, Inc.*, MDX Medical, Inc.'s Motion for Leave to Restrict Access to Document—Document Nos. 329, 329-1 and 329-3—Exhibit 1 / Exhibit A, filed Oct. 26, 2012, 13 pages.
[DKT 353-2] *Health Grades* vs. *MDX Medical, Inc.*, MDX Medical, Inc.'s Motion for Leave to Restrict Access to Document—Document Nos. 329, 329-1 and 329-3—Exhibit 2 / Exhibit B, filed Oct. 26, 2012, 12 pages.

(56) References Cited

OTHER PUBLICATIONS

[DKT 400-1] *Health Grades* vs. *MDX Medical, Inc.*, MDX Medical, Inc.'s Unopposed Motion for Leave to Restrict Access to Documents—Document Nos. 368, 368-2, 371-1, 372-2, 375-1, 375-2 and 369-23—Exhibit 1 / Exhibit A, filed Nov. 21, 2012, 13 pages.
[DKT 459-1] *Health Grades* vs. *MDX Medical, Inc.*, Parties' Joint Unopposed Motion for Leave to Restrict Access to Documents—Document Nos. 404, 404-3, 404-4, 404-5, 404-6, 404-9, 404-1-, 405, 405-3, 405-4, 405-5, 405-6, 405-9, 411-1, 411-2, 411-3, 411-5, 412-1, 412-2, 412-4 & 433-5—Exhibit 1 / Exhibit A, filed Dec. 20, 2012, 19 pages.
[DKT 459-5] *Health Grades* vs. *MDX Medical, Inc.*, Parties' Joint Unopposed Motion for Leave to Restrict Access to Documents—Document Nos. 404, 404-3, 404-4, 404-5, 404-6, 404-9, 404-1-, 405, 405-3, 405-4, 405-5, 405-6, 405-9, 411-1, 411-2, 411-3, 411-5, 412-1, 412-2, 412-4 & 433-5—Exhibit 5 / Exhibit E, filed Dec. 20, 2012, 18 pages.
[DKT 506-1] *Health Grades* vs. *MDX Medical, Inc.*, MDX's Unopposed Motion for Leave to Restrict Access to Documents—Document Nos. 486-1 and 486-2—Exhibit 1 / Exhibit A, filed Feb. 1, 2013, 113 pages.
[DKT 551-1] *Health Grades* vs. *MDX Medical, Inc.*, MDX Medical, Inc.'s [Unopposed] Motion for Leave to Restrict Access to Documents 524, 524-1 Through 524-25 and 525; 525; 525-4; 525-5; 525-6/7/8; 525-11; 525-15; 525-18; 525-24; and 525-25—Exhibit 1 / Exhibit A, filed Mar. 14, 2013, 32 pages.
[DKT 554-1] *Health Grades* vs. *MDX Medical, Inc.*, MDX Medical, Inc.'s Unopposed Motion for Leave to Restrict Access to Document 547—Exhibit 1 / Exhibit A, filed Mar. 25, 2013, 4 pages.
E-mail from Scott Stimpson to Jesus Vazquez and Kirstin Stoll-DeBell re: Health Grades Duty of Candor, dated Sep. 6, 2013, 2 pages.
Health Grades Press Release re: HealthGrades Enhances Physician Quality Reports for Consumers, dated Aug. 2, 2005, 2 pages. [HG0001867-HG0001868].
Health Grades Nursing Home Quality Comparison Report, created Dec. 28, 2004, 15 pages. [HG0032037-HG0032051].
Health Grades Nursing Home Quality Report, created Dec. 28, 2004, 10 pages. [HG0032052-HG0032061].
Health Grades Physician Quality Comparison Report, created Dec. 28, 2004, 24 pages. [HG0032062-HG0032085].
Health Grades Physician Quality Report, created Dec. 28, 2004, 16 pages. [HG0032086-HG0032101].
Health Grades Hospital Quality Report, created Dec. 28, 2004, 8 pages. [HG0032102-HG0032109].
Health Grades Physician Quality Report for Consumers, dated Apr. 17, 2003, 11 pages. [HG208976-HG208986].
Health Grades Comparitive Physician Report, created Apr. 3, 2003, 14 pages. [HG208987-HG209000].
Health Grades website printout from www.healthgrades.com, dated Oct. 19, 2004, 2 pages. [UCHC0000079-UCHC0000080].
Health Grades website printout from www.healthgrades.com, dated Oct. 19, 2004, 1 page. [UCHC0000081].
Health Grades Hospital Quality Report, created Sep. 19, 2004, 9 pages. [UCHC0000082-UCHC0000090].
E-mail from Info@HealthGrades.com to kram1033@aol.com (Mark Donnelly) re: HealthGrades Report Receipt, dated Sep. 15, 2004, 17 pages. [UCHC0000094-UCHC0000110].
People Demand Credible and Reliable Healthcare Information. Subimo Helps You Provide it, Subimo at www.subimo.com, dated Oct. 19, 2004, 13 pages. [UCHC0000131-UCHC0000143].
HealthScope Home Page, from www.healthscope.com, dated Oct. 19, 2004, 5 pages. [UCHC0000202-UCHC0000206].
2004 Ingenix Tradeshow Calendar, from www.ingenix.com/corp_tradeshows.php, dated Nov. 7, 2004, 1 page. [UCHC0000309].
Printouts form www.Ingenix.com, dated Nov. 7, 2004, 13 pages. [UCHC0000276-UCHC0000288].
Printouts form www.Ingenix.com, dated Nov. 15, 2004, 1 page. [UCHC0000289].
GeoAccess Quality Ratings Suite, Ingenix, date not available, 8 pages. [UCHC0000290-UCHC0000297].
Printouts form www.Ingenix.com, dated Dec. 8, 2004, 4 pages. [UCHC0000303-UCHC0000306].
Ingenix Health Intellegence Update on HIPAA Privacy Complicance Program, Ingenix, dated Nov. 7, 2004, 2 pages. [UCHC0000301-UCHC0000302].
Preventing harm. Steering you from danger. Keeping you safe. Ingenix, Inc., dated Nov. 14, 2004, 2 pages. [UCHC0000307-UCHC0000308].
Patient Experience Survey Numbers, Oct. 28, 2004 to Nov. 9, 2004, 1 page. [HG209647].
HealthGrades Report on David A. Drucker, dated Jun. 4, 2005, 4 pages. [MGHG000016-MGHG000019].
[DKT 611] *Health Grades* vs. *MDX Medical, Inc.*, Exhibit A to MDX Medical, Inc.'s Partially Opposed Motion for Leave to Restrict Access to Documents—Document Nos. 611, 611-1, 611-2, 611-3 and 611-4, filed Oct. 9, 2013, 12 pages. [Redacted].
[DKT 611-1] *Health Grades* vs. *MDX Medical, Inc.*, Exhibit B to MDX Medical, Inc.'s Partially Opposed Motion for Leave to Restrict Access to Documents—Document Nos. 611, 611-1, 611-2, 611-3 and 611-4, filed Oct. 9, 2013, 134 pages. [Redacted].
[DKT 611-2] *Health Grades* vs. *MDX Medical, Inc.*, Exhibit C to MDX Medical, Inc.'s Partially Opposed Motion for Leave to Restrict Access to Documents—Document Nos. 611, 611-1, 611-2, 611-3 and 611-4, filed Oct. 9, 2013, 133 pages. [Redacted].
[DKT 611-3] *Health Grades* vs. *MDX Medical, Inc.*, Exhibit D to MDX Medical, Inc.'s Partially Opposed Motion for Leave to Restrict Access to Documents—Document Nos. 611, 611-1, 611-2, 611-3 and 611-4, filed Oct. 9, 2013, 3 pages. [Redacted].
[DKT 611-4] *Health Grades* vs. *MDX Medical, Inc.*, Exhibit E to MDX Medical, Inc.'s Partially Opposed Motion for Leave to Restrict Access to Documents—Document Nos. 611, 611-1, 611-2, 611-3 and 611-4, filed Oct. 9, 2013, 8 pages. [Redacted].
U.S. Appl. No. 13/551,471, Amendment and Response filed Sep. 5, 2013, 19 pages.
U.S. Appl. No. 13/551,471, Amendment and Response filed Sep. 23, 2013, 4 pages.
[DKT 612] *Health Grades* vs. *MDX Medical, Inc.*, Plaintiff Health Grades' Sep. 2013 Supplement to its Rule 3.1(c) Disclosure, filed Sep. 23, 2013, 326 pages.
[DKT 615-1] *Health Grades* vs. *MDX Medical, Inc.*, Exhibit A to MDX Medical, Inc.'s Unopposed Motion for Leave to Restrict Access to Document—Document No. 612-6, filed Sep. 26, 2013, 29 pages.
[DKT 618] *Health Grades* vs. *MDX Medical, Inc.*, Order Setting Hearing, filed Oct. 4, 2013, 2 pages.
[DKT 622] *Health Grades* vs. *MDX Medical, Inc.*, MDX Medical, Inc.'s Partially Opposed Motion for Leave to Restrict Access to Documents—Document Nos. 611, 611-1,611-2,611-3 and 611-4, filed Nov. 9, 2013, 298 pages.
[DKT 625] *Health Grades* vs. *MDX Medical, Inc.*, Health Grades, Inc.'s Motion for Leave to file Supplemental Exhibits in Support of Its Opposition [Doc. #201] to MDX's Second Motion Pursuant to Federal Rule of Civil Procedure 56 for Partial Summary Judgment of Non-Infringement [Doc. #195], filed Oct. 17, 2013, 86 pages.
[DKT 630] *Health Grades* vs. *MDX Medical, Inc.*, MDX Medical, Inc.'s Opposition to Health Grades' Motion for Leave to Amend Its Infringement Contentions, filed Oct. 18, 2013, 17 pages.
[DKT 631] *Health Grades* vs. *MDX Medical, Inc.*, Exhibit's B, E, F & I to Health Grades, Inc.'s Motion for Sanctions for MDx Medical, Inc.'s Failure to Comply with Court-Ordered Discovery [Filed Under Seal], filed Oct. 21, 2013, 38 pages.
[DKT 634] *Health Grades* vs. *MDX Medical, Inc.*, MDX Medical, Inc.'s Exhibit List for Hearing on Motion Pursuant to Federal Rule of Civil Procedure 56 for Partial Summary Judgment of Non-Infringement, filed Oct. 23, 2013, 4 pages.
[DKT 635] *Health Grades* vs. *MDX Medical, Inc.*, Health Grades, Inc.'s Exhibit List for Hearing on MDX Medical, Inc.'s Second Motion Pursuant to Federal rule of Civil Procedure 56 for Partial Summary Judgment of Non-Infringement [Doc. #195], filed Oct. 24, 2013, 5 pages.

(56) References Cited

OTHER PUBLICATIONS

[DKT 639] *Health Grades* vs. *MDX Medical, Inc.*, Redacted Version of Docket Nos. 626-2 and 626-2 [Redacted], filed Oct. 31, 2013, 63 pages.
[DKT 648] *Health Grades* vs. *MDX Medical, Inc.*, Redacted Version of Docket Nos. 632, 632-1, 632-5 and 632-6 [Redacted], filed Nov. 7, 2013, 72 pages.
U.S. Appl. No. 13/551,471, Petition Decision mailed Nov. 14, 2013, 3 pages.
U.S. Appl. No. 13/551,471, Notice of Allowance mailed Nov. 22, 2013, 16 pages.
U.S. Appl. No. 13/551,471, Notice of Allowance mailed Feb. 14, 2014, 2 pages.
[DKT 673] *Health Grades* vs. *MDX Medical, Inc.*, Health Grades, Inc.'s Unopposed Motion for Leave to Supplement its Brief in Support of its Motion for Partial Summary Judgment [Doc. #369], filed Dec. 9, 2013, 94 pages.
[DKT 674] *Health Grades* vs. *MDX Medical, Inc.*, MDX Medical, Inc.'s Notice Regarding its Second Motion Pursuant to Federal Rule of Civil Procedure 56 for Partial Summary Judgment of Non-Infringement (DKT. No. 195), filed Dec. 10, 2013, 11 pages.
[DKT 675] *Health Grades* vs. *MDX Medical, Inc.*, MDX Medical, Inc.'s Unopposed Motion for Leave to File a Response to Health Grades, Inc.'s Supplemental Brief in Support of its Motion for Partial Summary Judgment [Doc. #369], filed Dec. 10, 2013, 4 pages.
[DKT 685] *Health Grades* vs. *MDX Medical, Inc.*, MDX Medical, Inc.'s Motion In Limine to Preclude Health Grades, Inc. from Offering Certain Evidence or Testimony Regarding Validity, filed Dec. 17, 2013, 125 pages.
[DKT 696] *Health Grades* vs. *MDX Medical, Inc.*, Order Granting in Part and Denying in Part MDX's Motion for Partial Summary Judgment of Non-Infringement, filed Dec. 24, 2013, 32 pages.
[DKT 701] *Health Grades* vs. *MDX Medical, Inc.*, Health Grades, Inc.'s Brief Regarding the Reasonable Capability Test, filed Dec. 31, 2013, 6 pages.
[DKT 702] *Health Grades* vs. *MDX Medical, Inc.*, Health Grades, Inc.'s Brief Opposing MDX Medical, Inc.'s Request for Reconsideration of Claim Constructions in the Markman Order [Doc. #138], filed Dec. 31, 2013, 11 pages.
[DKT 705] *Health Grades* vs. *MDX Medical, Inc.*, MDX Medical, Inc.'s Brief Regarding Claim Construction for Claim 15 of the Asserted Patent, filed Dec. 31, 2013, 82 pages.
[DKT 706] *Health Grades* vs. *MDX Medical, Inc.*, MDX Medical, Inc.'s Brief Regarding Claim Construction for the Term "Verified" of the Asserted Patent, filed Dec. 31, 2013, 56 pages.
[DKT 725] *Health Grades* vs. *MDX Medical, Inc.*, Health Grades, Inc.'s Response in Opposition to MDX Medical, Inc.'s Motion In Limine to Preclude Health Grades, Inc. Offering Certain Evidence or Testimony Regarding Validity, filed Jan. 21, 2014, 83 pages.
[DKT 747] *Health Grades* vs. *MDX Medical, Inc.*, MDX Medical, Inc.'s Reply in Support of its Motion In Limine to Preclude Health Grades, Inc. from Offering Certain Evidence or Testimony Regarding Validity, filed Feb. 7, 2014, 19 pages.
[DKT 749] *Health Grades* vs. *MDX Medical, Inc., MDX Medical, Inc.'s* Supplemental to its Unopposed Motion for Leave to File a Response to Health Grades, Inc.'s Supplemental Brief in Support of its Motion for Partial Summary Judgment ]Doc. #369], field Feb. 11, 2014, 146 pages.
[DKT 752] *Health Grades* vs. *MDX Medical, Inc.*, Health Grades, Inc.'s Unopposed Motion for Leave to File a Reply to MDX Medical, Inc.'s Response to Health Grades, Inc.'s Proposed Supplemental Brief in Support of its Motion for Partial Summary Judgment [Doc. #3669], filed Feb. 12, 2014, 75 pages.
Corrected Petition for Inter Parties Review of U.S. Pat. No. 8,719,052 Pursuant to 35 U.S.C. Section 311-319, 37 C.F.R. Section 42, In The United States Patent and Trademark Office, dated Jul. 23, 2014 (63 pages).
Curriculum Vitae of Dr. Richard G. Cooper, no date available, 22 pages.
David A. Drucker, MD Report, dated Jun. 4, 2005, 4 pages.
Declaration for Richard G. Cooper, D.Sc., dated Jun. 30, 2014, 31 pages.
Declaration of Jeff LaPointe, dated Jun. 30, 2014, 20 pages.
Given, Ruth, "MD Rating Websites: Current State of the Space and Future Prospects," Nov. 5, 2008, 39 pages.
Physician Quality Comparison Report, report created Dec. 28, 2004, 24 pages.
Physician Quality Report, report created Sep. 15, 2004, 17 pages.
U.S. Appl. No. 60/771,757, filed Feb. 8, 2006, 20 pages.
Shelton, L. et al, "Recommendations for Improving the Quality of Physician Directory Information on the Internet," Aug. 2004, 30 pages.
Stone, E. et al, "Accessing Physician Information on the Internet," Filed Report on Jan. 2002, 43 pages.
U.S. Appl. No. 12/613,822, Non-Final Office Action mailed Feb. 4, 2015, 33 pages.
U.S. Appl. No. 12/830,255, Non-Final Office Action mailed Oct. 2, 2014, 21 pages.
Patent Owner's Preliminary Response, in the United States Patent and Trademark Office Before the Patent Trial and Appeal Board, *MDx Medical, Inc.* v. *Health Grades, Inc.*, Case IPR2014-01090, dated Oct. 16, 2014 (64 pages).
Fung, Constance H., et al. "Quality of Care: Patients' Preferences for Trechnical versus Interpersonal Quality When Selecting a Primary Care Physicaian," Health Research and Educational Trust, Aug. 2005, pp. 957-977.
*Health Grades* vs. *MDX Medical, Inc.*, MDX Medical, Inc.'s Unopposed Motion for Leave to Restrict Access to Documents—Document Nos. 754, 755 and 757, filed Mar. 3, 2014, 55 pages.
*Health Grades* vs. *MDX Medical, Inc.*, Exhibit A to MDX Medical, Inc.'s Unopposed Motion for Leave to Restrict Access to Document No. 770, filed Mar. 21, 2014, 10 pages.
*Health Grades* vs. *MDX Medical, Inc.*, Reporters Transcript Hearing, filed Apr. 4, 2014, 89 pages.
*Health Grades* vs. *MDX Medical, Inc.*, Order filed Apr. 30, 2014, 6 pages.
*Health Grades* vs. *MDX Medical, Inc.*, MDX Medical, Inc.'s Objections Pursuant to Fed. R. Civ. P. 72(a) to Magistrate Judge Boland's Order Dated Jan. 3, 2014 Imposing Discovery Sanctions and Order Dated Apr. 30, 2014 Denying Reconsideration filed Mar. 14, 2014, 16 pages.
*Health Grades* vs. *MDX Medical, Inc.*, Health Grade's Response to MDX's Fed. R. Civ. P. 72(A) Objections to Magistrate Judge Boland's Sanctions Order, filed Jun. 2, 2014, 28 pages.
*Health Grades* vs. *MDX Medical, Inc.*, MDX Medical, Inc.'s Reply Memorandum in Support of Its Objections Pursuant to Fed. R. Civ. P. 72(a) to Magistrate Judge Boland's Order Dated Jan. 3, 2014 Imposing Discovery Sanctions and Order Dated Apr. 30, 2014 Denying Reconsideration filed Jun. 19, 2014, 8 pages.
*Health Grades* vs. *MDX Medical, Inc.*, Order filed Jun. 26, 2014, 16 pages.
*Health Grades* vs. *MDX Medical, Inc.*, MDX Medical, Inc.'s Motion to Compel Document Discovery, Additional Depositions, and Queries on the Health Grades System; and Request for Expedited Treatment filed Jul. 25, 2014, 136 pages.
*Health Grades* vs. *MDX Medical, Inc.*, MDX Medical, Inc.'s Third Motion for Leave to Amend Invalidity Contentions filed Aug. 1, 2014, 278 pages.
*Health Grades* vs. *MDX Medical, Inc.*, Health Grades, Inc.'s Motion to Compel and for Additional Sanctions for MDX Medical, Inc.'s Failure to Comply with Court-Ordered Discovery filed Aug. 6, 2014, 18 pages.
*Health Grades* vs. *MDX Medical, Inc.*, Health Grades, Inc.'s Motion to Compel and for Additional Sanctions for MDX Medical, Inc.'s Failure to Comply with Court-Ordered Discovery—Exhibit D: Excerpt of Transcript from MDX 30(b)(6) Deposition on May 15, 2014, filed Aug. 6, 2014, 19 pages.
*Health Grades* vs. *MDX Medical, Inc.*, Plaintiff health Grades, Inc.'s Opposition to Defendant MDX Medical, Inc.'s Third Motion for Leave to Amend Invalidity Contentions, filed Aug. 13, 2014, 48 pages.
*Health Grades* vs. *MDX Medical, Inc.*, Plaintiff Health Grades, Inc.'s Opposition to Defendant MDX Medical, Inc.'s Motion to Compel

(56) References Cited

OTHER PUBLICATIONS

Document Discovery, Additional Depositions, and Queries on the Health Grades System, filed Aug. 13, 2014, 81 pages.
*Health Grades* vs. *MDX Medical, Inc.*, Exhibit 3—Plaintiff Health Grades, Inc.'s Opposition to Defendant MDx Medical, Inc.'s Motion to Compel Document Discovery, Additional Depositions, and Queries on the Health Grades System, filed Aug. 13, 2014, 6 pages.
*Health Grades* vs. *MDX Medical, Inc.*, MDX Medical, Inc.'s Unopposed Motion for Leave to Supplement Its Third Motion for Leave to Amend Invalidity Contentions filed Aug. 14, 2014, 6 pages.
*Health Grades* vs. *MDX Medical, Inc.*, Exhibits A-D: MDX Medical, Inc.'s Motion for Leave to Restrict Access to Documents—Document Nos. 818, 818-1, 818-4 and 818-6 filed Aug. 20, 2014, 70 pages.
*Health Grades* vs. *MDX Medical, Inc.*, MDX Medical, Inc.'s Motion in Limine to Preclude Health Grades, Inc. from Making Infringement Arguments Not in its Infringement Contentions, filed Aug. 21, 2014, 13 pages.
*Health Grades* vs. *MDX Medical, Inc.*, Exhibits in Support of 836 of MDX Medical, Inc.'s Motion in Limine to Preclude Health Grades, Inc. from Making Infringement Arguments not in its Infringement Contentions by Defendant MDX Medical, Inc., Counter Claimant MDX Medical, Inc. filed Aug. 21, 2014, 84 pages.
*Health Grades* vs. *MDX Medical, Inc.*, MDX Medical, Inc.'s Opposition to Health Grades, Inc.'s motion to Compel and for Additional Sanctions for MDX Medical, Inc.'s Alleged Failure to Comply with Court-Ordered Discovery filed Aug. 22, 2014, 29 pages.
*Health Grades* vs. *MDX Medical, Inc.*, Exhibits to Stimpson Affidavit filed Aug. 22, 2014, 64 pages.
*Health Grades* vs. *MDX Medical, Inc.*, Wheeler Trigg O'Donnell LLP and Terence M. Ridley's Response to Plaintiff's Motion for additional Sanctions filed Aug. 22, 2014, 4 pages.
*Health Grades* vs. *MDX Medical, Inc.*, MDX Medical, Inc.'s Motion for Leave to Restrict Access to Documents—Document Nos. 831 and 831-2 filed Aug. 27, 2014, 32 pages.
*Health Grades* vs. *MDX Medical, Inc.*, MDX Medical, Inc.'s Motion for Leave to Restrict Access to Documents—Document Nos. 839-2, 839-4, 839-5, 839-6, 839-7, 841-1, 841-7, 841-8, 843, 843-1, 843-2, 843-3, 843-4, 843-5 and 843-6 filed Sep. 5, 2014, 48 pages.
*Health Grades* vs. *MDX Medical, Inc.*, Order filed Sep. 8, 2014, 2 pages.
*Health Grades* vs. *MDX Medical, Inc.*, Hearing Transcript filed Sep. 10, 2014, 115 pages.
*Health Grades* vs. *MDX Medical, Inc.*, Health Grades, Inc.'s Response to "MDX Medical, Inc.'s Motion in Limine to Preclude Health Grades, Inc. from Making Infringement Arguments Not in Its Infringement Contentions", filed Sep. 15, 2014, 7 pages.
*Health Grades* vs. *MDX Medical, Inc.*, MDX Medical, Inc.'s Supplemental Opposition to Health Grades, Inc.'s Motion to Compel and for Additional Sanctions for MDX Medical, Inc.'s Alleged Failure to Comply with Court-Ordered Discovery filed Sep. 15, 2014, 55 pages.
*Health Grades* vs. *MDX Medical, Inc.*, MDX Medical, Inc.'s Objections to Magistrate Judge Boland's Order Denying the Motion to Amend Invalidity Contentions and the Motion to Compel a Search for NCQA Materials filed Sep. 22, 2014, 132 pages.
*Health Grades* vs. *MDX Medical, Inc.*, Health Grades, Inc.'s Supplemental Filing in Support of Its Motion to Compel and for Additional Sanctions for MDX Medical, Inc.'s Failure to Comply with Court-Ordered Discovery filed Sep. 9, 2014, 11 pages.
*Health Grades* vs. *MDX Medical, Inc.*, MDX Medical, Inc.'s Motion for Leave to Restrict Access to Documents—Document Nos. 868, 868-1, 870, 870-1, 871, 871-1, 871-2, 871-7 and 871-8 filed Sep. 29, 2014, 118 pages.
*Health Grades* vs. *MDX Medical, Inc.*, MDX Medical, Inc.'s Reply Memorandum in Support of Its Motion in Limine to Preclude Health Grades, Inc. from Making Infringement Arguments Not in Its Infringement Contentions filed Oct. 2, 2014, 21 pages.
*Health Grades* vs. *MDX Medical, Inc.*, Reporters Transcript Motions Hearing filed Oct. 14, 2014, 116 pages.
*Health Grades* vs. *MDX Medical, Inc.*, MDX Medical, Inc.'s Submission of Accused Configurations filed Oct. 14, 2014, 15 pages.
*Health Grades* vs. *MDX Medical, Inc.*, Plaintiff Health Grades' Opposition and Response to MDX Medical, Inc.'s Objections to Magistrate Judge Boland's Order Denying the Motion to Amend Invalidity Contentions and the Motion to Compel a Search for NCQA Material filed Oct. 14, 2014, 20 pages.
*Health Grades* vs. *MDX Medical, Inc.*, Plaintiff Health Grades, Inc.'s Submission re Configurations of Infringement filed Oct. 14, 2014, 93 pages.
*Health Grades* vs. *MDX Medical, Inc.*, Plaintiff Health Grades, Inc.'s Submission re Configurations of Infringement filed Oct. 14, 2014, 84 pages.
*Health Grades* vs. *MDX Medical, Inc.*, Health Grades, Inc.'s Motion to Amend Its Infringement Contentions to Incorporate Dr. Greenspun's Third Supplemental Expert Report filed Oct. 14, 2014, 119 pages.
*Health Grades* vs. *MDX Medical, Inc.*, Health Grades, Inc.'s Motion to Compel filed Oct. 14, 2014, 92 pages.
*Health Grades* vs. *MDX Medical, Inc.*, Order filed Oct. 23, 2014, 22 pages.
*Health Grades* vs. *MDX Medical, Inc.*, MDX Medical, Inc.'s Motion for Leave to Restrict Access to Documents—Document Nos. 908-4, 908-5, 908-8 and 909-3 filed Oct. 28, 2014, 15 pages.
*Health Grades* vs. *MDX Medical, Inc.*, MDX Medical, Inc.'s Reply Memorandum in Support of Its Objections to Magistrate Judge Boland's Order Denying the Motion to Amend Invalidity Contentions and the Motion to Compel a Search for Ncqa Materials filed Oct. 31, 2014, 94 pages.
*Health Grades* vs. *MDX Medical, Inc.*, Order filed Nov. 3, 2014, 4 pages.
*Health Grades* vs. *MDX Medical, Inc.*, Order on Indirect Infringement filed Nov. 4, 2014, 14 pages.
*Health Grades* vs. *MDX Medical, Inc.*, MDX Medical, Inc.'s Motion from Leave to Supplement Its Objections to Magistrate Judge Boland's Order Denying the Motion to Amend invalidity Contentions and the Motion to Compel a Search for NCQA Materials, filed Nov. 7, 2014, 14 pages.
*Health Grades* vs. *MDX Medical, Inc.*, MDX Medical, Inc.'s, Health Grades, Inc.'s Electronic Filing of Its Nov. 6, 2014 Hearing Exhibits, filed Nov. 10, 2014, 381 pages.
U.S. Appl. No. 12/830,255, Amendment and Response filed Apr. 2, 2015, 16 pages.
U.S. Appl. No. 12/830,255, Final Office Action mailed Apr. 22, 2015, 18 pages.

* cited by examiner

CONNECTING PATIENTS WITH EMERGENCY/URGENT HEALTH CARE

CROSS-REFERENCE TO RELATED APPLICATION

This application is a continuation-in-part of, and claims priority to, U.S. patent application Ser. No. 12/613,822, filed on Nov. 6, 2009, by Inventor John M. Neal, and entitled, "PATIENT DIRECT CONNECT." The entirety of the aforementioned application is incorporated herein by reference.

COPYRIGHT NOTICE AND PERMISSION

A portion of the disclosure of this patent document may contain material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice shall apply to this document: Copyright.COPYRGT. 2010, Health Grades, Inc.

BACKGROUND

A large percentage of medical conditions require urgent or emergency care. While patients in need of urgent or emergency care may need immediate assistance, it is important to still allow such patients to make informed decisions in selecting their medical care provider, e.g., hospital, emergency room, urgent care facility, physician, etc. Yet, a great deal of information to enable such decision-making is not available, or at least not readily available, to potential patients. While increasing numbers of patients are also opting for convenient care facilities or clinics for treatment of medical conditions requiring non-emergency or non-urgent care, information to enable potential patients to make informed decisions in selecting a particular convenient care facility has also been limited or, at least, not readily available. Such problems are exacerbated in that potential patients often select such facilities, whether emergency/urgent or convenient care, in rushed situations and/or while en route to a facility of a particular type, e.g., emergency room.

Although specific problems have been addressed in this Background, this disclosure is not intended in any way to be limited to solving those specific problems.

SUMMARY

Embodiments generally relate to providing potential patients, or any type of user, the content and tools to enable them to make informed decisions regarding their selections of emergency, urgent, and/or convenient care facilities. Potential patients are able to access information and data regarding emergency, urgent, and convenient care over a computer network. In embodiments, such information is provided in response to searches conducted by potential patients for facilities satisfying specific criteria. In other embodiments, such information is provided in response to a search for a particular facility. Such information and data includes, for example, current wait times at particular facilities, physical distance to such facilities from a specific location, specialties and quality/award ratings of such facilities, physicians and/or other treating personnel at such facilities, etc. Further, where the search results include multiple facilities, comparisons of such information and data between facilities can also be provided according to embodiments. For example, the search results may be displayed to a user in order of the shortest wait time to the longest wait time. In another embodiment, the search results may be displayed in order of the closest geographic location to the user's current location to the furthest geographic location from the user. In an embodiment, a user's location is automatically provided in the search by using navigation satellite technology, such as the Global Positioning System (GPS). In yet another embodiment, search results may be displayed in such order as to highlight, or otherwise give preferential treatment to, certain facilities which are affiliated with the company providing the search capabilities and results. For example, such service for obtaining such information may be obtained at the Web site(s) provided by Health Grades, Inc. Such Web site(s) include, for example, www.healthgrades.com.

In additional embodiments, after selecting a particular facility, a potential patient sends an electronic notification to the facility informing the facility of the user's desired imminent arrival. The notification includes, in embodiments, a description of the patient's condition and identifying information. Such information allows the user to perform a "pre-check-in" process and save time when the user actually arrives at the facility. The notification also allows the facility to determine whether or not it has the resources to accept the patient. In processing the notification, the facility may determine, in embodiments, that it cannot provide service to the potential patient in a timely manner and may send the user a denial of service response to the notification. In other embodiments, the facility determines that it has the resources to accept the potential patient and sends a confirmation to the patient. Such confirmation comprises directions, in embodiments. In embodiments, such confirmation also comprises instructions for the potential patient, such as to keep an injured limb elevated, for example. In other embodiments, the confirmation also requests further information of the potential patient. Such further information enables the facility to perform a triage, or quasi-triage, to determine the priority of treatment for patients based on the degree of severity of the patients' respective medical conditions. By enabling such upfront contact between potential patients and care facilities, time is saved and the efficiency of the care giving process is optimized.

In other embodiments, after selecting a particular care facility, the patient directly contacts the facility by using a contact mechanism provided by the search service, such as a unique phone number, electronic mail (email) address, and/or Short Message Service (SMS) address. Such phone number or email address is created such as to allow the tracking of patients who choose to contact the facility directly after obtaining search results. In still other embodiments, a user may use the service to obtain contact information for consulting a nurse or other medical practitioner for answering questions about, or otherwise discussing, the potential patient's medical condition.

This Summary is provided to introduce a selection of concepts in a simplified form that is further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

Embodiments of the present disclosure may be more readily described by reference to the accompanying drawings in which like numerals refer to like items.

DETAILED DESCRIPTION

Figure 1:
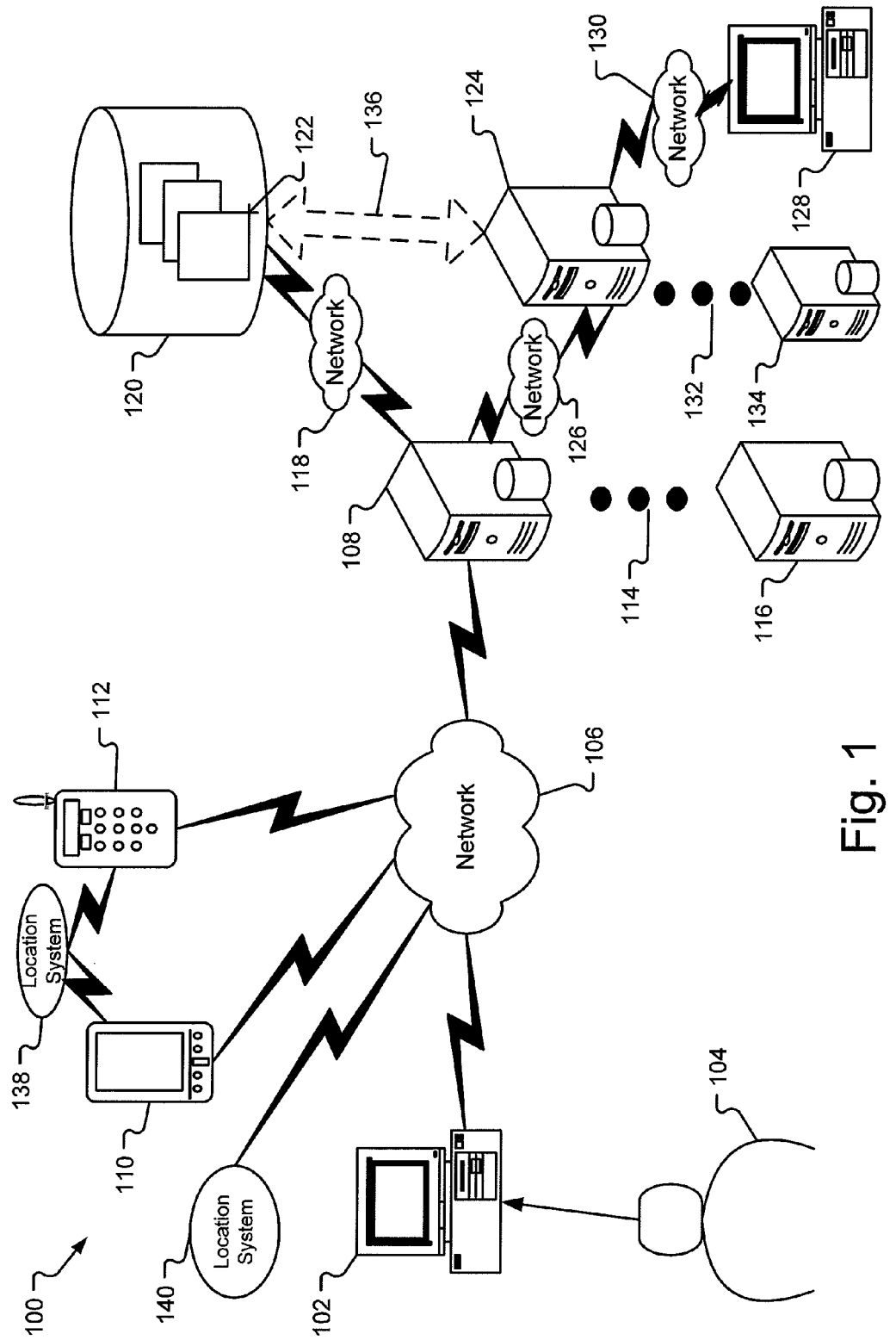
FIG. 1 illustrates an example logical representation of an environment or system for providing potential patients with content and tools to make informed decisions regarding emergency care, urgent care, convenient care, and/or physician care in accordance with embodiments disclosed herein.

This disclosure will now more fully describe example embodiments with reference to the accompanying drawings, in which specific embodiments are shown. Other aspects may, however, be embodied in many different forms, and the inclusion of specific embodiments in this disclosure should not be construed as limiting such aspects to the embodiments set forth herein. Rather, the embodiments depicted in the drawings are included to provide a disclosure that is thorough and complete and which fully conveys the intended scope to those skilled in the art. Dashed lines may be used to show optional components or operations.

Embodiments generally relate to connecting potential patients with emergency care, urgent care, and/or convenient care facilities. A company provides on-line healthcare facility search services to potential patients and/or users to connect potential patients with the emergency, urgent, and/or convenient care facility which best meets their needs or desires for medical treatment. According to embodiments, the company providing the search services manages a Web site(s) with one or more Web pages for accessing, transmitting, and receiving information regarding healthcare facilities, including emergency, urgent, and/or convenient care facilities, for example, to enable users and/or potential patients to make informed decisions regarding their healthcare treatment facility needs. "Users" and "potential patients" are used interchangeably herein. For example, while potential patients may access the company Web site to obtain information regarding medical treatment facilities, a "user" may access the company Web site to assist a potential patient who may or may not be able to use the Web site himself/herself, such as, for example, a child or incapacitated person. In further embodiments, the Web site may be mobile-enabled such that it acts as a nexus for all Internet and mobile consumers. In such embodiments, the Web site is capable of receiving requests from both mobile users (e.g., users accessing the Web site via a mobile phone, smartphone, PDA, etc.) and requests from standard Internet users (e.g., users accessing the Web site via a computer connected to the Internet. Furthermore, the Web site may be capable of returning responses in multiple different formats depending on the device making the additional request (e.g., a response formatted for a mobile device or a response formatted for a browser on a computer).

In embodiments herein, "emergency" care may refer to treatment received at an "emergency room." An emergency room ("ER"), which is also known as an emergency department ("ED"), is a dedicated department in a hospital or freestanding healthcare facility that provides specialized 24/7 treatment of medical emergencies. Medical emergencies require immediate treatment and include diseases and conditions that threaten life, limb or vision, such as, for example, chest pain, cardiopulmonary arrest, trauma, stroke, eye injuries, etc. An "urgent care" facility or center, also known as an immediate care center, is a healthcare facility providing convenient treatment of minor to moderate diseases and conditions that need prompt medical care, but do not require a visit to the emergency room. Urgent care centers provide treatment for such conditions as, for example, minor to moderate lacerations, simple bone fractures, muscle strains, sprains and contusions, cysts or boils, minor dehydration, strep throat, ear infections, flu/influenza, etc. On the other hand, a "convenient care" facility or clinic, also known as a retail health clinic, is a healthcare facility providing convenient, routine healthcare and treatment of minor diseases and conditions. Retail health clinics generally provide treatment to patients two years of age and older for such conditions as, for example, upper respiratory infection, uncomplicated flu/influenza, minor rashes and skin conditions, pink eye, pregnancy testing, muscle strains, sprains and contusions, etc. Convenient care facilities also provide, for example, routine immunizations, such as flu-shots, hepatitis vaccines, MMR (Measles, Mumps, and Rubella) vaccines, school and sports physicals, preventative health screenings, such as cholesterol, hypertension, and diabetes tests, etc. While specific conditions and descriptions have been described with respect to each type of facility, e.g., emergency, convenient care, and urgent care, these conditions and descriptions may apply to one or more facilities described above and overlapping of descriptions and medical conditions treated by the facilities may exist. The names and descriptions provided above are offered as non-limiting examples.

According to embodiments, while the company providing on-line healthcare facility search services provides information and data to allow potential patients and/or users to make informed decisions regarding their healthcare facility needs, the on-line service also provides a phone number(s), email address, and/or IM (Instant Messaging) address, for example, for potential patients and/or users to contact a medical practitioner to obtain answers to any questions they may have regarding their particular medical condition. Answers to such questions may enable a potential patient to determine whether to seek treatment at an emergency room versus an urgent care facility versus a convenient care facility, for example. An example of such a medical practitioner contact is the "Consult-a-Nurse" service. However, any type or name of such medical practitioner contact service may be used in accordance with embodiments disclosed herein. Users and/or potential patients may consult such a medical practitioner by phone or other contact means at any time during the search/notification process using phone numbers or other contact means displayed by Web pages of the Web site managed by the company providing on-line healthcare facility search services.

In embodiments, users are able to enter search criteria for finding emergency, urgent, and/or convenient care facilities by shortest wait times, closest physical proximity, highest quality ratings, etc. In determining proximity information, users may either provide their current location or use data provided by a navigation satellite system to indicate the exact geographic coordinates of the user's location. In other embodiments, affiliated users of a company providing the search services for emergency, urgent, and/or convenient care may log-in or otherwise indicate their member status and obtain quicker access to entering search criteria by having their personal information automatically populated in search forms, for example. Upon processing the search criteria, search results are provided to the potential users and/or patients. In receiving search results, users and/or potential patients can make informed decisions regarding their choice of healthcare facility for emergency, urgent, and/or convenient care, for example.

In embodiments, a user and/or potential patient may send an electronic notification of his/her arrival at a particular emergency, urgent, and/or convenient care facility. In other embodiments, the potential patient and/or user contacts a desired facility directly using a phone number, email address, and/or SMS address, for example, received from a Web page displaying search results for the particular healthcare facilities matching the search criteria. The particular phone number, email address, and/or SMS address provided allows the facility and/or company providing on-line healthcare facility search services to track the user's and/or potential patient's use of the company Web site and/or search results for finding the facility.

In embodiments where a user and/or potential patient sends an electronic notification of expected arrival, such notification includes an expected arrival time, according to embodiments. The notification also includes an indication of the potential patient's particular medical condition requiring care, in accordance with embodiments disclosed herein. Upon receiving the electronic notification, the care facility determines whether it can accept the potential patient. Factors influencing the facility's decision include availability of physicians, availability of treatment rooms and/or equipment, etc. The care facility then transmits its reply, e.g., confirmation or denial of the patient's request, to a server(s) used by the company. The company then forwards the reply to the potential patient and/or user. In sending a confirmation, the facility may also request additional information to allow it to triage the patient before his/her arrival. The patient and/or user may therefore reply to such request for additional information and send such information through the server(s) used by the company to the hospital to begin the triage process. Such ability to begin triaging a patient while he/she is en route to the facility results in increased efficiency and response times, as well as overall improved medical care.

In embodiments, the confirmation may include additional information related to the facility. For example, the confirmation may include directions to facility. The confirmation and/or additional information may be sent to the phone number, email address, and/or SMS address used to make the initial request. In embodiments, the user making the request may provide a different phone number, email address, and SMS address, and/or any other means of contact that the confirmation and/or additional information should be returned to. In further embodiments, the user may provided multiple phone numbers, email addresses, SMS addresses, etc., in which case the confirmation information and/or additional information may be sent to the multiple contract numbers and/or addresses provided. For example, a patient checking into the hospital may also provide an email address, phone number, etc. of a family member and specify that confirmation information and or additional information (e.g., driving directions to the facility, facility contact information, etc) may be sent to the multiple contact numbers and/or addresses provided. In such embodiments, the company then provides this additional information to the patient's family member.

An example logical environment or system 100 for providing on-line search services for connecting potential patients with emergency, urgent, and/or convenient care facilities is shown in FIG. 1, in accordance with embodiments disclosed herein. User and/or potential patient 104 uses client computer 102 to access a company server 108 across network 106 to search for emergency, urgent care, and/or convenient care facilities. In another embodiment, user and/or potential patient 104 accesses a company server 108 over network 106 from a mobile phone 112. In yet another embodiment, user and/or potential patient 104 accesses a company server 108 over network 106 from mobile device 110, such as a personal digital assistant ("PDA") 110. While FIG. 1 depicts servers 108, 114, 116, 124, 132, and 134, any number of servers may be used as shown by ellipses 114 and 132, in accordance with embodiments disclosed herein. In embodiments, servers described herein are owned, leased, managed, part of cloud computing services, hardware, software, and/or a combination of hardware and software operable to execute the functions described herein.

According to embodiments, upon receiving a search request across network 106, company server 108 processes such search request by accessing information and data stored in database 120, for example. Such data and information is accessed over network 118 in embodiments. For example, database 120 stores membership information profiles 122, facility ratings 122, facility reports 122, etc. In processing a search request, company server 108 accesses a facility server 124 over network 126, in accordance with embodiments. Facility server 124 provides, for example, current wait times at the particular facility, requests for further patient information, confirmations or denials of patient notification requests, etc. In further embodiments, the Facility server 124 provides additional information related to the facility, such as, but not limited to, services offered by the facility, awards earned, professional and staffing information, related news articles, certifications, or any other type of Facility related information that may be of interest to the user/patient. In accessing and relaying such information, facility server 124 communicates with client computer 128 over network 130 in embodiments. For example, a facility employee enters or updates current wait times at client computer 128 using an input device. In an embodiment, this information or data is transmitted to server 124 for processing, further storing, and relaying to company server 108. In another embodiment, server 124 may directly populate forms and/or other information 122 stored in database 120 through communications 136 between server 124, 132, and 134, for example, and database(s) 120. While embodiments provide for a single facility server 124, other embodiments provide for multiple facility servers as shown by ellipses 132 and facility server 134. These facility servers may be associated with the same facility, such as "State Hospital" or may be associated with a plurality of different facilities, such as a facility server associated with "State Hospital" and another facility server associated with "University Hospital," in accordance with embodiments. Any number and type of servers may be used without departing from the spirit and scope of the present disclosure. Further, while the servers 108, 114, 116, 124, 132, and 134 in FIG. 1 depict attached databases, other embodiments provide for each server having access to a detached database or to multiple and separate detached databases.

Embodiments also provide for the use of a location system, as depicted in FIG. 1, for determining a user's and/or potential patient's current location, such as for determining proximity of facilities to the potential patient, etc. For example, navigation satellite systems, such as the Global Positioning System ("GPS") 138 provide a user or potential patient's 104 current geographic or physical location information, such as in the form of real-time latitude/longitude geographic coordinates, to mobile device 110 and/or mobile phone 112, according to embodiments. Devices 110 and 112 then transmit the received real-time coordinates over network 106 to server 108, for example. In an embodiment, server 108 then compares the received coordinates with stored address information, such as in a database(s), to determine the correlating address for the received coordinates. In another embodiment, an intermediary server or other server receives the coordinates and correlates them with an address. Where multiple addresses correlate with the received coordinates, the multiple addresses are transmitted over network 106 to devices 110 and/or 112. In embodiments, the user and/or potential patient may then determine the correct address from a list of addresses matching the coordinates. In another embodiment, a receiver receives location information data or coordinates from location system 140 and communicates these coordinates to client computer 102 to determine location information of client computer 102 using a location application. In other embodiments, the user's and/or potential patient's current location information is determined through triangulation from a cellular network.

In embodiments, such information or data regarding the user's or potential patient's 104 current location information is used to automatically populate a form for sending a search request to company server 108, for example, for facility information matching specific search criteria. In yet other embodiments, such information and/or data is sent directly to company server 108 for processing to determine the facilities within the closest proximity of the potential patient or user 104. Such proximity results may be displayed to a user and/or potential patient 104 before the user and/or potential patient 104 enters specific search criteria in embodiments. Instead, in such embodiments, such proximity results may be provided as soon as the user and/or potential patient 104 indicates that he/she would like information regarding emergency, urgent care, and/or convenient care facilities.

Logical environment 100 is not limited to any particular implementation and instead embodies any computing environment upon which the functionality of the environment described herein may be practiced. For example, any type of client computer 102 understood by those of ordinary skill in the art may be used in accordance with embodiments. Further, networks 106, 118, 126 and 130, although shown as individual single networks may be any types of networks conventionally understood by those of ordinary skill in the art. In accordance with an embodiment, the network may be the global network (e.g., the Internet or World Wide Web, i.e., "Web" for short). It may also be a local area network, e.g., intranet, or a wide area network. In accordance with embodiments, communications over networks 106, 126 and 130 occur according to one or more standard packet-based formats, e.g., H.323, IP, Ethernet, and/or ATM.

Further, any conceivable environment or system as understood by those of ordinary skill in the art may be used in accordance with embodiments of the present disclosure. FIG. 1 is offered as an example only for purposes of understanding the teachings of the embodiments disclosed herein. For example, FIG. 1 shows company server 108, 114 and 116 and facility server 124, 132 and 134. However, embodiments also cover any type of server, separate servers, server farm, or other message server. Further yet, FIG. 1 shows client computer 102. However, any type of small computer device may be used as is understood by those of ordinary skill in the art without departing from the spirit and scope of the embodiments disclosed herein. Although only one client computer 102 is shown, for example, another embodiment provides for multiple small computer devices to communicate with company server 108. In an embodiment, each small computer device communicates with the network 106, or, in other embodiments, multiple and separate networks communicate with the small computer devices. In yet another embodiment, each small computer device communicates with a separate network. In another embodiment, an application programming interface ("API") is used to facilitate connections between clients, such as client computer 102, mobile phone 110, mobile device 112, etc. and the company server 108. The API may be use to facilitate communication between the client devices and the company and/or facility servers by providing the mobile devices access to data and/or functional aspects of the company server 108. In further embodiments, the API may provide the company server additional access to information on the client devices, such as but not limited to, the location of the client device. Indeed, environment or system 100 represents a valid way of practicing embodiments disclosed herein but is in no way intended to limit the scope of the present disclosure. Further, the example network environment 100 may be considered in terms of the specific components described, e.g., company server, client computer, etc., or, alternatively, may be considered in terms of the analogous modules corresponding to such units.

Figure 2:
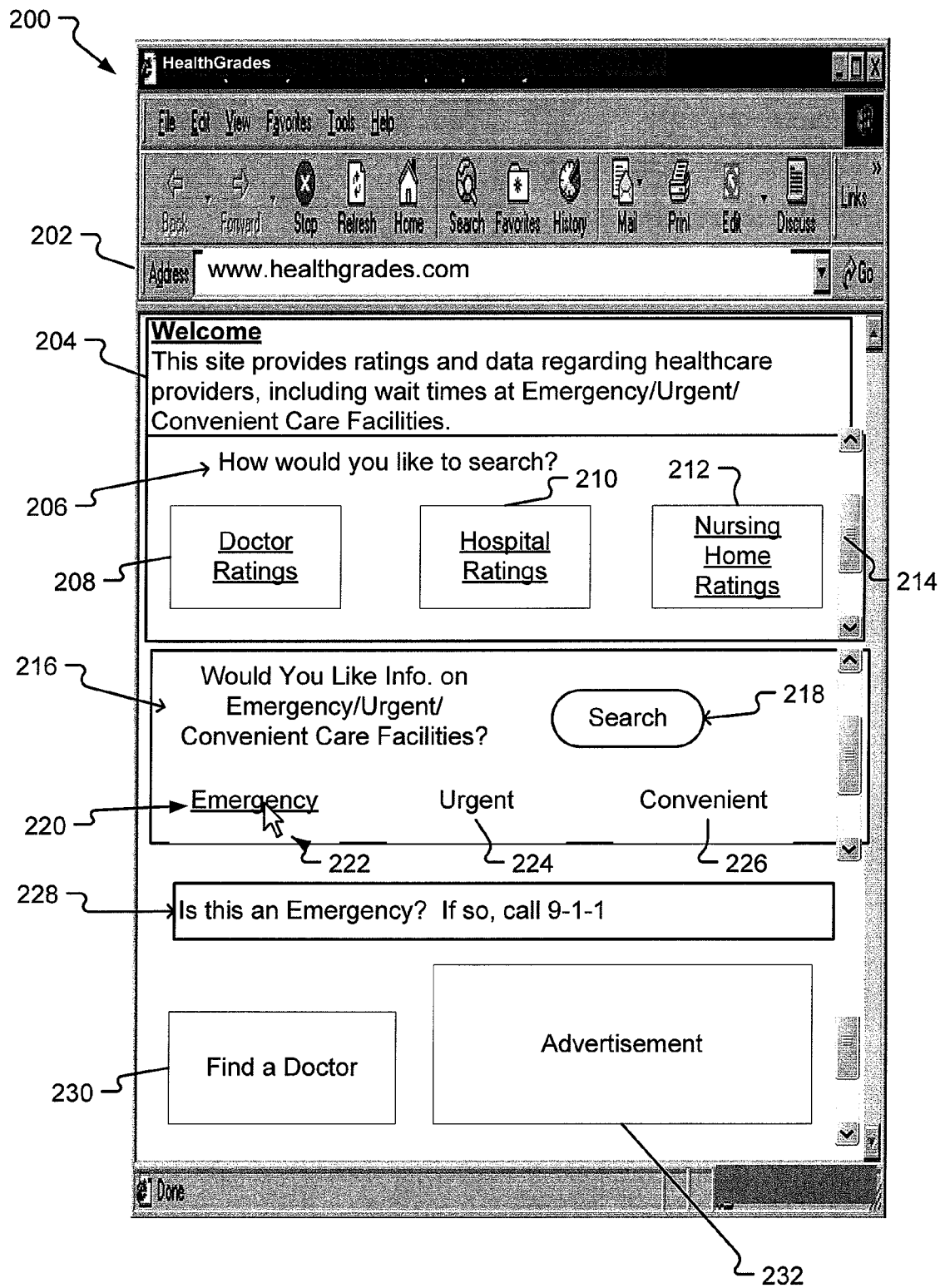
FIG. 2 depicts an example user interface (UI) of a Web page, as retrieved in the logical representation of the environment or system of FIG. 1, for example, with options for selecting to search for hospitals, physicians, nursing homes, and emergency/urgent/convenient care facilities in accordance with embodiments disclosed herein.

While FIG. 1 depicts an example logical environment or system 100 for providing on-line search services for connecting potential patients with emergency, urgent, and/or convenient care facilities, FIG. 2 illustrates an example user interface (UI) 200 of a Web page, as retrieved in the logical representation of the environment or system 100 of FIG. 1, for example, with options for selecting to search for hospitals, physicians, nursing homes, and emergency/urgent/convenient care facilities in accordance with embodiments disclosed herein. User interface 200 is accessed, in embodiments, by providing the Uniform Resource Locator ("URL") 202, or address of the Web page, of the company providing the healthcare facility search services. For example, UI 200 shows the Web address "www.healthgrades.com" for the HealthGrades® Web site. Upon entering the home page of the company Web site, UI 200 depicts an introductory or welcome display 204 indicating the services offered by the Web site, according to embodiments. A user and/or potential patient determines how he/she would like to search regarding their healthcare needs 206, such as by doctor ratings 208, hospital ratings 210, and/or nursing home ratings 212. Such search capabilities are described in U.S. Pat. No. 7,752,060, entitled, "Internet System for Connecting Healthcare Providers and Patients," issued on Jul. 6, 2010, which is incorporated herein by reference in its entirety for all that it teaches.

User interface 200 also offers the user and/or potential patient the option to access information regarding emergency, urgent, and/or convenient care facilities 216, in accordance with embodiments. The user and/or potential patient clicks on a "Search" button 218 to access such information in embodiments. In alternative embodiments, the user and/or potential patient accesses such information by selecting "Emergency" 222, "Urgent" 224, or "Convenient" 226. For example, FIG. 2 depicts the user and/or potential patient having moved the mouse pointer 222 over "Emergency" to select information on emergency care facilities.

Embodiments also provide for UT 200 to provide a reminder to phone "9-1-1" in case of an emergency 228 requiring immediate assistance. Further, UI 200 allows a user and/or potential patient to search for information on a particular physician, such as through clicking on the "Find a Doctor" selector 230. User interface 200 also includes an advertisement 232 or multiple advertisements on the Web page 200.

User interface 200 is offered for purposes of illustration only. Any type of user interface can be used in accordance with embodiments disclosed herein. Further, the specific buttons, selectors, text, headings, etc., are offered by way of example only for purposes of illustration. Any type and arrangement of text, buttons, selectors, and/or other features and functions may be used in accordance with embodiments disclosed herein. Further, while user interface 200 shows an indicator of "Microsoft Internet Explorer" and "WWW" in the example depicted, these are offered for purposes of illustration only. For example, an intranet and/or other type of network may be used in accordance with other embodiments.

Figure 3A:
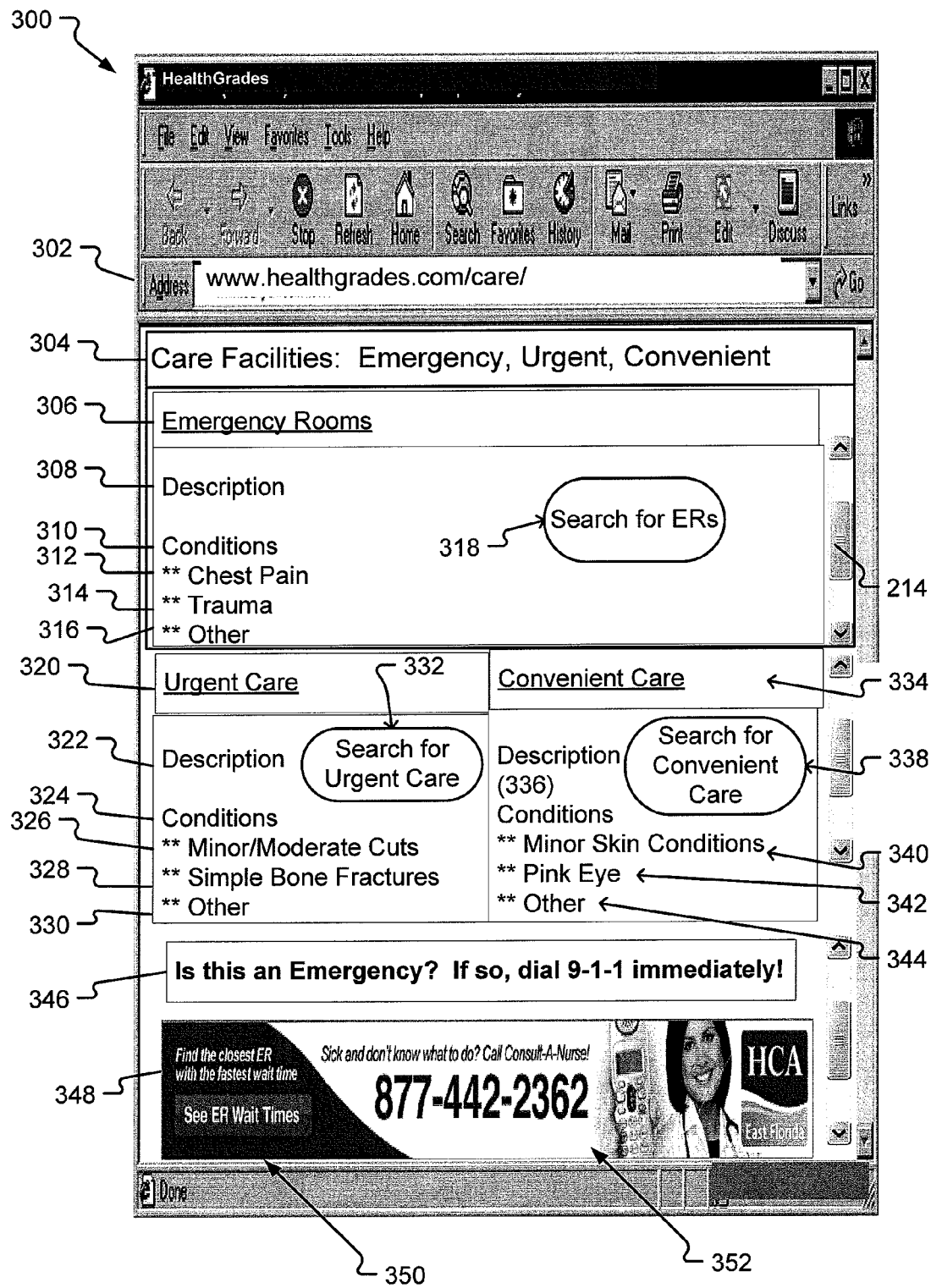
FIG. 3A illustrates an example user interface (UI) of a Web page, as retrieved in response to selecting to search for emergency/urgent/convenient care facilities in the user interface of FIG. 2, for example, with options for searching for emergency/urgent/convenient care facilities, consulting a nurse or other practitioner, and viewing wait times for emergency facilities in accordance with embodiments disclosed herein.

Turning to FIG. 3A, user interface 300 illustrates an example user interface (UI) 300 of a Web page, as retrieved in response to selecting the "Search" button 218 of FIG. 2 for accessing information on emergency, urgent care, and/or convenient care facilities in accordance with embodiments disclosed herein. For example, URL 302 indicates the selection of a search for a healthcare facility, as depicted by "www.healthgrades.com/care/." Web page 300 shows that information and/or searches may be obtained for emergency, urgent, and/or convenient care facilities 304. An emergency room section 306 provides a description 308 of emergency room services and types of conditions 310 applicable to emergency room treatment, such as, for example, chest pain 312, trauma 314, and/or other conditions 316. A user and/or potential patient may search for particular emergency room facilities matching specified search criteria by clicking on the "Search for ERs" button 318 to begin a search, according to embodiments.

In embodiments, Web page 300 also depicts a section on "Urgent Care" 320, including a description 322 of such facility. In further embodiments, Web page 300 also lists medical conditions 324 commonly treated at such facility, such as, for example, minor/moderate cuts 326, simple bone fractures 328, and/or other conditions 330. A user and/or potential patient may also search for an urgent care facility by clicking on the "Search for Urgent Care" button 332 and then entering search criteria when prompted to do so.

Additionally, Web page 300 provides a section on "Convenient Care" 334. This section includes a description 336 of such type of care according to embodiments. In further embodiments, Web page 300 also lists commonly treated medical conditions at convenient care facilities, including, for example, minor skin conditions 340, pink eye 342, and/or other conditions 344. A user and/or potential patient may also search for a convenient care facility by clicking on the "Search for Convenient Care" button 338.

In embodiments, Web page 300 provides a reminder 346 to phone "9-1-1" if the potential patient's condition requires immediate treatment/care. In other embodiments, Web page 300 also provides alternative ways to connect potential patients with a healthcare facility, such as through display 348. Display 348 provides the ability to find out the "closest ER with the fastest wait time" by clicking on a "See ER Wait Times" button 350, as disclosed in embodiments herein. In additional embodiments, a phone number 352 or other contact means to consult a medical practitioner, such as through the "Consult-A-Nurse" service, for example, is provided on Web page 300 to assist users and/or potential patients in directly contacting a medical practitioner for questions regarding healthcare facility information and treatment options.

Figure 3B:
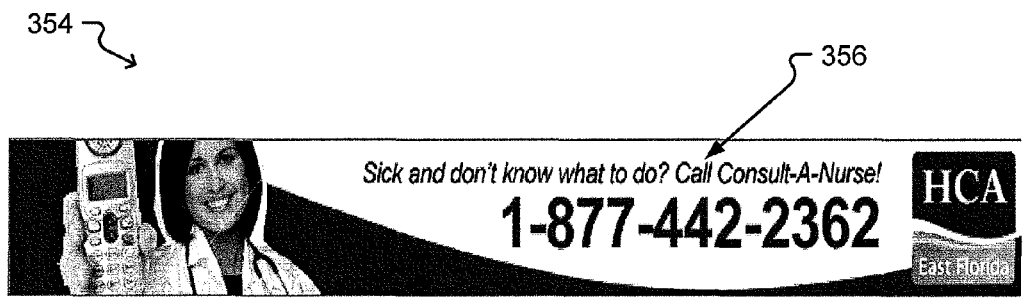
FIG. 3B illustrates an example display for contacting a nurse or other practitioner for consultation regarding a medical condition in accordance with embodiments disclosed herein.
Figure 3C:
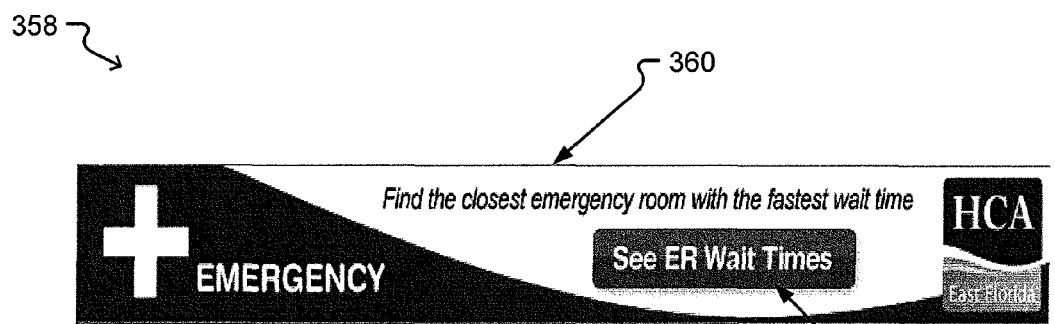
FIG. 3C depicts an example display for viewing emergency room wait times in accordance with embodiments disclosed herein.

While Web page 300 depicts display 348 for finding out the "closest ER with the fastest wait time" and/or directly contacting a medical practitioner, FIGS. 3B and 3C illustrate example displays 354 and 358 which may be used instead of display 348, in addition thereto, or in any combination thereof. For example, display 354 illustrates means to contact a medical practitioner through a provided phone number 356. As an example, display 354 displays the phone number for contacting the "Consult-A-Nurse" service. In other embodiments (not shown), contact means other than a phone number may be provided for contacting a medical practitioner, such as an email address, SMS address, etc. While FIG. 3B depicts the contact information for a medical practitioner, FIG. 3C shows display 358 for finding the closest emergency room with the fastest wait time 360. A user may click on the "See ER Wait Times" button 362 to search for ER wait times, in accordance with embodiments.

User interface 300, including displays 348, 354 and 358, for example, are offered for purposes of illustration only. Any type of user interface can be used in accordance with embodiments disclosed herein. Further, the specific buttons, selectors, text, headings, etc., are offered by way of example only for purposes of illustration. Any type and arrangement of text, buttons, selectors, and/or other features and functions may be used in accordance with embodiments disclosed herein. Further, any number of sections may be used, in which greater than or fewer than the number of sections depicted may be used in embodiments. For example, the emergency room 306, urgent care 320, and convenient care 334 facility sections may each be provided on separate Web pages and accessed by separate URLs specific to each type of facility, in accordance with embodiments. In other embodiments, any combination or sub-combination of the sections shown in FIG. 3 may be used. As an example, Web page 300 may depict "Emergency Room" section 306 and "Urgent Care" section 320, but not include the "Convenient Care" section 334. Further yet, while user interface 300 shows an indicator of "Microsoft Internet Explorer" and "WWW" in the example depicted, these are offered for purposes of illustration only. For example, an intranet and/or other type of network may be used in accordance with other embodiments.

Figure 4A:
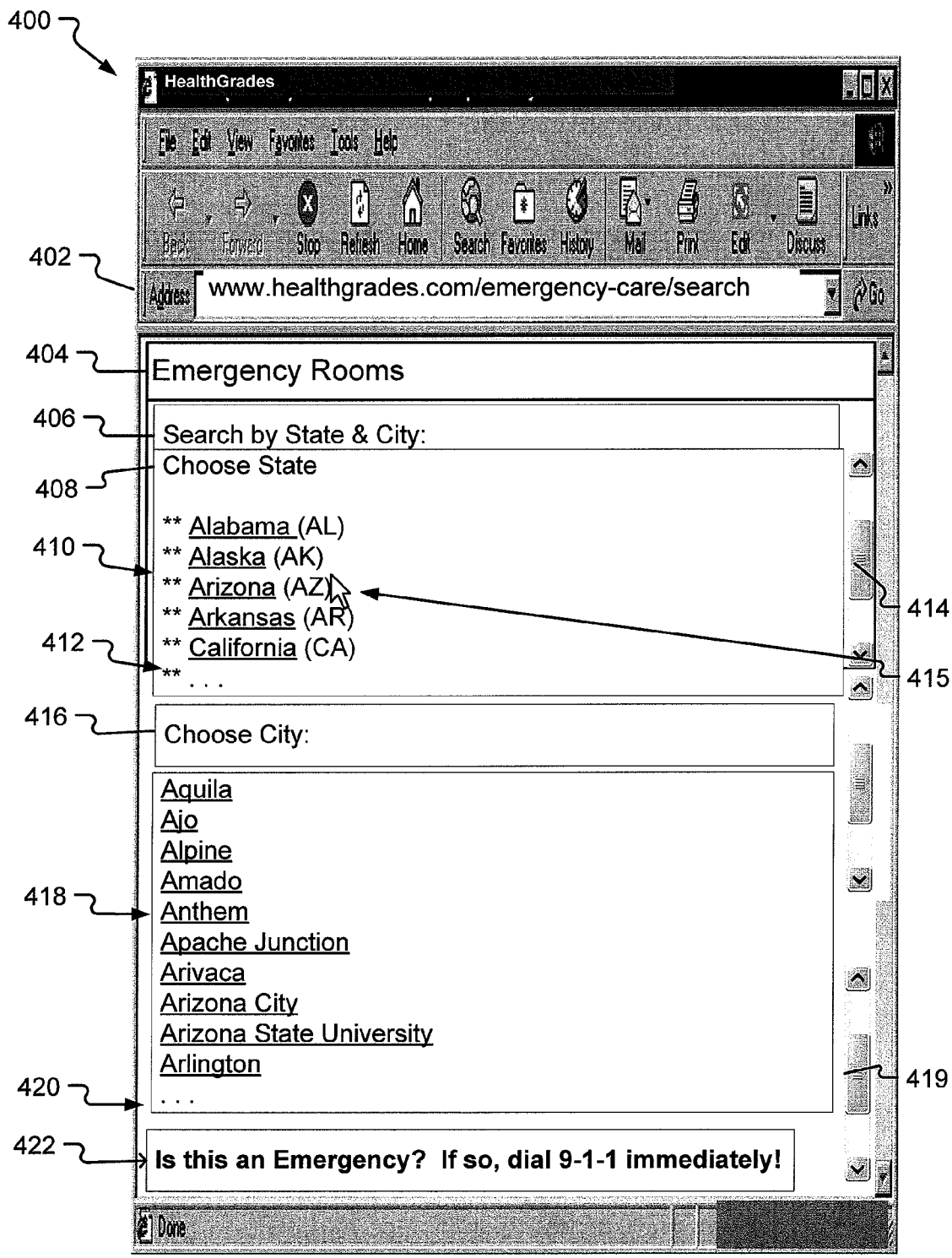
FIG. 4A illustrates an example user interface (UI) of a Web page for searching for emergency rooms by geographic location in accordance with embodiments disclosed herein.

Upon selecting to search for "Emergency Rooms," such as by selecting the "Search for ERs" button 318 in FIG. 3A, FIG. 4A illustrates an example UI 400 for providing search criteria for an emergency room, in accordance with embodiments disclosed herein. FIG. 4A illustrates that a search for emergency rooms has been selected, as shown by URL address 402 of, for example, "www.healthgrades.com/emergency-care/search." Web page 400 displays Emergency Rooms 404 as the search subject, and a user and/or potential patient is able to search by state and city 406 by selecting a state 408 from a list of states 410. Toggle bar 414 allows more states to be viewed for selection purposes, in which more states are available for selection as shown by ellipses 412. FIG. 4A depicts a user and/or potential patient as selecting Arizona, as shown by the mouse pointer 415 hovering over the state of Arizona, for example. Next, a user and/or potential patient selects a city for the search for emergency rooms. In embodiments, all cities are listed 418. In other embodiments, cities specific to the state selected at 408 are displayed at city selection area 418. For example, Arizona cities are displayed for selection where the state of Arizona is selected, in accordance with embodiments. A toggle bar 419 may also be used to view additional cities available for selection as shown by ellipses 420. Again, a reminder 422 to phone "9-1-1" in case of an immediate need for medical attention is displayed in embodiments.

Figure 4B:
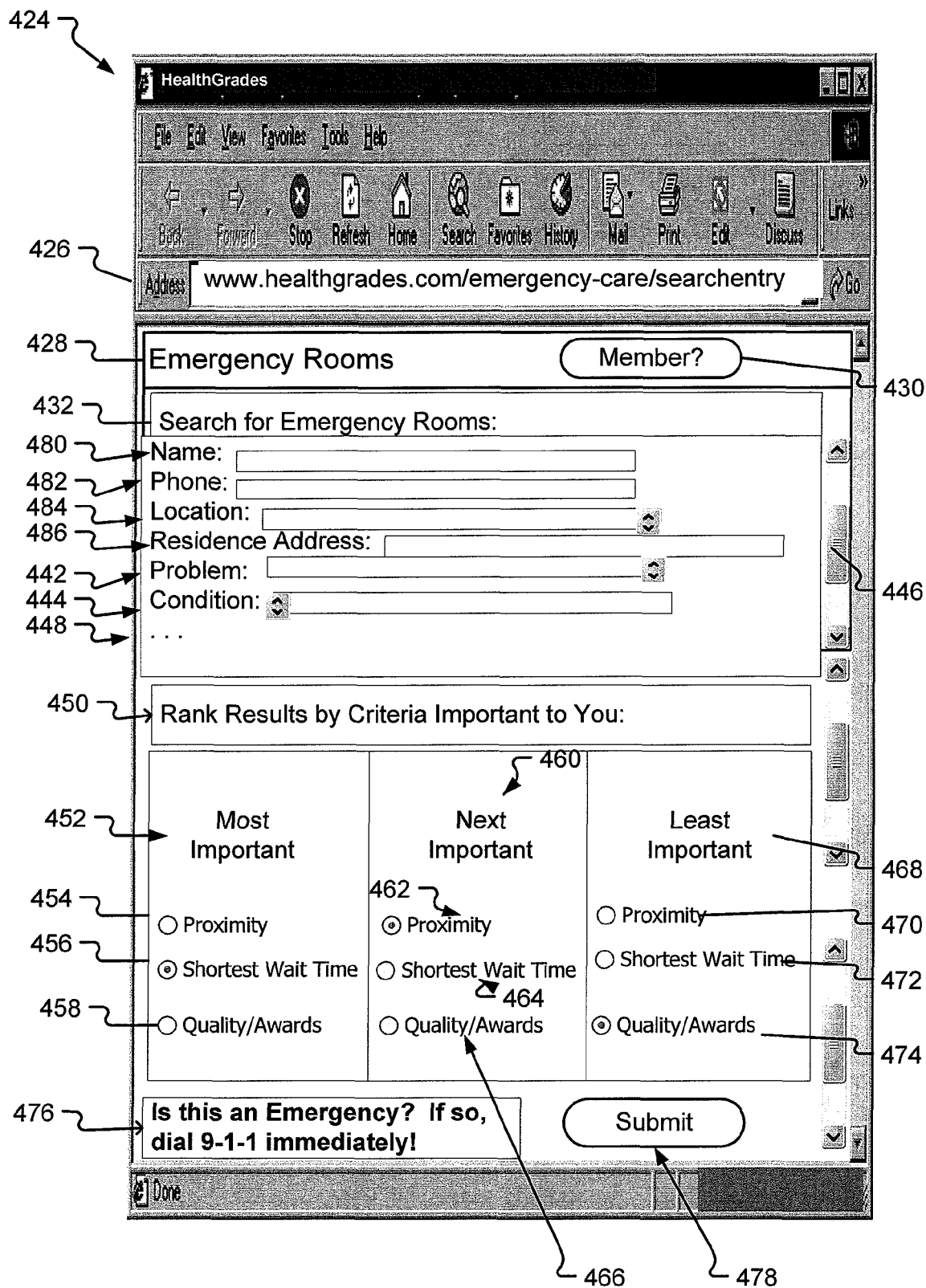
FIG. 4B depicts an example user interface (UI) of a Web page for searching for emergency rooms, for example, by entering search criteria, such as geographic location and medical condition or problem, and priority of search criteria results in accordance with embodiments as disclosed herein.

While FIG. 4A illustrates a Web page for selecting an emergency room by state and city, FIG. 4B depicts Web page 424 for entering further search criteria in accordance with embodiments disclosed herein. Web page 424 may be displayed for entering further search criteria following the selection of a state and city in FIG. 4A in embodiments. In other embodiments, FIG. 4B is the only Web page displayed for entering search criteria for a specific search request by a user and/or potential patient. In yet other embodiments, FIG. 4B is one of a plurality of Web pages displayed for entering search criteria for a particular search request. In an embodiment, Web page 424 is accessed by completing the URL address 426 for the specific page, as shown by the sample URL address of "www.healthgrades.com/emergency-care/search-entry" depicted in FIG. 4B. In another embodiment, Web page 424 is accessed by selecting to search for emergency rooms, for example. Web page 424 indicates that a user and/or potential patient may search for emergency rooms 428 using this Web page. If the user and/or potential patient is affiliated with the company providing the healthcare facility search services, such as by being a member of the service, the user and/or potential patient may indicate their member status by clicking on "Member?" button 430 and then providing log-in information or other identifying information. Next, criteria for searching for emergency rooms 432 is entered by entering text into the text entry boxes for Name 434, Phone 436, Location 438, Residence Address 440, Problem 442, Condition 444, and/or any other fields requesting information as shown by ellipses 448 and toggle bar 446 for displaying any additional areas for text entry. Web page 424 also allows a user and/or potential patient to rank results by the criteria important to the user and/or potential patient 450. For example, a user and/or potential patient may decide to rank shortest wait time 456 as most important as compared to proximity 454 or quality/awards recipients 458. The user and/or potential patient may then decide to rank proximity 462 as next important as compared to shortest wait time 464 and quality awards 466. Next, the user and/or potential patient may choose to rank quality/awards 474 as least important compared to proximity 470 and shortest wait time 472. Embodiments also provide for Web page 424 to offer an additional reminder 476 for the user and/or potential patient to dial "9-1-1" for immediate care, if necessary. Following the entry of the above-identified search criteria, the user and/or potential patient selects, or clicks on, the "Submit" button 478 to submit the search criteria for processing.

In embodiments where a user and/or potential patient indicates that they are a member of the company providing the healthcare facility search services, Web page 424 shows a message indicating the return of the member 428. Further, in embodiments, certain areas of the form are automatically populated with the member information. For example, field 480 now has the name of the member entered into it as, "John A. Smith," for example, with the phone number 482 on record for Mr. Smith. The member's residence address 484 is also automatically populated with the member's address stored in a database and retrieved by a server processing the membership information and form processing. The current address location 486 of Mr. Smith is also shown as having been automatically populated. Such location information 486 may be automatically populated in embodiments, for example, where a navigation satellite system is used to provide the user's current location coordinates. These coordinates are then sent for processing and an address matching the coordinates may be retrieved from a database(s), according to embodiments. Where more than one address matches the coordinates, the location information text entry box has up- and-down arrows 445 to allow the user to choose the correct address for identifying location information 486. Such current location information may be used by the search engine in processing the request to determine the facility within closest proximity of the user and/or potential patient.

Figure 4C:
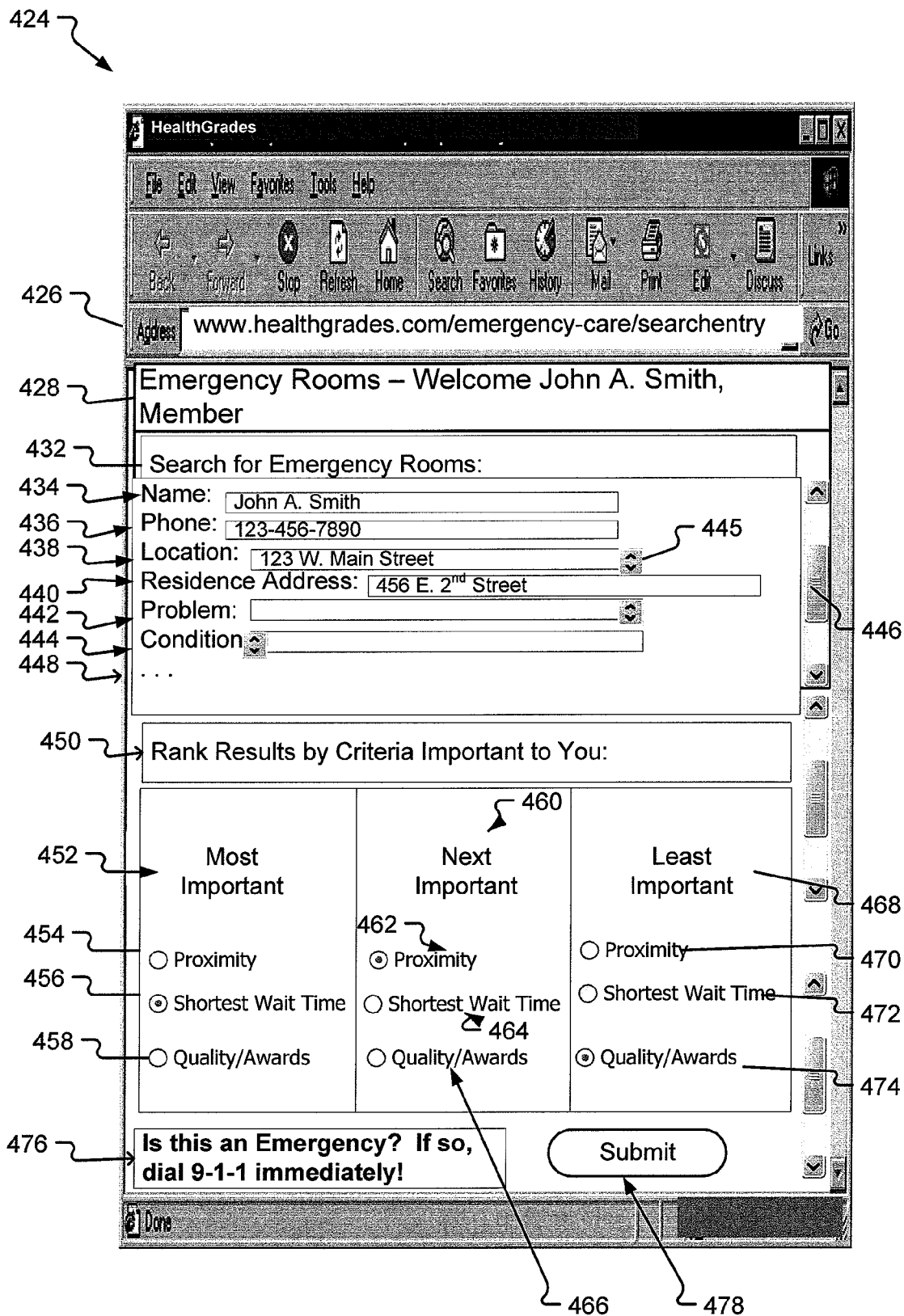
FIG. 4C illustrates an example user interface (UI) with some of the search criteria fields shown in FIG. 4B automatically populated with information/data, such as from data stored in a database for affiliated users, and/or geographic location data from a navigation satellite system in accordance with embodiments disclosed herein.

The user interfaces depicted in FIGS. 4A, 4B and 4C are offered for purposes of illustration only. Any type of user interface can be used in accordance with embodiments disclosed herein. Further, the specific buttons, selectors, arrows, text, etc., are offered by way of example only for purposes of illustration. Any type and arrangement of text, buttons, selectors, headings, and/or other features and functions may be used in accordance with embodiments disclosed herein. Further, any number of sections may be used, in which greater than or fewer than the number of sections depicted may be used in embodiments. Any combination or sub-combination of the sections shown in FIGS. 4A, 4B and 4C may be used, and the sections may be rearranged in any order or layout. In addition, while FIGS. 4A, 4B, and 4C depict searches for emergency rooms, analogous Web pages may be used for searches for urgent care facilities and convenient care facilities. Further yet, while user interfaces 400 and 424 show an indicator of "Microsoft Internet Explorer" and "WWW" in the example depicted, these are offered for purposes of illustration only. For example, an intranet and/or other type of network may be used in accordance with other embodiments.

Figure 5:
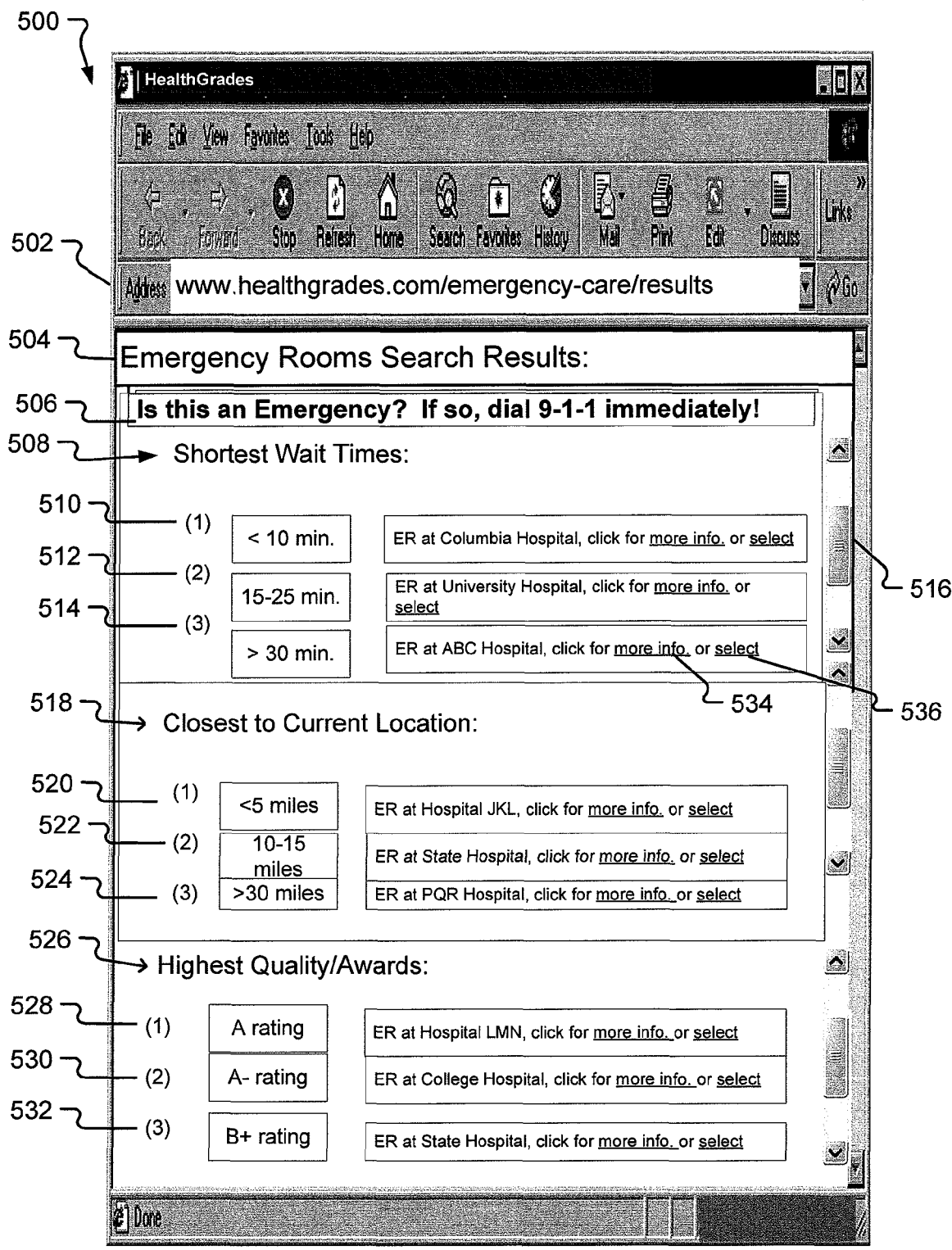
FIG. 5 illustrates an example user interface (UI) of a Web page depicting results of the search for an emergency/urgent/convenient care facility as conducted in FIGS. 4A, 4B, and/or 4C, for example, in accordance with embodiments disclosed herein.

While FIGS. 4A, 4B, and 4C illustrate Web pages for entering or automatically populating search criteria for a search request for a healthcare facility, FIG. 5 depicts an example search results Web page 500, in accordance with embodiments disclosed herein. This search results Web page 500 may be automatically received at a client computer in response to submitting a search request in embodiments. In other embodiments, a user and/or potential patient may enter a URL address 502 for retrieving the results Web page. By way of example only, Web page 500 shows a URL address 502 of "www.healthgrades.com/emergency-care/results." The emergency room search results 504 are provided to the user and/or potential patient with a reminder 506 to dial "9-1-1" if the potential patient requires immediate assistance, according to embodiments. Based on the search criteria provided, Web page 500 displays search results showing first the emergency room facilities in order of the shortest wait times 508. For example, the "ER at Columbia Hospital" is ranked first because it has the shortest wait time of less than ten (10) minutes 510. The next shortest wait time is listed second 512, and the third shortest wait time 514 is listed third. In embodiments where the search results list more than the number of facilities in view, toggle bar 516 may be used to view additional results.

Next, the search results are ranked in terms of closest proximity to the user's and/or potential patient's current location, in which the emergency room at Hospital JKL, for example purposes only, is listed first as having the shortest distance 520, followed by the emergency room with the next shortest distance 522, and finally the third emergency room with the next shortest distance 524. Finally, the results are provided to the user according to the ratings of the facilities in terms of quality/awards received. For example, the emergency room at Hospital LMN, for example purposes only, is listed first 528 with an "A" rating, followed by the emergency room with the next highest rating 530, and followed next by the emergency room with the next highest rating 532. With the search results of FIG. 5 provided to the user and/or potential patient, the user and/or potential patient may make an informed decision regarding his/her choice of emergency room facility. The user and/or potential patient may use the search results Web page 500 to obtain more information 534 on a particular facility listed, and/or select 536 a particular facility to submit a notification of requesting admittance to.

The user interface depicted in FIG. 5 is offered for purposes of illustration only. Any type of user interface can be used in accordance with embodiments disclosed herein. Further, the specific buttons, selectors, arrows, text, headings, etc., are offered by way of example only for purposes of illustration. Any type and arrangement of text, buttons, selectors, and/or other features and functions may be used in accordance with embodiments disclosed herein. Further, any number of sections may be used, in which greater than or fewer than the number of sections depicted may be used in embodiments. Any combination or sub-combination of the sections shown in FIG. 5 may be used, and the sections may be rearranged in any order or layout. Further, the search results may be displayed in multiple search results Web pages, in accordance with other embodiments, such as a Web page for search results for shortest wait times and another Web page for search results for closest proximity, etc. In addition, while FIG. 5 depicts search results for emergency rooms, analogous Web pages may be used for search results for urgent care facilities and convenient care facilities. Further yet, while user interface 500 shows an indicator of "Microsoft Internet Explorer" and "WWW" in the example depicted, these are offered for purposes of illustration only. For example, an intranet and/or other type of network may be used in accordance with other embodiments.

Figure 6:
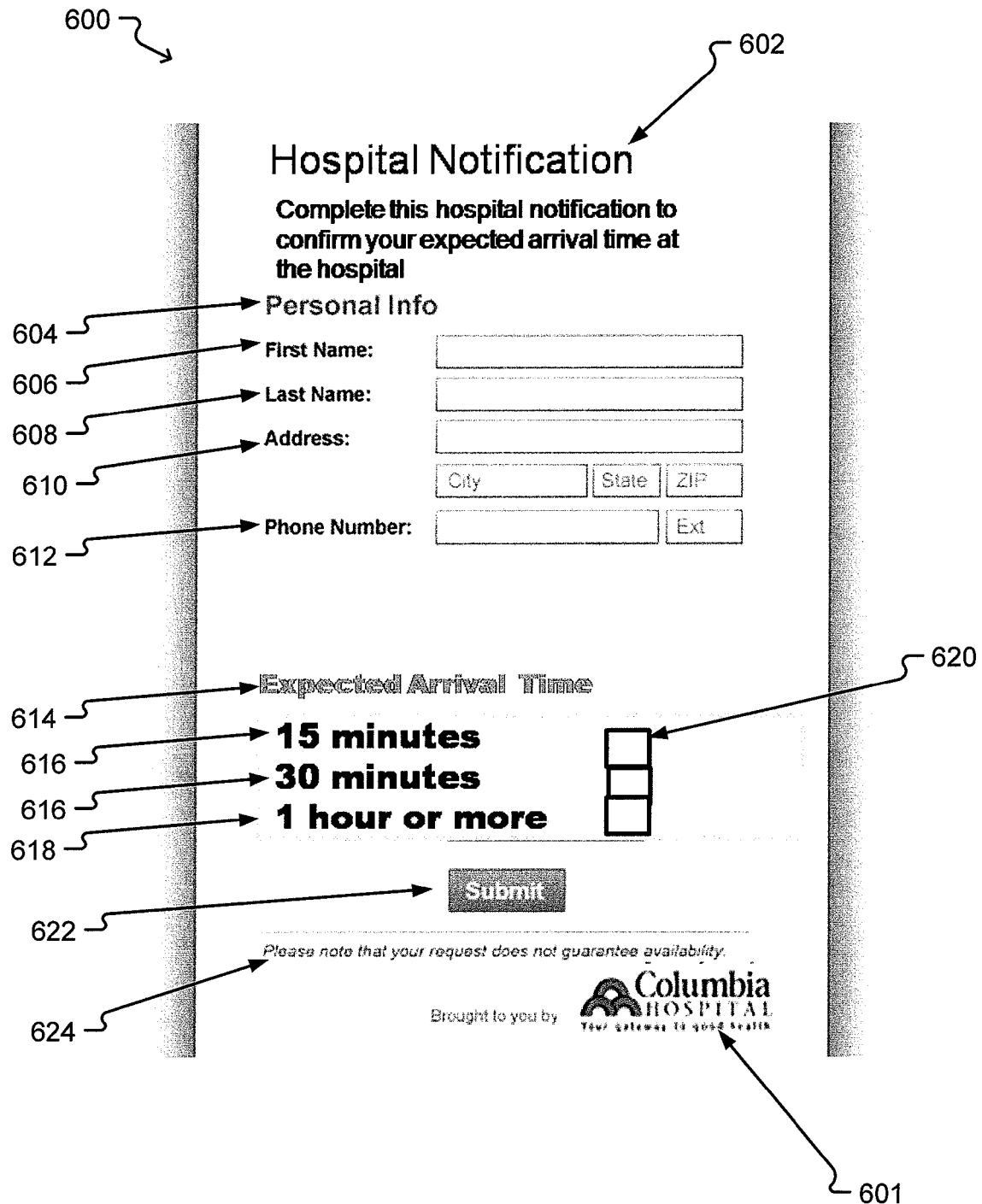
FIG. 6 depicts an example user interface (UI) of a Web page for providing, by a user, notification to an emergency/urgent/convenient care facility of the user's desire to be admitted to the facility for treatment in accordance with embodiments disclosed herein.

Turning to FIG. 6, notification form 600 is presented in embodiments to a user and/or potential patient for enabling the user and/or potential patient to send a request to confirm the potential patient's expected arrival at the particular facility, according to embodiments. Notification form 600 is presented in embodiments to a user and/or potential patient in response to the user's and or potential patient's selection of the particular facility, such as by clicking on "select" 536 in FIG. 5, for example. The particular facility selected 601 is displayed on notification form 600, according to embodiments, to make sure the user and/or potential patient is submitting the form for the desired facility. In response to a selection, Hospital Notification form 602 is displayed, in which the personal information 604 of the potential patient is requested, including, for example, the patient's first name 606, last name 608, address 610, and phone number 612. In embodiments, notification form 600 also allows the user and/or potential patient to indicate the expected arrival time 614, such as checking a box 616 for arriving in 15 minutes 618, 30 minutes 620, or 1 hour or more 622, for example. Upon completing notification form 600, the user and/or potential patient may select the "Submit" button 624. While notification form 600 allows the user and/or potential patient to indicate his/her intended arrival at the particular facility, reminder 626 reminds the user and/or potential patient that the request does not guarantee availability. Rather, the notification form is sent to the facility for processing and response, according to embodiments.

The form depicted in FIG. 6 is offered for purposes of illustration only. Any type of form can be used in accordance with embodiments disclosed herein. Further, the specific buttons, selectors, text entry boxes, text, headings, etc., are offered by way of example only for purposes of illustration. Any type and arrangement of text, checkboxes, buttons, selectors, text entry boxes, and/or other features and functions may be used in accordance with embodiments disclosed herein. Further, any number of requests for information may be used, in which greater than or fewer than the number of text entry boxes and/or checkboxes depicted may be used in embodiments. Any combination or sub-combination of the sections/text entry boxes, etc. shown in FIG. 5 may be used, and the sections/text entry boxes, etc. may be rearranged in any order or layout. Further, the notification form may be displayed in a plurality of pages, in accordance with other embodiments, such as a page for personal information and another page for expected arrival time, etc. In addition, while FIG. 6 depicts a "Hospital" notification, it is to be understood that a notification form may be used for any type of healthcare facility, in accordance with embodiments.

Figure 7A:
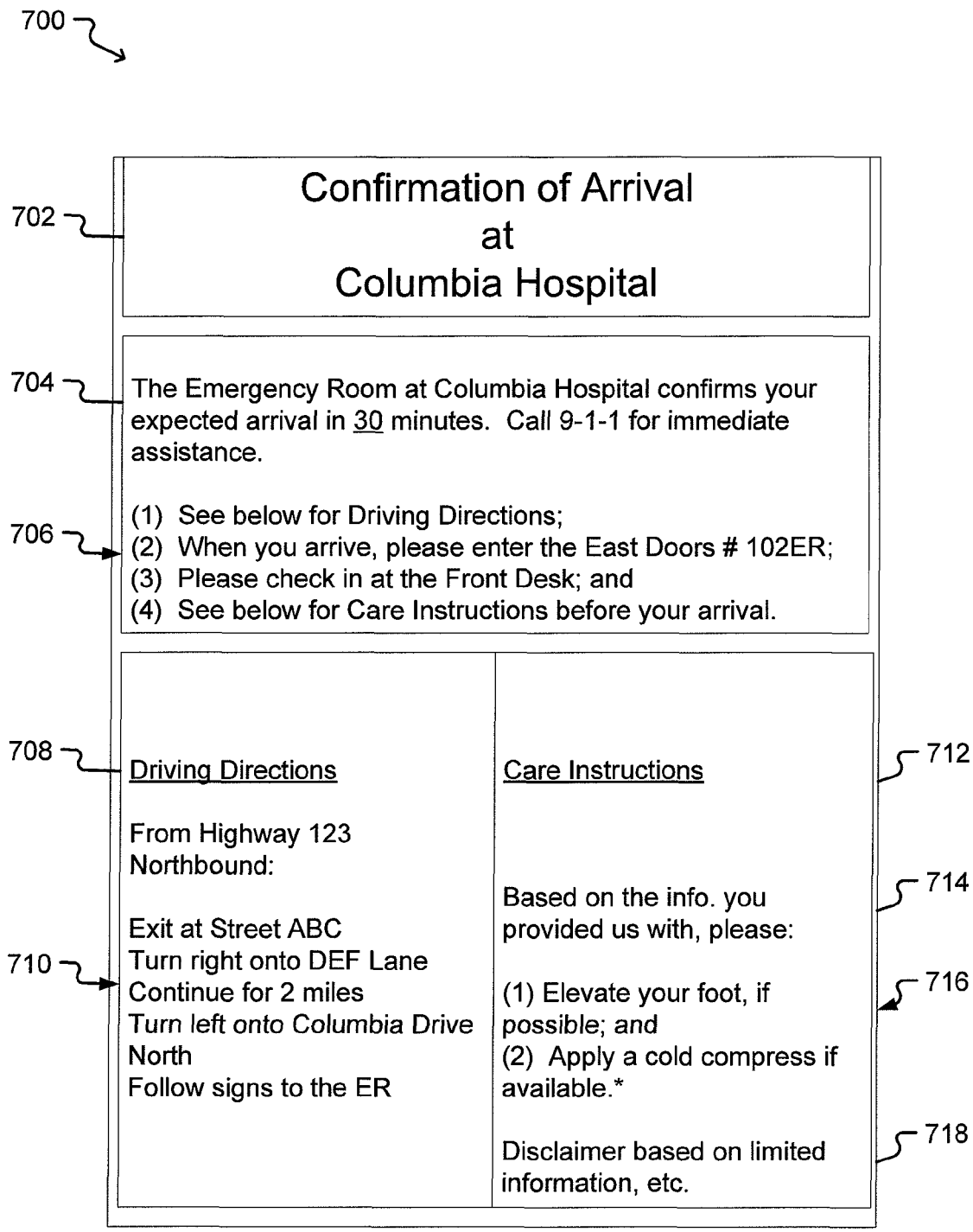
FIG. 7A illustrates an example user interface (UI) of a Web page showing confirmation by the emergency/urgent/convenient care facility of the ability to admit the potential patient in response to the notification received from the user in FIG. 6 in accordance with embodiments disclosed herein.
Figure 7B:
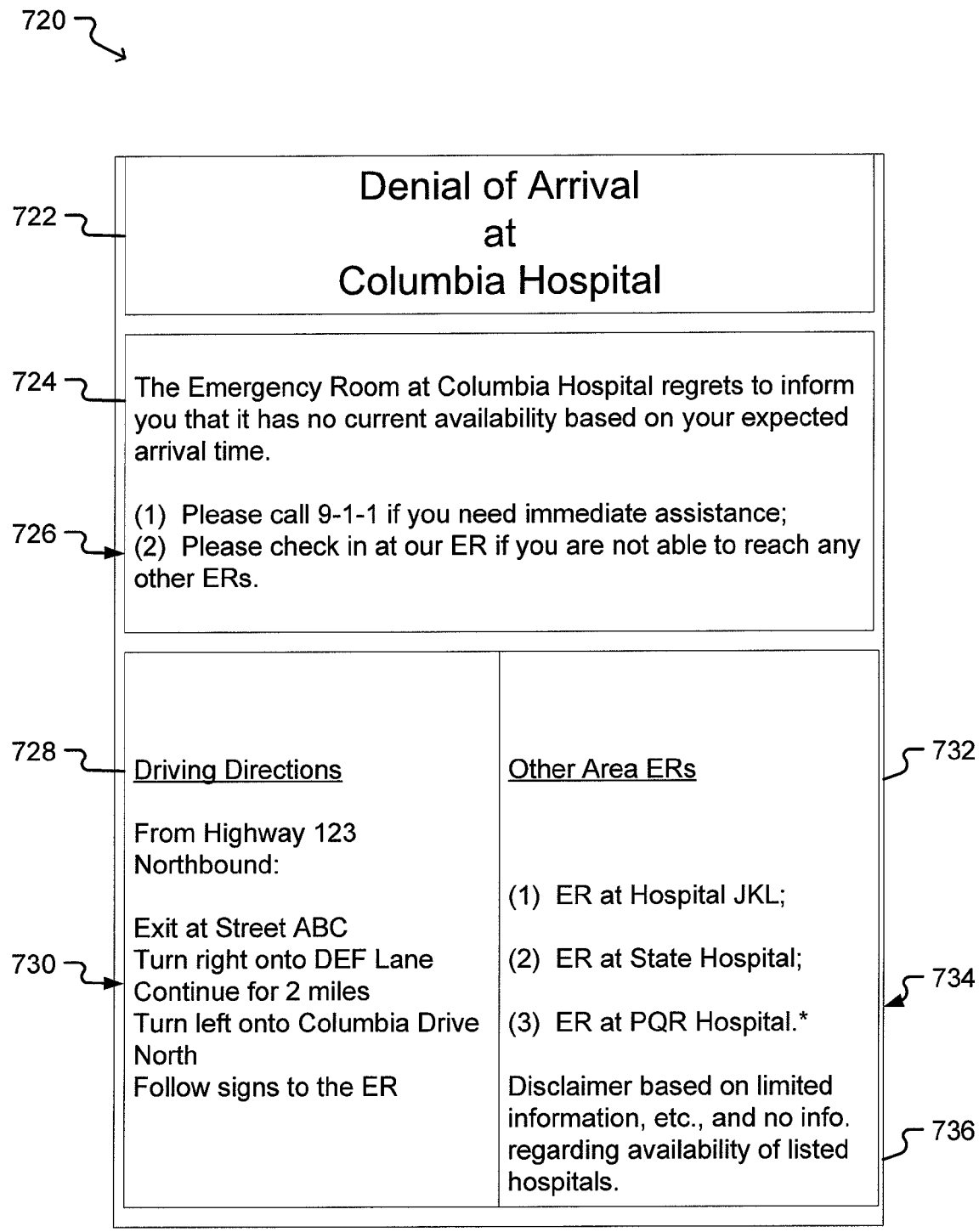
FIG. 7B depicts an example user interface (UI) of a Web page showing denial by the emergency/urgent/convenient care facility of the request for treatment in response to the notification received in FIG. 6 in accordance with embodiments disclosed herein.

While FIG. 6 illustrates a hospital notification form to indicate a potential patient's expected arrival, FIGS. 7A and 7B depict a confirmation of arrival response 700 and a denial of arrival response 720, according to embodiments. Starting with FIG. 7A, confirmation of arrival response 700 confirms the facility's ability to accept the potential patient as a patient for treatment 702. In an embodiment, the confirmation of the expected arrival time 704 is also given. A reminder 704 to phone "9-1-1" for any needed immediate assistance is also listed, in accordance with embodiments. Further, a list of instructions 706 is provided for the potential patient, including, for example, check-in instructions, etc. Embodiments also provide for driving directions 708 to be provided, in which sample driving directions 710 are displayed in response 700. Care instructions 712 while en route to the facility are also provided in accordance with embodiments. For example, care instructions 712 are given based on the information received by the facility 714, in which sample instructions are listed 716. To protect the facility from liability associated with such care instructions, a disclaimer 718 is provided in an embodiment.

Turning to FIG. 7B, a denial of arrival response 720 is sent to the user and/or potential patient in embodiments where the selected facility is not able to admit the potential patient 722. In embodiments, the facility indicates it has no current availability to admit the potential patient 724. In further embodiments, response 720 indicates to dial "9-1-1" if immediate assistance is required 726 or to check in at the particular emergency room if the potential patient is not able to get to or be seen by any other emergency room 726. Driving directions 728 are included in embodiments (such as where the emergency room indicates that the potential patient may be admitted if no other ERs are available or within reach). According to further embodiments, other area emergency rooms 732 are listed to assist the potential patient or user in finding another emergency room, such as from list 734. A disclaimer 736 is also provided in an embodiment.

Figure 8:
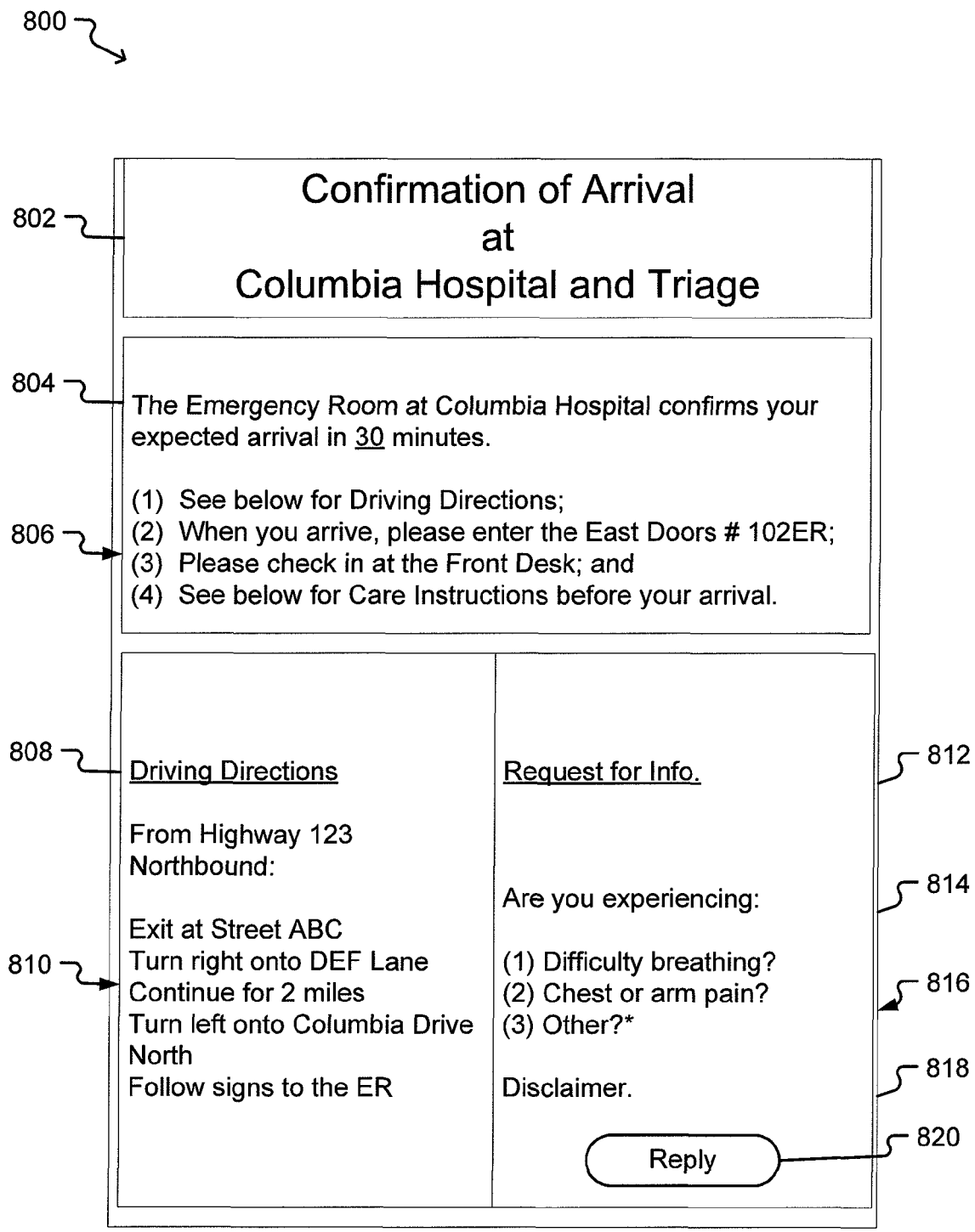
FIG. 8 illustrates an example user interface (UI) of a Web page depicting further information requested by the care facility, such as for conducting triage before the potential patient's arrival, in accordance with embodiments disclosed herein.

While FIG. 7A illustrates a confirmation of arrival response from the selected facility, FIG. 8 depicts a confirmation of arrival response with a request for further information 800, in accordance with embodiments. Response 802 indicates both a confirmation of the facility's ability to accept the potential patient, as well as provides a request for information. Such further information may be used for triage purposes 802 by the facility, according to embodiments. Response form 800 confirms the patient's expected arrival time 804, as well as provides instructions 806 in embodiments. Driving directions 808, such as example directions 810, may also be provided. In further embodiments, a request for information 812 is made. For example, the request may ask further questions regarding the potential patient's medical condition 814, such as, for example, if the patient is having difficulty breathing, experiencing chest or arm pain, or any other medical questions 816. These medical conditions are offered for purposes of illustration only. A disclaimer 818 is also provided in embodiments. To reply to the questions 814, the user and/or potential patient may click on, or otherwise select, the "Reply" button 820. In an embodiment, upon selecting the "Reply" button 820, a form appears (not shown) allowing the user and/or potential patient to answer the questions through, for example, checking checkboxes, selecting radio buttons, entering text in text entry boxes, etc. In another embodiment, the user and/or potential patient may reply to the questions directly on the response form and then select a "Submit" button, for example, to submit the responses for processing. By providing answers to the facility's further questions, the facility may use the information to triage the patient before his/her arrival. Such ability promotes efficiency and leads to overall improved care by accelerating the procedures for treating patients.

The response forms depicted in FIGS. 7A, 7B, and 8 are offered for purposes of illustration only. Any type of form can be used in accordance with embodiments disclosed herein. Further, the specific sections, headings, etc. are offered by way of example only for purposes of illustration. Any type and arrangement of headings, sections, text, content, etc. may be used in accordance with embodiments disclosed herein. Further, any type of content may be used in embodiments, and any combination or sub-combination of the sections, headings, content, text, etc. may be used and rearranged in any order or layout. Further, each of the confirmation and denial responses may be displayed in a plurality of pages, in accordance with other embodiments, such as having multiple pages confirming arrival with content related thereto and/or multiple pages denying arrival with content related thereto. In addition, while FIGS. 7A, 7B, and 8 depict responses for a particular "hospital," the names listed are for example purposes only, and it is to be understood that a notification form response may be provided for any type of healthcare facility, in accordance with embodiments.

Figure 9A:
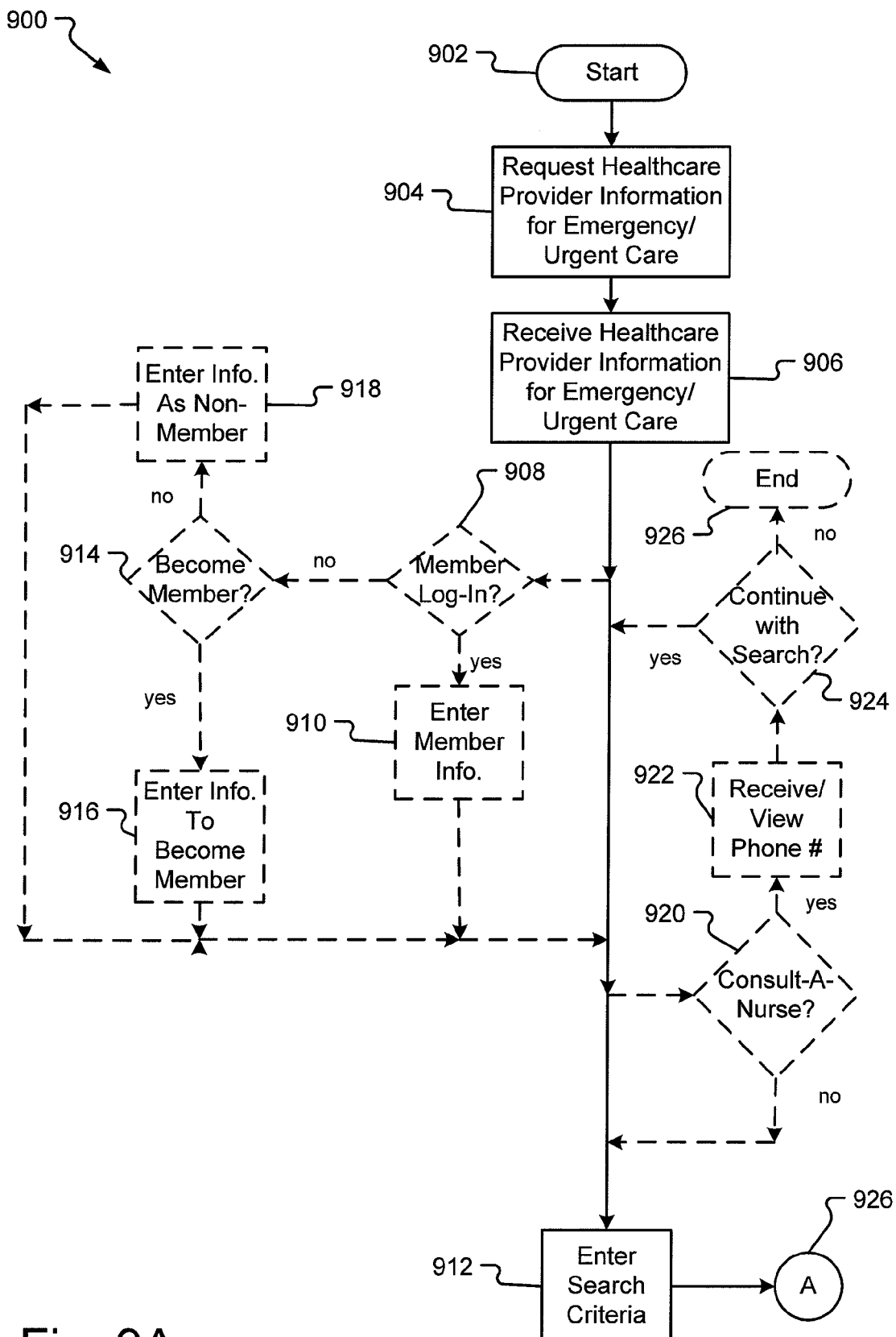
FIG. 9A depicts a flow diagram illustrating the operational characteristics of a process for searching for an emergency/urgent/convenient care facility, selecting a facility based on search results, sending notification of arrival and providing triage information in accordance with embodiments disclosed herein.
Figure 9B:
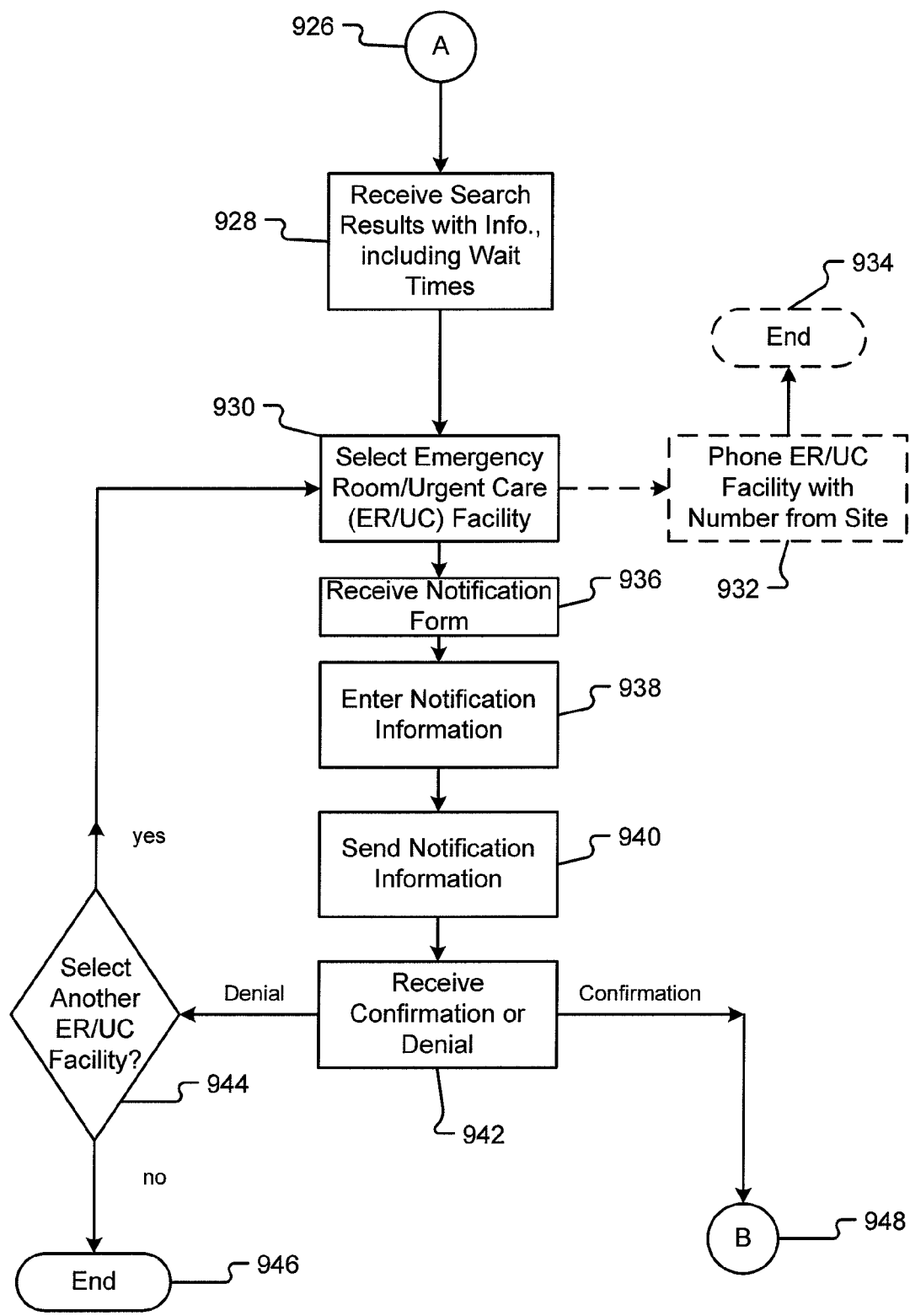
FIG. 9B illustrates a flow diagram illustrating the operational characteristics of a process for searching for an emergency/urgent/convenient care facility, selecting a facility based on search results, sending notification of arrival and providing triage information in accordance with embodiments disclosed herein.
Figure 9C:
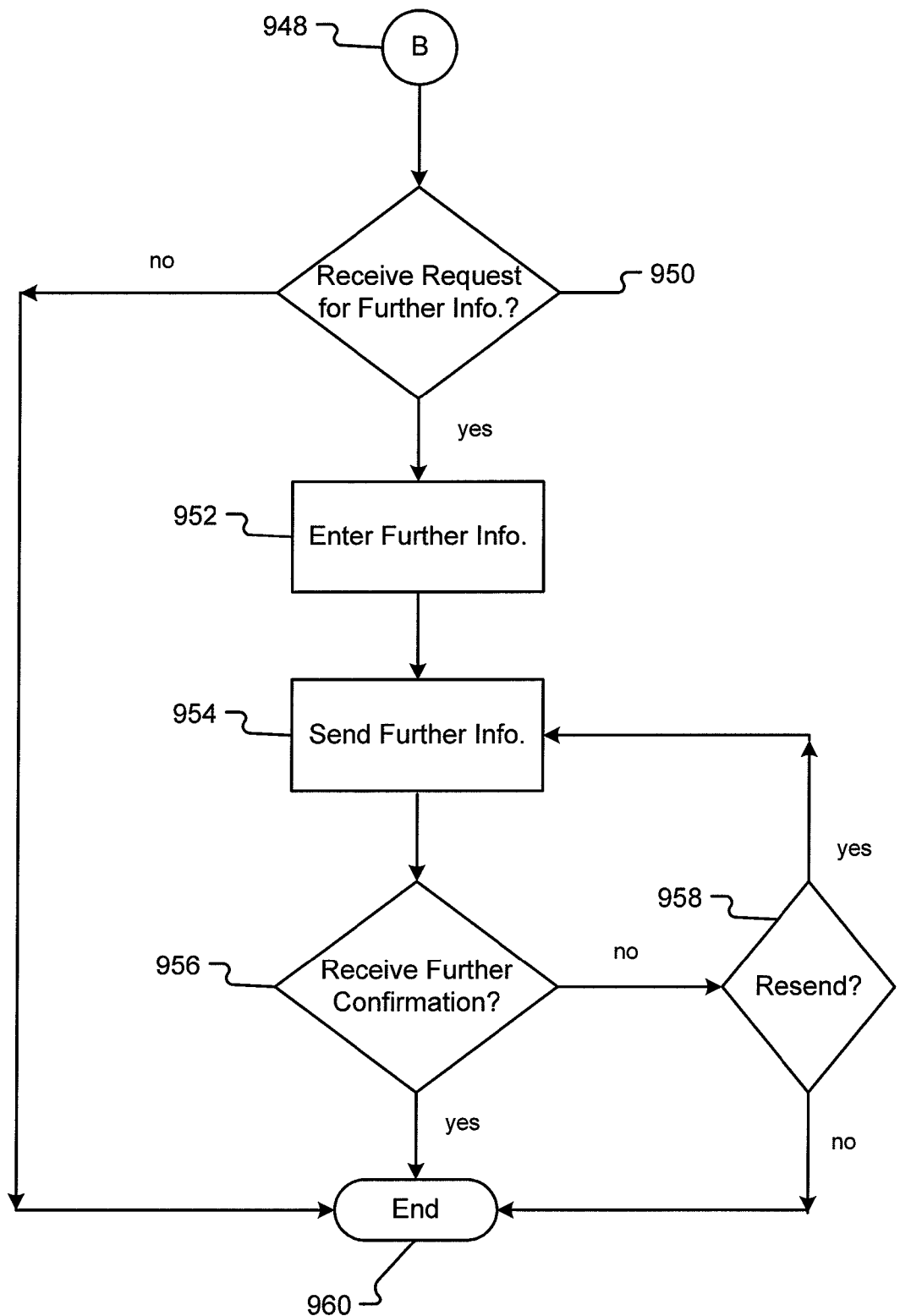
FIG. 9C depicts a flow diagram illustrating the operational characteristics of a process for searching for an emergency/urgent/convenient care facility, selecting a facility based on search results, sending notification of arrival and providing triage information in accordance with embodiments disclosed herein.

The interactions of the various functionalities depicted in the user interfaces and forms described above are further illustrated in the operational steps depicted in FIGS. 9A, 9B, and 9C in accordance with embodiments disclosed herein. START operation 902 is initiated, and process 900 proceeds to request healthcare provider information for a care facility 904, such as an emergency room, convenient care facility, and/or urgent care facility. While the applicable steps in FIGS. 9A through 9C depict "Emergency/Urgent Care," it is to be understood that any type of care facility is intended to be covered by these operational steps, including convenient care facilities, for example. Such a request 904 for healthcare provider information may be made by a user and/or potential patient, for example, from a client computer, mobile device, mobile phone, etc. Next, healthcare provider information for care facilities is received 906. Such information, for example, may include information regarding descriptions of each of the types of facilities, the types of medical conditions treated by each of the facilities, etc. Following step 906, process 900 may optionally (as shown by dashed lines) first proceed to member log-in query 908, in which it is determined whether the user and/or potential patient has indicated their status as a member of the company providing the healthcare facility search services. If query 908 determines that the user and/or potential patient is a member, process 900 proceeds YES to enter member information 910, in which the user and/or potential patient is prompted to enter information identifying himself/herself as a member. If query 908 determines that the user and/or potential patient is not a member, process 900 proceeds NO to query 914 to determine whether the user and/or potential patient would like to become a member. Where the user and/or potential patient does not desire to become a member, process 900 proceeds NO to enter information as a non-member step 918, in which the user and/or potential member provides their name and/or other information. Where the user and/or potential patient desires to become a member, process 900 proceeds YES to enter information to become a member 916. Where the user and/or potential patient is in a hurry, embodiments provide for abbreviated information to be entered to become a member with the option to add supplemental information at a later time. Following these steps, process 900 may optionally (as shown by dashed liens) proceed to query 920, in which the user and/or potential patient may decide to directly consult a medical practitioner, such as through the "Consult-A-Nurse" service, for example. Where the user and/or potential patient desires to consult a medical practitioner, process 900 proceeds YES to receive phone number or view phone number 922 (or other contact means) for reaching the service. After receiving and/or viewing the phone number or other contact means, in which the user and/or potential patient may contact the medical practitioner service, process 900 proceeds to query 924 to determine whether the user and/or potential patient would like to continue with searching 924. Where the user and/or potential patient desires to continue with searching 924, process 900 proceeds YES to enter search criteria 912. Where no searching is desired, process 900 proceeds NO to end operation 926, and process 900 terminates. Alternatively, where the user and/or potential patient does not desire to consult a medical practitioner 920, process 900 proceeds NO to enter search criteria 912, in which the user and/or potential patient provides search criteria for conducting a search for a healthcare facility.

Next, process 900 continues through off-page connector A 926 to receive search results 928. In an embodiment, such search results comprise information such as wait times at facilities, closest geographic or physical proximity to the potential patient's current location, quality/awards ratings, etc. Following the receipt of search results 928, process 900 proceeds to select care facility 930, in which the user and/or potential patient indicates a selection of a particular facility. Process 900 may optionally (as shown by dashed lines) proceed to step 932 for phoning the selected facility with a phone number provided from the Web page(s) providing search results, for example. The provided phone number may be used to track use of the search capabilities of the Web site, according to embodiments. Other contact means, such as email address or SMS address, are provided in other embodiments. Where the user and/or potential patient contacts the facility directly, process 900 terminates at END operation 934. Where direct phoning is not performed, process 900 proceeds to receive notification form 936, in which the user and/or potential patient receives a notification form. Such notification form includes the name of the selected facility in embodiments. In other embodiments, the notification form is a generic form requiring the user and/or potential patient to fill-in the desired facility. The user and/or potential patient enters information on the notification form 938 and sends 940 the notification form for processing. Following the processing of the notification form, the user and/or potential patient receives confirmation or denial of the request to arrive at the facility 942. Where the request is denied, process 900 proceeds to query 944 to determine if the user and/or potential patient would like to select another facility. Where the user and/or potential patient desires to select another facility, process 900 proceeds YES to select facility 930 and steps 930-942 repeat. Where there is no desire to select another facility, process 900 proceeds NO to END operation 946, and process 900 terminates.

In embodiments where the request is approved or confirmed, process 900 continues through off-page connector B 948 to receive request for further information query 950. Such request for further information is sent with the confirmation response in embodiments. In other embodiments, the request is sent separately from the confirmation response. In an embodiment, such further information allows the facility to triage the potential patient before his/her arrival at the facility, according to embodiments. In another embodiment, such further information is requested before the facility confirms or approves the potential patient's requested arrival. Where a request for further information is made, process 900 proceeds YES to enter or provide further information 952, and such information is sent 954 for processing. Next, process 900 proceeds to query 956 for determining whether a further confirmation is received from the facility in response to sending of the further information. Where no further confirmation is received, process 900 proceeds NO to query 958 to determine whether to resend the further information. Where it is desired to resend the further information, process 900 proceeds YES to send further information 954 and steps 954 and 956 repeat. Where it is not desired to resend the further information, process 900 proceeds NO to END operation 960, and process 900 terminates. In an embodiment where it is determined that a further confirmation is received at determination step 956, process 900 proceeds YES to END operation 960, and process 900 terminates.

FIGS. 9A, 9B, and 9C are an example of possible operational characteristics for searching for an emergency/urgent/convenient care facility, selecting a facility based on search results, sending notification of arrival and providing triage information in accordance with embodiments disclosed herein. Operational steps depicted may be combined into other steps and/or rearranged. Further, fewer or additional steps may be used, for example.

Figure 10A:
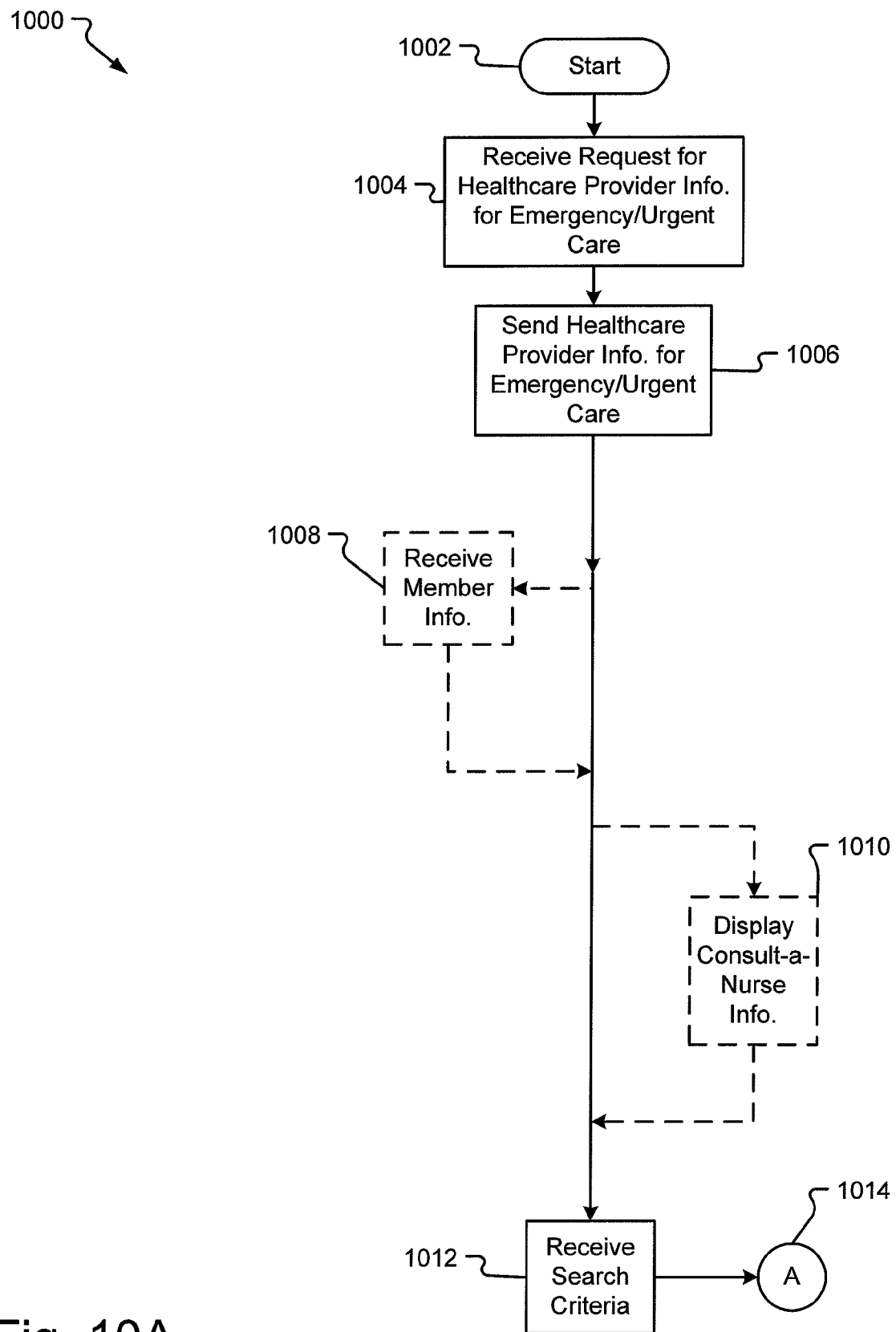
FIG. 10A illustrates a flow diagram depicting the operational characteristics of a process for receiving a request for an emergency/urgent/convenient care facility, processing the search criteria to provide results, transmitting notifications of arrival and confirmation/denial thereof, and relaying triage information in accordance with embodiments disclosed herein.
Figure 10B:
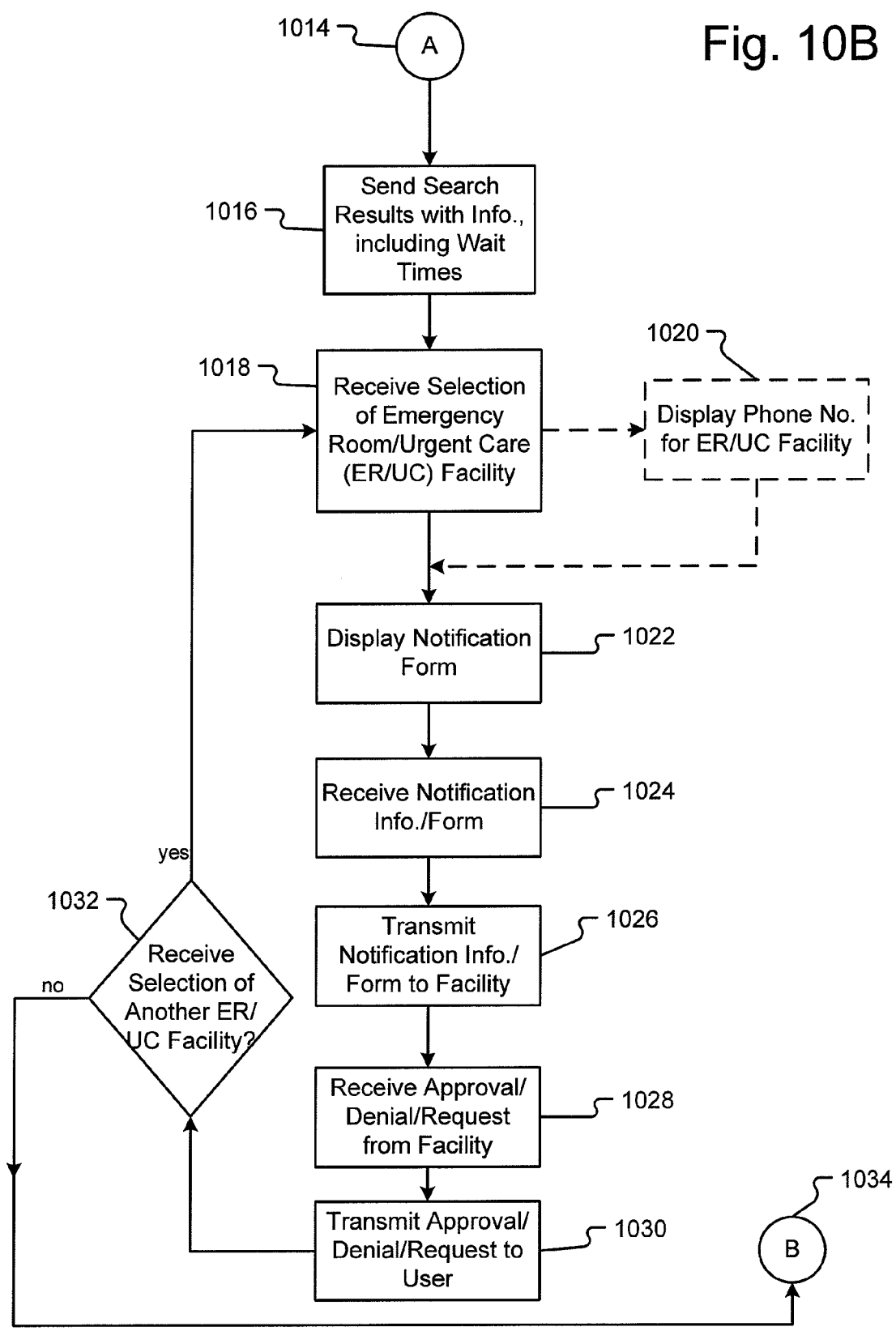
FIG. 10B illustrates a flow diagram depicting the operational characteristics of a process for receiving a request for an emergency/urgent/convenient care facility, processing the search criteria to provide results, transmitting notifications of arrival and confirmation/denial thereof, and relaying triage information in accordance with embodiments disclosed herein.
Figure 10C:
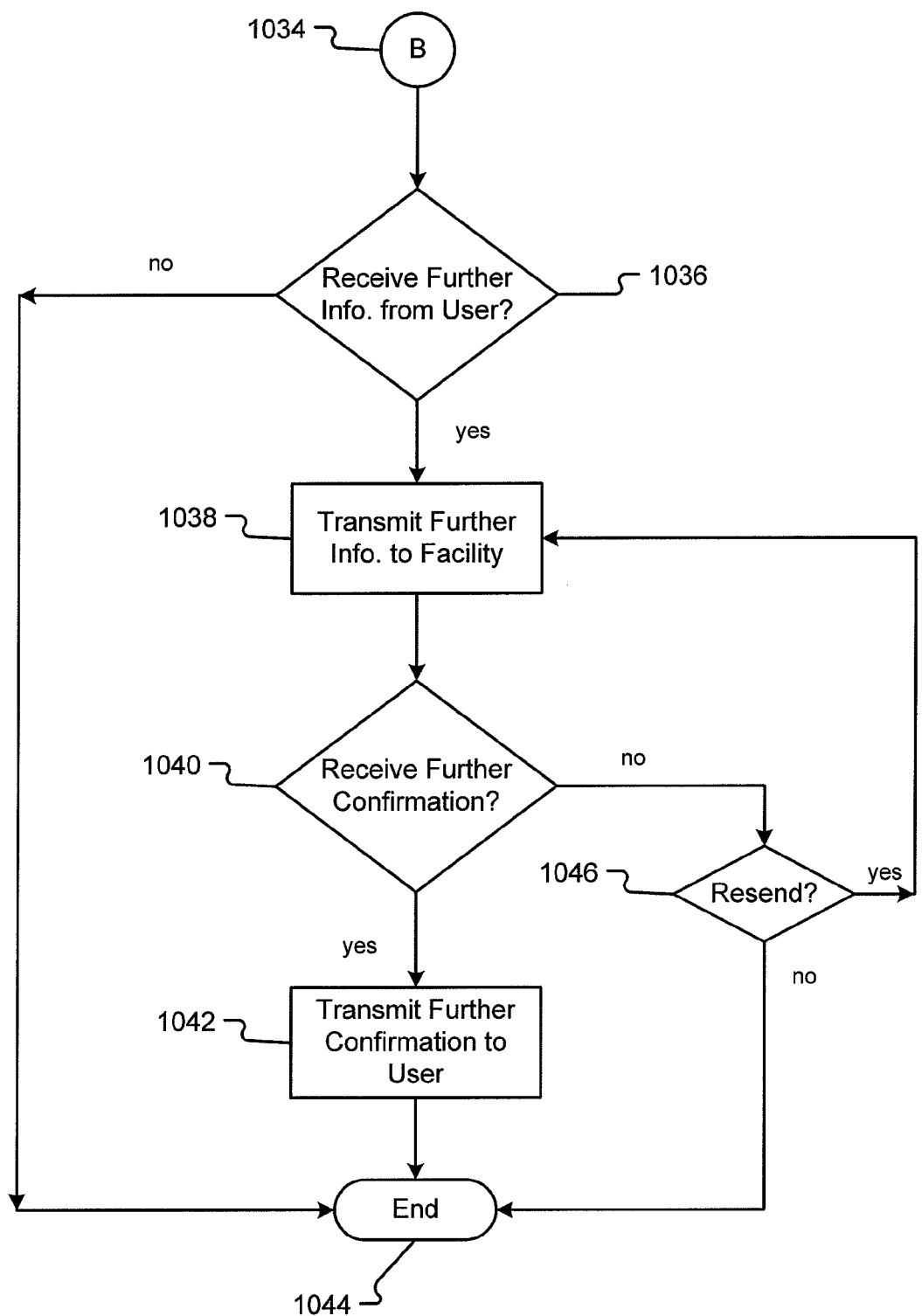
FIG. 10C illustrates a flow diagram depicting the operational characteristics of a process for receiving a request for an emergency/urgent/convenient care facility, processing the search criteria to provide results, transmitting notifications of arrival and confirmation/denial thereof, and relaying triage information in accordance with embodiments disclosed herein.

While FIGS. 9A, 9B, and 9C illustrate example operational characteristics for searching for a care facility by a user and/or potential patient, for example, FIGS. 10A, 10B, and 10C depict example operational characteristics for processing a search request and providing results related thereto, in accordance with embodiments disclosed herein. START operation 1002 is initiated, and process 1000 proceeds to receive request for healthcare provider information for emergency, convenient, and/or urgent care. Such request is received by a server(s) of a company providing the healthcare facility search services in embodiments. In response to such a request, process 1000 transmits or sends healthcare facility information for emergency, urgent care, and/or convenient care. Such information comprises descriptions of such facilities, types of medical conditions treated at such facilities, etc., according to embodiments. Process 1000 may then optionally (as shown by dashed lines) proceed to optional step 1008 for receiving membership information in embodiments where the user and/or potential patient is a member of, or otherwise affiliated with, the company providing the healthcare facility search services. Process 1000 also may optionally (as shown by dashed lines) proceed to optional step 1010 for displaying information for contacting a medical practitioner directly for information, advice, opinions, etc. In an embodiment, such a medical practitioner service is the "Consult-A-Nurse" service, for example. Process 1000 next proceeds to receive search criteria, in which a search request for an emergency, urgent care, and/or convenient care facility is received.

Next, process 1000 continues through off-page connector A 1014 to send search results 1016. In an embodiment, search results are sent or transmitted after processing of the search request, in which such processing comprises retrieving information and/or data from a database(s) for address information, member profiles, facility listings, facility ratings, facility awards, facility quality ratings, etc., processing such information and/or data, and/or communicating with a facility or a plurality of facilities to determine current wait times, availabilities, etc. In embodiments, communications with a facility or plurality of facilities occurs directly between servers, while other embodiments provide for retrieving of current wait times, current availabilities, etc. from intermediary services, databases, or temporary storage means, for example.

Following the transmittal of search results 1016, process 1000 continues to receive a selection of a facility 1018. Process 1000 may then optionally (as shown by dashed lines) proceed to display phone number for the selected facility 1020, in which such phone number may allow for tracking to indicate that such number was obtained from the particular company Web site. In another embodiment, contact means other than a phone number are displayed, such as an email address, SMS address, etc. Process 1000 next proceeds to display notification form 1022, and information and/or data is received with respect to the notification form at step 1024. This information and/or data and/or the form itself, according to various embodiments, is then transmitted to the facility 1026 or to intermediary servers or other processing means, such as another company service in an embodiment, in communication with the selected facility. After the processing of the request, an approval or denial of the request is received 1028. In an embodiment, a request for further information is received 1028. Next, the approval/denial/request for further information is transmitted or sent to the user and/or potential user 1030. Query 1032 then determines whether a selection is received for another facility. Where a selection for another facility is received, process 1000 proceeds YES to step 1018 and steps 1018-1032 repeat.

Where no further selection is received, process 1000 proceeds NO through off-page connector 1034 to query 1036, in which it is determined whether further information is received from the user and/or potential patient 1036. In an embodiment, such further information is received where the user and/or potential patient responds to a request for further information from the facility. In another embodiment, such further information is provided by the user and/or potential patient without prompting. Where it is determined that further information is received, process 1000 proceeds YES to transmit further information to the facility 1038, in which such information may be transmitted directly to the facility in an embodiment. In another embodiment, such information is transmitted to an intermediary server or service communicating with the facility, for example. Query 1040 next determines whether a confirmation of receipt of the further information is received from the facility 1040. Where a confirmation is received, process 1000 proceeds YES to transmit the further confirmation to the user and/or potential user 1042, and process 1000 terminates at END operation 1044. Where no further confirmation is received, process 1000 proceeds NO to query 1046 to determine whether to resend the further information. Where it is desired to resend the information, process 1000 proceeds YES to 1038, and steps 1038-1040 repeat. Where it is not desired to resend the information, process 1000 proceeds NO to END operation 1044, and process 1000 terminates. Further, in the embodiment where no further information is received from the user and/or potential patient, process 1000 proceeds NO to END operation 1044, and process 1000 terminates.

FIGS. 10A, 10B, and 10C are an example of possible operational characteristics for searching for an emergency/urgent/convenient care facility, selecting a facility based on search results, sending notification of arrival and providing triage information in accordance with embodiments disclosed herein. Operational steps depicted may be combined into other steps and/or rearranged. Further, fewer or additional steps may be used, for example.

Figure 11:
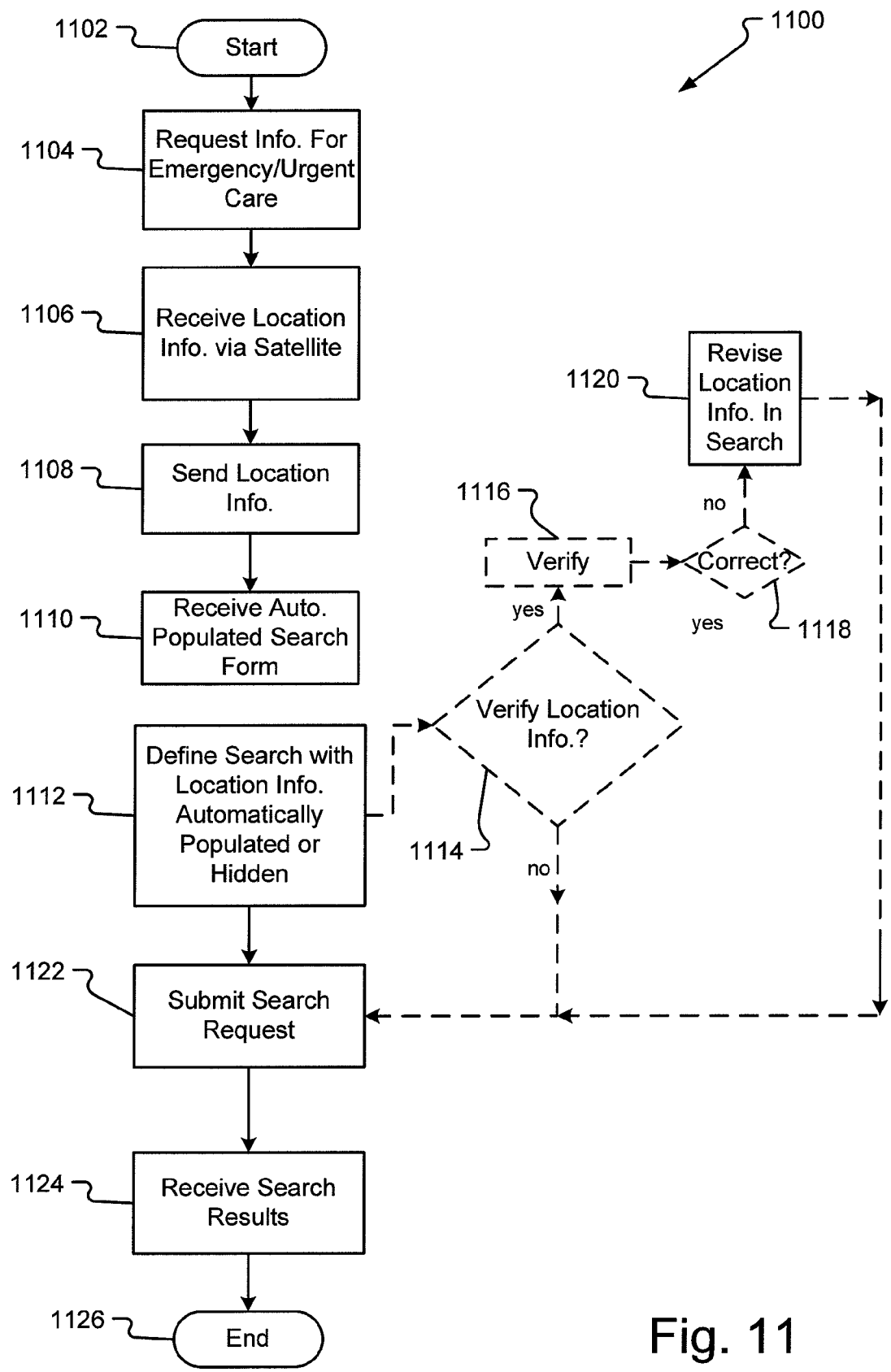
FIG. 11 illustrates a flow diagram showing the operational characteristics of a process for providing search criteria through the use of a navigation satellite system for an emergency/urgent/convenient care facility in accordance with embodiments disclosed herein.

Turning to FIG. 11, this figure illustrates example operational characteristics of a process for receiving current location information through a location system, in accordance with embodiments disclosed herein. START operation 1102 is initiated, and process 1100 proceeds to request information for healthcare facilities, such as emergency, urgent care, and/or convenient care facilities. In an embodiment, the user and/or potential patient is using a mobile device, for example. Next, the mobile device receives location information via a location system 1106. In an embodiment, the location information is received from a navigation satellite system, such as the Global Positioning System, for example. The location information comprises geographic coordinates in embodiments. In another embodiment, the location information is received through triangulation through a cellular network. In embodiments, the location information is sent over a network 1108 to a server(s) for processing. Next, a search Web page with an automatically populated address for the user's and/or potential patient's current locations is received 1110. In an embodiment, the address information is automatically populated but hidden from view. In another embodiment, the address information can be viewed by the user and/or potential patient. The user and/or potential patient then defines a search 1112. Process 1100 may then optionally (as shown by dashed lines) proceed to query 1114 to determine if the user and/or potential patient desires to verify the location information automatically populated on the search form. For example, the user and/or potential patient may desire to confirm that the address of the user's and/or potential patient's current location is correct. If the user and/or potential patient desires to verify the location information, process 1100 proceeds YES to verify 1116 and query 1118 to determine if the location information is correct. If the location information is not correct, process 1100 proceeds NO to revise the location information in the search 1120. In an embodiment, the location information is revised by the user and/or potential patient by entering address information into a text box through input means. In another embodiment, the location information is revised by selecting a different address from a list of addresses with the use of up-and-down arrows, such as the up-and-down arrows 445 shown in FIG. 4C. Any type of means of revising the location information may be used in embodiments. Where the location information is correct, process 1100 proceeds YES to submit search request 1122. Returning to query 1114, where the user and/or potential patient does not desire to verify the location information, process 1100 proceeds NO to submit search request 1122. Following the processing of the search request, search results are received 1124, and process 1100 terminates at END operation 1126. FIG. 11 is an example of possible operational characteristics for receiving location information from a location system for assisting a user and/or potential patient with performing a search for a healthcare facility in accordance with embodiments disclosed herein. Operational steps depicted may be combined into other steps and/or rearranged. Further, fewer or additional steps may be used, for example.

Figure 12:
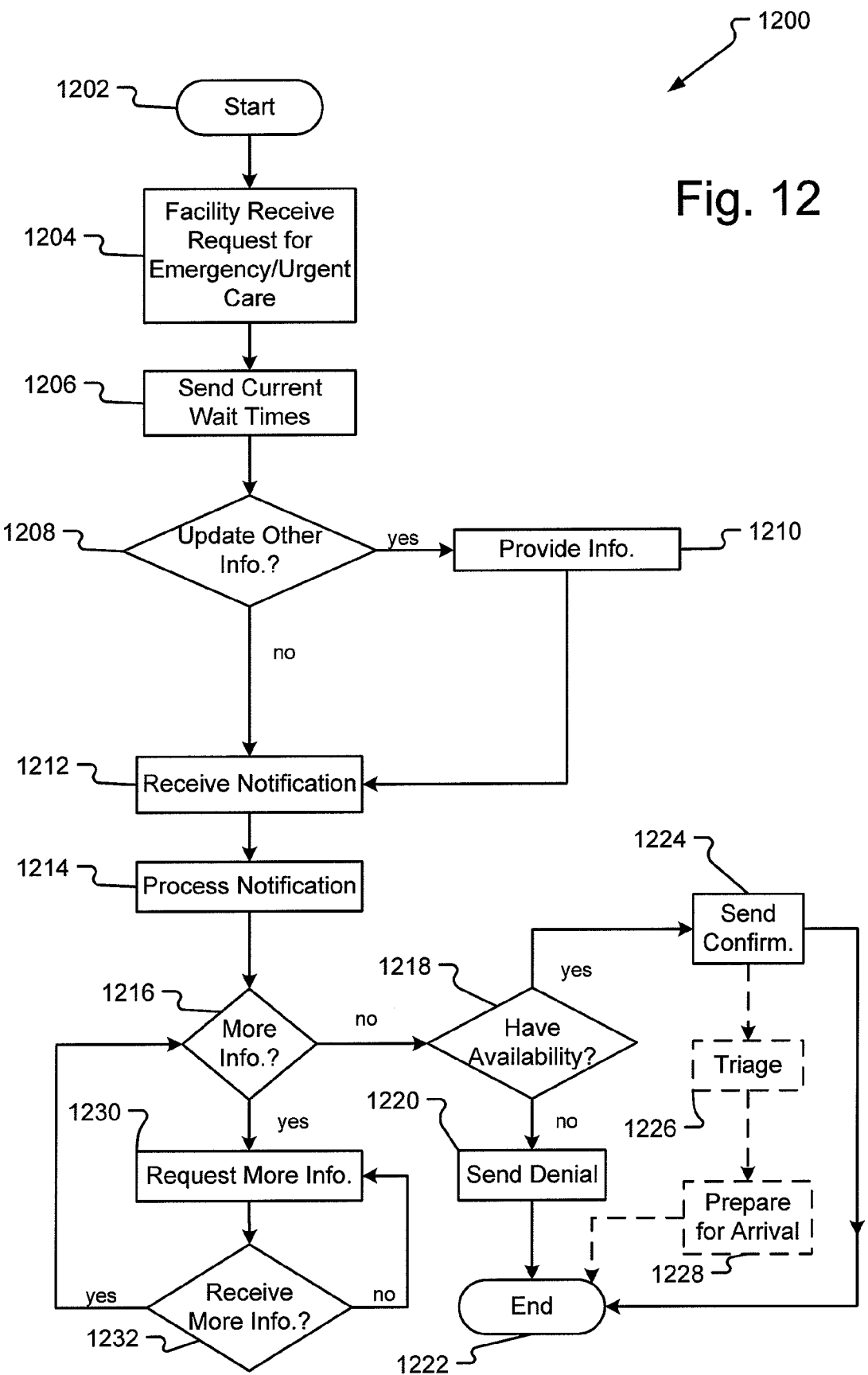
FIG. 12 depicts a flow diagram illustrating the operational characteristics of a process for receiving notification from a user to be admitted at an emergency/urgent/convenient care facility and obtaining triage type data over a network in accordance with embodiments disclosed herein.

Next, FIG. 12 illustrates example operational characteristics of a method for processing, by a healthcare facility, a request for treatment, in accordance with embodiments disclosed herein. START operation 1202 is initiated, and process 1200 proceeds to receive a request for emergency, urgent care, and/or convenient care 1204. Next, the facility responds with its current wait times 1206. In other embodiments, additional or different information is also provided depending on the request and on the information the facility desires to convey. Process 1200 next proceeds to query 1208 to determine whether the facility desires to update any other information in addition to current wait times. Where the facility desires to update other information, process 1200 proceeds YES to provide information 1210. Where the facility does not desire to update other information, process 1200 proceeds NO to receive notification 1212, in which the facility receives a notification from a user and/or potential patient of his/her expected arrival at the facility. The facility then processes the notification 1214, and determines at query 1216 whether more information is desired and/or needed to determine if the facility can accept the potential patient. Where additional information is desired and/or needed, process 1200 proceeds YES to request more information 1230. In an embodiment, such additional information is requested from the user and/or potential patient. In another embodiment, such additional information is requested from, and provided by, the company providing the healthcare facility search services. Next, query 1232 determines whether the additional information requested has been received. Where no additional information has been received, process 1200 proceeds NO to request more information 1230, and steps 1230-1232 repeat. Where more information is received, process 1200 proceeds YES to query 1216 to determine if additional information is needed and/or desired. Where no additional information is needed and/or desired, process 1200 proceeds NO to query 1218 to determine if the facility has availability to accept the potential patient for treatment. Where availability exists, process 1200 proceeds YES to send confirmation 1224, in which a confirmation response is sent confirming the facility's ability to accept the potential patient for treatment. Process 1200 may optionally (as shown by dashed lines) proceed to triage step 1226 to allow the facility to request further information regarding the potential patient's condition to allow the facility to triage the patient before his/her arrival at the facility. The facility may also optionally prepare for arrival 1228 according to an embodiment. In another embodiment, the facility's preparation for the patient's arrival is not an optional step but, instead, is conducted by the facility as a routine step in the process. Process 1200 then terminates at END operation 1222. Returning to query 1218, where the facility does not have any availability, process 1200 proceeds NO to send a denial response, in which the facility denies the potential patient's request for admittance. Process 1200 then proceeds to END operation 1222 and terminates. FIG. 12 is an example of possible operational characteristics for processing a request by a user to be admitted at an emergency, urgent care, and/or convenient care facility and for obtaining triage type data over a network in accordance with embodiments disclosed herein. Operational steps depicted may be combined into other steps and/or rearranged. Further, fewer or additional steps may be used, for example.

Figure 13:
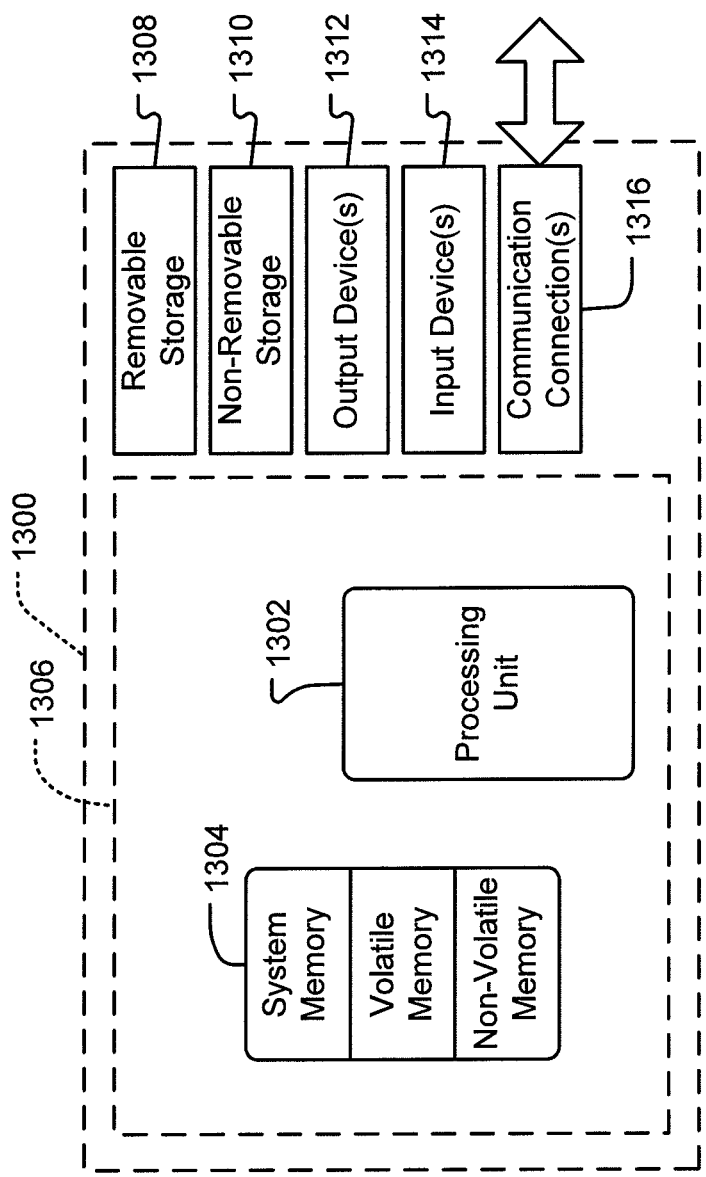
FIG. 13 depicts an example computing system upon which embodiments of the present disclosure may be implemented.

Finally, FIG. 13 illustrates an example computing system 1300 upon which embodiments disclosed herein may be implemented. A computer system 1300, such as client computer 102 or servers 108, 114, 116, 124, 132, or 134, which has at least one processor 1302 for exchanging form data and messages related thereto, as shown in FIG. 13, is depicted in accordance with embodiments disclosed herein. The system 1300 has a memory 1304 comprising, for example, system memory, volatile memory, and non-volatile memory. In its most basic configuration, computing system 1300 is illustrated in FIG. 13 by dashed line 1306. Additionally, system 1300 may also include additional storage (removable and/or non-removable) including, but not limited to, magnetic or optical disks or tape. Such additional storage is illustrated in FIG. 13 by removable storage 1308 and non-removable storage 1310.

The term computer readable media as used herein may include computer storage media. Computer storage media may include volatile and nonvolatile, removable and non-removable media implemented in any method or technology for storage of information, such as computer readable instructions, data structures, program modules, or other data. System memory 1304, removable storage 1308, and non-removable storage 1310 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1300. Any such computer storage media may be part of device 1300. The illustration in FIG. 13 is intended in no way to limit the scope of the present disclosure.

The term computer readable media as used herein may also include communication media. Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

System 1300 may also contain communications connection(s) 1316 that allow the device to communicate with other devices. Additionally, to input content into the form fields displayed on a User Interface (UI) on client computer 102, for example, as provided by a corresponding UT module on client computer 102, for example, in accordance with an embodiment of the present disclosure, system 1300 may have input device(s) 1314 such as a keyboard, mouse, pen, voice input device, touch input device, etc. Output device(s) 1312 such as a display, speakers, printer, etc. may also be included. All of these devices are well known in the art and need not be discussed at length here. The aforementioned devices are examples and others may be used.

Having described embodiments of the present disclosure with reference to the figures above, it should be appreciated that numerous modifications may be made to the embodiments that will readily suggest themselves to those skilled in the art and which are encompassed within the scope and spirit of the present disclosure and as defined in the appended claims. Indeed, while embodiments have been described for purposes of this disclosure, various changes and modifications may be made which are well within the scope of the present disclosure.

Similarly, although this disclosure has used language specific to structural features, methodological acts, and computer-readable media containing such acts, it is to be understood that the subject matter defined in the appended claims is not necessarily limited to the specific structure, acts, features, or media described herein. Rather, the specific structures, features, acts, and/or media described above are disclosed as example forms of implementing the claims. Aspects of embodiments allow for multiple client computers, multiple servers, and multiple networks, etc. Or, in other embodiments, a single client computer with a single server and single network are used. One skilled in the art will recognize other embodiments or improvements that are within the scope and spirit of the present disclosure. Therefore, the specific structure, acts, or media are disclosed as example embodiments of implementing the present disclosure. The disclosure is defined by the appended claims.

What is claimed is:

1. A computer-implemented method for providing healthcare facility information to potential patients, the method comprising:
    receiving, by a server computer, a request for information regarding one or more types of healthcare facilities, wherein the request is transmitted over a computer network, and wherein the one or more types of healthcare facilities comprises one or more from the group consisting of: emergency care, urgent care, and convenient care;
    receiving one or more ranking preferences;
    providing a results list based on the request for information, wherein the results list comprises information regarding two or more healthcare facilities, and wherein the two or more healthcare facilities are ordered in the results list based at least in part on the one or more ranking preferences, the results list further comprising a reminder to call 9-1-1 for immediate care;
    receiving a selection of a first healthcare facility of the two or more healthcare facilities;
    in response to receiving the selection, providing a notification form for the first healthcare facility, wherein identification information for the first medical healthcare facility is displayed on the notification form, and wherein the notification form requests personal information comprising a first name, a last name, and a phone number;
    receiving the notification form with data entered into the notification form;
    transmitting the request to visit the selected first healthcare facility, wherein transmitting the request comprises sending the notification form to the first healthcare facility; and
    in response to transmitting the request, sending a confirmation page, wherein the confirmation page comprises a time based upon the request.

2. The method of claim 1, wherein the information regarding one or more healthcare facilities further comprises information related to one or more from a group consisting of: closest geographic proximity of the one or more healthcare facilities, and quality ratings of the one or more healthcare facilities.

3. The method of claim 1, wherein the data entered into the notification form further comprises an estimated arrival time of a first potential patient at the first healthcare facility.

4. The method of claim 1, further comprising providing a contact mechanism to directly contact a healthcare practitioner for a medical consultation.

5. The method of claim 4, wherein the contact mechanism comprises one or more from the group consisting of: a phone number, an electronic mail (email) address, and a Short Message Service (SMS) address.

6. The method of claim 5, wherein the contact mechanism is unique to allow for tracking of use of the contact mechanism.

7. The method of claim 1, wherein the notification form with data is received from a first potential patient.

8. The method of claim 7, further comprising:
    receiving a response from the first healthcare facility to the notification form, wherein the response comprises confirming to admit the first potential patient to the first healthcare facility.

9. The method of claim 7, further comprising:
    sending a request for additional information to the first potential patient, wherein the additional information comprises information to allow the first healthcare facility to triage the first potential patient.

10. The method of claim 7, wherein one or more portions of the data entered into the notification form is received from a navigation satellite system, and wherein the one or more portions of the data from the navigation satellite system identifies the first potential patient's current geographic location.

11. The method of claim 7, wherein one or more portions of the notification form are automatically populated with data from a database comprising data of users affiliated with a company providing the healthcare facility information to potential patients.

12. The method of claim 1, further comprising a contact mechanism for directly contacting the first healthcare facility, and wherein the contact mechanism comprises one or more from the group consisting of: a phone number, an electronic mail (email) address, and a Short Message Service (SMS) address.

13. The method of claim 12, wherein the contact mechanism is unique to allow for tracking of use of the contact mechanism.

14. A computer system for connecting healthcare facilities with potential patients, the system comprising:
    at least one computer processor; and
    memory coupled with and readable by the at least one computer processor and comprising a series of instructions that, when executed by the at least one computer processor, cause the at least one computer processor to:
    receive a request for information regarding one or more types of emergency care facilities;
    receive one or more ranking preferences;
    provide a results list based on the request for information, wherein the results list comprises information regarding two or more emergency care facilities, and wherein the two or more emergency care facilities are ordered based at least in part on the one or more ranking preferences, the results list further comprising a reminder to call 9-1-1 for immediate care;

receive a selection of a first healthcare facility of the one or more emergency care facilities;

in response to receiving the selection, providing a notification form for the first emergency care facility, wherein the notification is displayed electronically, wherein identification information for the first emergency care facility is displayed on the notification form, and wherein the notification form requests personal information comprising a first name, a last name, and a phone number;

receive the notification form with data entered into the notification form;

transmit the request to visit the selected first emergency care facility, wherein transmitting the request comprises sending the notification form to the first emergency care facility; and in response to transmitting the request, sending a confirmation page, wherein the confirmation page comprises a time based upon the request.

15. The system of claim 14, wherein the information regarding one or more emergency care facilities further comprises information related to one or more from a group consisting of: closest geographic proximity of the one or more emergency care facilities, and quality ratings of the one or more emergency care facilities.

16. The system of claim 14, wherein the memory further comprises instructions that, when executed by the at least one computer processor, cause the at least one processor to:

send a request for additional information to the first potential patient, wherein the additional information comprises information to allow the first emergency care facility to triage the first potential patient.

17. The method of claim 7, wherein one or more portions of the data entered into the notification form is received from a navigation satellite system, and wherein the one or more portions of the data from the navigation satellite system identifies the first potential patient's current geographic location.

18. A non-transitory computer storage medium having computer-executable instructions stored thereon that, when executed by at least one processor, perform a method for providing a method for requesting healthcare facility information, the method comprising:

requesting healthcare facility information for one or more types of healthcare facilities, wherein the one or more types of healthcare facilities comprises one or more from the group consisting of: emergency care, urgent care, and convenient care; providing search criteria for the one or more types of healthcare facilities;

providing one or more ranking preferences;

receiving a search results list, wherein the search results list comprises information regarding two or more healthcare facilities, and wherein the two or more healthcare facilities are ordered based at least in part on the one or more ranking preferences, the results list further comprising a reminder to call 9-1-1 for immediate care;

selecting a first healthcare facility of the one or more healthcare facilities;

in response to selecting the first healthcare facility, receiving a notification form for the first healthcare facility, wherein identification information for the first medical healthcare facility is displayed on the notification form, and wherein the notification form requests personal information comprising a first name, a last name, and a phone number;

sending a request to visit the first healthcare facility, wherein sending the request comprises providing the notification form;

in response to providing the notification form, receiving a confirmation page, wherein the confirmation page comprises a time based upon the request.

19. The computer storage medium of claim 18, wherein the information regarding one or more healthcare facilities further comprises information related to one or more from a group consisting of: wait times at the one or more healthcare facilities, closest geographic proximity of the one or more healthcare facilities, and quality ratings of the one or more healthcare facilities.

20. The computer readable storage medium of claim 18, wherein a first portion of notification form is automatically populated with data received from a navigation satellite system, and wherein the data received from the navigation satellite system identifies a current geographic location of a first user requesting the healthcare facility information.

* * * * *